US010864363B2

(12) United States Patent
Hakim

(10) Patent No.: US 10,864,363 B2
(45) Date of Patent: Dec. 15, 2020

(54) EXTERNALLY PROGRAMABLE MAGNETIC VALVE ASSEMBLY AND CONTROLLER

(71) Applicant: Carlos A. Hakim, Coconut Grove, FL (US)

(72) Inventor: Carlos A. Hakim, Coconut Grove, FL (US)

( * ) Notice: Subject to any disclaimer, the term of this patent is extended or adjusted under 35 U.S.C. 154(b) by 666 days.

(21) Appl. No.: 15/675,497

(22) Filed: Aug. 11, 2017

(65) Prior Publication Data

US 2018/0126147 A1 May 10, 2018

Related U.S. Application Data

(60) Provisional application No. 62/374,046, filed on Aug. 12, 2016.

(51) Int. Cl.
*A61M 39/24* (2006.01)
*A61M 27/00* (2006.01)
(Continued)

(52) U.S. Cl.
CPC ............ *A61M 39/24* (2013.01); *A61B 5/031* (2013.01); *A61B 5/032* (2013.01); *A61B 5/4836* (2013.01);
(Continued)

(58) Field of Classification Search
CPC .... A61M 39/24; A61M 27/00; A61M 27/006; A61M 2039/226; A61M 2039/2493; A61M 2205/0272; A61M 2205/32; A61M 2205/3317; A61M 2205/3344; A61M 2205/50; A61M 2205/8206; A61B 5/031; A61B 5/032; A61B 5/4836; A61B 5/686;
(Continued)

(56) References Cited

U.S. PATENT DOCUMENTS 4,595,390 A * 6/1986 Hakim .................. A61F 2/0036
137/530
6,050,969 A 4/2000 Kraus
(Continued)

FOREIGN PATENT DOCUMENTS

| | | | |
|---|---|---|---|
| CN | 105764562 | A | 7/2016 |
| EP | 2992924 | A1 | 3/2016 |
| WO | 199520781 | A1 | 8/1995 |

OTHER PUBLICATIONS

Extended European Search Report from corresponding European Application No. 17840370.5 dated Mar. 5, 2020.
(Continued)

*Primary Examiner* — Philip R Wiest
(74) *Attorney, Agent, or Firm* — Lando & Anastasi, LLP

(57) ABSTRACT

An externally programmable shunt valve assembly that includes a motor having a rotor that is operable in response to an externally applied magnetic field and configured to increase or decrease the working pressure of the shunt valve assembly. The motor may further include a position sensing mechanism that allows a position of the rotor, and associated pressure setting of the valve, to be determined using an external magnetic sensor. In certain examples the motor further includes a mechanical brake that is magnetically operable between a locked position and an unlocked position and which, in the locked position, prevents rotation of the rotor.

36 Claims, 75 Drawing Sheets

(51) Int. Cl.

| | |
|---|---|
| ***H02K 37/12*** | (2006.01) |
| ***A61B 5/00*** | (2006.01) |
| ***A61B 5/03*** | (2006.01) |
| ***F16K 31/04*** | (2006.01) |
| ***F16K 31/524*** | (2006.01) |
| *A61M 39/22* | (2006.01) |

(52) U.S. Cl.
CPC ............ *A61B 5/686* (2013.01); *A61B 5/6868* (2013.01); *A61M 27/00* (2013.01); *A61M 27/006* (2013.01); *F16K 31/047* (2013.01); *F16K 31/52408* (2013.01); *H02K 37/12* (2013.01); *A61B 2505/05* (2013.01); *A61B 2562/0247* (2013.01); *A61M 2039/226* (2013.01); *A61M 2039/2493* (2013.01); *A61M 2205/0272* (2013.01); *A61M 2205/32* (2013.01); *A61M 2205/3317* (2013.01); *A61M 2205/3344* (2013.01); *A61M 2205/50* (2013.01); *A61M 2205/8206* (2013.01)

(58) Field of Classification Search
CPC ................ A61B 5/6868; F16K 31/047; F16K 31/52408
See application file for complete search history.

(56) References Cited

U.S. PATENT DOCUMENTS

| | | | | |
|---|---|---|---|---|
| 2007/0005000 | A1 | 1/2007 | Ludin | |
| 2011/0112460 | A1 | 5/2011 | Murphy | |
| 2012/0310139 | A1* | 12/2012 | Murphy | A61M 27/006 604/9 |
| 2013/0106322 | A1 | 5/2013 | Drye | |
| 2013/0317283 | A1 | 11/2013 | LaRose et al. | |
| 2014/0052047 | A1 | 2/2014 | Wilson | |
| 2014/0336560 | A1 | 11/2014 | Hakim | |
| 2016/0220794 | A1 | 8/2016 | Negre | |

OTHER PUBLICATIONS

International Search Report and the Written Opinion of the International Searching Authority from corresponding PCT/US2017/046601 dated Dec. 28, 2017.

* cited by examiner

SECTION A-A

SECTION C-C

| Coils | 1 | 2 | 3 | 4 |
|---|---|---|---|---|
| Step 1 | S | X | X | X |
| Step 2 | X | S | X | X |
| Step 3 | N | X | X | X |
| Step 4 | X | N | X | X |

| Coils | 1 | 2 | 3 | 4 |
|---|---|---|---|---|
| Step 1 | S | X | X | X |
| Step 2 | X | S | X | X |
| Step 3 | N | X | X | X |
| Step 4 | X | N | X | X |

Clockwise Rotation

SECTION B-B

EXTERNALLY PROGRAMABLE MAGNETIC VALVE ASSEMBLY AND CONTROLLER

CROSS-REFERENCE TO RELATED APPLICATIONS

This application claims the benefit under 35 U.S.C. § 119(e) and PCT Article 8 of U.S. Provisional Application No. 62/374,046 filed on Aug. 12, 2016, and titled "EXTERNALLY PROGRAMMABLE MAGNETIC VALVE ASSEMBLY AND CONTROLLER," which is herein incorporated by reference in its entirety.

BACKGROUND

Hydrocephalus is a condition associated with ventricular enlargement caused by net accumulation of fluid in the ventricles of the brain. Non-communicating hydrocephalus is hydrocephalus associated with an obstruction in the ventricular system and is generally characterized by increased cerebrospinal fluid (CSF) pressure. In contrast, communicating hydrocephalus is hydrocephalus associated with obstructive lesions within the subarachnoid space. Normal Pressure Hydrocephalus (NPH), a form of communicating hydrocephalus, primarily occurs in persons over 60 years of age and is characterized by CSF at nominally normal pressure. Classic symptoms of NPH include gait disturbance, incontinence and dementia. In summary, NPH presents as an enlargement of the ventricles with a virtually normal CSF pressure.

The objective in the treatment of hydrocephalus is to reduce the ventricular pressure so that ventricular size returns to a normal level. Hydrocephalus is often treated by implanting into the brain a shunt that drains excess CSF from the ventricles or from the lumbar thecal space (in communicating hydrocephalus). Such shunts are termed ventriculoatrial (VA) when they divert fluid from the ventricle to the atrium, or ventriculoperitoneal (VP) when fluid is diverted from the ventricle to the peritoneum, or lumboperitoneal (LP) when CSF is diverted from the lumbar region to the peritoneum. These shunts are generally comprised of a cerebral catheter (for ventricular shunts) inserted through the brain into the ventricle or a lumbar catheter (for lumbar shunts) inserted through a needle into the lumbar thecal space and a one-way valve system that drains fluid from the ventricle into a reservoir of the body, such as the jugular vein (ventricular shunts) or the peritoneal cavity (ventricular or lumbar shunts).

U.S. Pat. No. 4,595,390 describes a shunt that has a spherical sapphire ball biased against a conical valve seat by stainless steel spring. The pressure of the CSF pushes against the sapphire ball and spring in the direction tending to raise the ball from the seat. When the pressure difference across the valve exceeds a so-called "popping" or opening pressure, the ball rises from the seat to allow CSF to flow through the valve and thereby vent CSF. U.S. Pat. No. 4,595,390 further describes an externally programmable shunt valve that allows the pressure setting of the valve to be varied by applying a transmitter that emits a magnetic signal over the head of the patient over the location of the implanted shunt. Use of an external programmer with a magnetic transmitter allows the pressure setting of the valve to be adjusted non-invasively according to the size of the ventricles, the CSF pressure and the treatment objectives.

U.S. Pat. No. 4,615,691 describes examples of a magnetic stepping motor that can be used with the shunt valve of U.S. Pat. No. 4,595,390, for example.

Although magnetically adjustable shunts allow the pressure of an implanted shunt to be adjusted externally, these existing shunts have some limitations. For example, when a patient with an implanted magnetically adjustable shunt valve is within proximity of a strong magnet or strong magnetic field, such as a magnetic resonance imaging (MRI) device, the pressure setting of the valve can change. In addition, verification of the pressure setting of existing magnetic valves can require use of a radiopaque marker on the valve that is detected using an X-ray taken of the location where the valve is implanted. Also, some programmers utilized to adjust the pressure setting of an implanted valve are relatively large and heavy and require a connection to a wall outlet.

It would therefore be desirable to design improved ventricular and lumbar shunts, as well as an improved programmer to adjust the shunts.

SUMMARY OF THE INVENTION

Aspects and embodiments are directed to an externally programmable valve assembly comprising a magnetic motor that is configured to increase or decrease the pressure setting of the valve either continuously or in finite increments. The valve assembly may be adapted for implantation into a patient to drain fluid from an organ or body cavity of the patient. In these embodiments, the valve assembly includes an inlet port adapted for fluid connection (either during manufacture or by the surgeon during surgery) to one end of a catheter. The second end of the catheter is inserted into the organ or body cavity to be drained of fluid. The valve assembly further includes an outlet port adapted for fluid connection to an end of a drainage catheter. The other end of the drainage catheter can be inserted into a suitable body cavity, such as a vein or the peritoneal cavity, or into a drainage reservoir external to the body, such as a bag. Examples of organs and body cavities that can be drained using the valve assembly of the invention include without limitation the eye, cerebral ventricle, peritoneal cavity, pericardial sac, uterus (in pregnancy), and pleural cavity. In particular, the valve assembly may be adapted for implantation into a patient suffering from hydrocephalus. In such embodiments, the inlet port is adapted for fluid connection to a first end of an inflow catheter (i.e. an intracerebral or intrathecal catheter) and the outlet port is adapted for fluid connection to a first end of a drainage catheter. When implanted in the patient, the second end of the intracerebral catheter is inserted in a ventricle or lumbar intrathecal space of the patient and the second end of the drainage catheter is inserted into a suitable body reservoir of the patient, such as the jugular vein or the peritoneal cavity. Thus, when implanted in the patient, this device provides fluid communication between the ventricle or lumbar region of the patient and the body reservoir of the subject, allowing cerebrospinal fluid to flow from the ventricle or lumbar region through the valve casing to the body reservoir when the intraventricular or CSF pressure exceeds the opening pressure of the valve assembly. The patient may suffer from hydrocephalus with increased intracranial pressure, or may suffer from normal pressure hydrocephalus. The removal of CSF from the ventricle or lumbar space reduces the intraventricular pressure.

Further aspects and embodiments are directed to methods of determining the pressure setting of an implanted valve assembly, and adjusting the pressure setting of the valve assembly following implantation into a patient. As discussed in more detail below, according to certain embodiments, adjustment of the pressure setting of the valve may be accomplished via displacement of a magnetically actuated rotor in the valve assembly, resulting in a change in the tension of a spring providing a biasing force against the valve element. The rotor will rotate within the rotor casing responsive to an applied external magnetic field.

As discussed in more detail below, certain aspects and embodiments are directed to a magnetically operable motor that is suitable for incorporation into an implantable valve assembly. The magnetic motor assembly includes a stator having a plurality of stator lobes, and a rotor that includes a plurality of magnetic poles and which is configured to rotate about the stator. An externally applied magnetic field (from outside the body into which the valve assembly is implanted) is used to magnetize the stator so as to cause rotation of the rotor, as discussed further below. The magnetically operable motor has the advantage of allowing mechanical movement within the implantable valve assembly to alter the pressure setting of the valve, avoiding the need for physical connection to the valve assembly from outside the body or the use of implanted batteries. Additionally, as discussed further below, embodiments of the magnetic motor assembly are configured to be highly resistant to any influence from external strong magnetic fields that are not specifically associated with desired control of the motor, such as fields generated by MRI or nuclear magnetic resonance (NMR) devices. Further, certain embodiments of the magnetic motor include a mechanism by which an individual, for example, a doctor, can view the current pressure setting of the valve in which the magnetic motor is used, without requiring the use of an X-ray or other imaging technique.

Certain aspects also include a method of decreasing ventricular size in a patient in need thereof, including surgically implanting the valve assembly into the patient, and setting the opening pressure of the valve to a pressure that is less than the ventricular pressure prior to implantation of the valve. Alternatively, the opening pressure of the implanted valve assembly may be set to a pressure that is higher than the ventricular pressure, such that the ventricular size may be increased in a patient in need thereof.

According to one embodiment a surgically-implantable shunt valve assembly comprises a housing, an exterior of the housing being formed of a physiologically-compatible material, and a magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, rotation of the rotor relative to the stator producing a selected pressure setting of the shunt valve assembly. The shunt valve assembly further comprises an inlet port positioned between the rotor casing and an exterior of the housing, the inlet port terminating at its rotor casing end in a valve seat, a spring, a valve element biased against the valve seat by the spring, the valve element and the valve seat together forming an aperture, and an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port.

Another embodiment is directed to a system comprising an externally programmable surgically-implantable shunt valve assembly, a non-implantable transmitter head, and a control device coupled to the transmitter head. The surgically-implantable shunt valve assembly may include a housing having an exterior formed of a physiologically compatible material, a magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, a number of the rotor permanent magnet elements being such that radially opposing ones of the plurality of rotor permanent magnet elements have the same magnetic polarity, rotation of the rotor relative to the stator producing a selected pressure setting of the shunt valve assembly, an inlet port positioned between the rotor casing and an exterior of the housing, the inlet port terminating at its rotor casing end in a valve seat, a spring, a valve element biased against the valve seat by the spring, the valve element and the valve seat together forming an aperture, and an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port. The non-implantable transmitter head may include a magnet assembly configured to produce the external magnetic field to induce the rotation of the rotor relative to the stator. The control device may be configured to provide a signal to the transmitter head to control the transmitter head to produce the external magnetic field so as to set the pressure setting of the shunt valve assembly to the selected pressure setting.

Another embodiment is directed to a surgically-implantable valve including a magnetic motor for adjusting a pressure setting of the valve, the magnetic motor being physically isolated from electrical power sources and powered by an external magnetic field applied from outside the valve. The magnetic motor may comprise a rotor including a circular rotor casing and a plurality of permanent rotor magnets disposed in a ring within the rotor casing and arranged with alternating magnetic polarities, the rotor casing configured to rotate about a central axis of rotation, and a stator composed of a magnetically soft and permeable material shaped as opposing circular stator discs and positioned with respect to each of four quadrants underneath the rotor magnets so that when magnetized under the influence of the external field the stator strengthens and orients a local magnetic field in its vicinity so as to cause incremental movement of the rotor about the central axis of rotation. The number of the permanent rotor magnets may be such that radially opposing ones of the plurality of permanent rotor magnets have either the same or opposite magnetic polarity.

According to another embodiment a surgically-implantable shunt valve assembly comprises a spring, a valve element biased against a valve seat by the spring, the valve element and the valve seat together forming an aperture through which fluid is shunted by the valve, and a magnetic motor for adjusting a pressure setting of the valve, the magnetic motor being physically isolated from electrical power sources and powered by an external magnetic field applied from outside the valve assembly. The magnetic motor may include a rotor having a rotor casing, a plurality of permanent rotor magnets disposed in a ring within the rotor casing and arranged with alternating magnetic polarities, and a cam that engages the spring, the rotor being configured to rotate about a central axis of rotation, and a stator composed of a magnetically soft and permeable material and positioned below the rotor so that when magnetized under the influence of the external field the stator strengthens and orients a local magnetic field in its vicinity so as to cause rotation of the rotor about the central axis of rotation, the rotation of the rotor causing rotation of the cam that adjust a tension of the spring against the valve element and thereby adjusts the pressure setting of the shunt valve assembly.

According to another embodiment a surgically-implantable shunt valve assembly comprises a spring, a valve element biased against a valve seat by the spring, the valve element and the valve seat together forming an aperture through which fluid is shunted by the valve, and a magnetic motor for adjusting a pressure setting of the valve, the magnetic motor being physically isolated from electrical power sources and powered by an external magnetic field applied from outside the valve assembly. The magnetic motor may include a rotor having a rotor casing, a plurality of permanent rotor magnets disposed in a ring within the rotor casing and arranged with alternating magnetic polarities, and a cam that engages the spring, the rotor being configured to rotate about a central axis of rotation, a stator composed of a magnetically soft and permeable material and positioned below the rotor so that when magnetized under the influence of the external field the stator strengthens and orients a local magnetic field in its vicinity so as to cause rotation of the rotor about the central axis of rotation, the rotation of the rotor causing rotation of the cam that adjust a tension of the spring against the valve element and thereby adjusts the pressure setting of the shunt valve assembly, and a mechanical brake magnetically operable between a locked position and an unlocked position and configured, in the locked position, to prevent rotation of the rotor.

Another embodiment is directed to a surgically-implantable valve including a magnetic motor for adjusting a pressure setting of the valve, the magnetic motor being isolated physically from electrical power sources and powered by the influence of an external magnetic field applied from outside the valve, the magnetic motor comprising a rotor including a circular rotor casing and a plurality of permanent rotor magnets disposed in a ring within the rotor casing and arranged with alternating magnetic polarities, the rotor casing configured to rotate about a central axis of rotation, and an X-shaped stator composed of a magnetically soft and permeable material shaped and positioned with respect to the rotor such that when magnetized under the influence of the external field, the stator strengthens and orients a local magnetic field in its vicinity so as to cause incremental movement of the rotor about the central axis of rotation. The number of the permanent rotor magnets may be such that radially opposing ones of the plurality of permanent rotor magnets have either the same or opposite magnetic polarity.

According to another aspect, a method of adjusting a working (operating) pressure of a shunt valve assembly implanted in a patient in need thereof, comprises applying an external magnetic field in proximity to the implanted shunt valve assembly and exterior to the patient.

According to one embodiment, a method of decreasing ventricular size in a patient in need thereof comprises implanting in the patient a shunt valve assembly, and setting the selected pressure of the valve assembly to a pressure that is less than a ventricular pressure of the patient prior to implantation of the valve.

According to another embodiment, a method of treating a patient suffering from hydrocephalus comprises implanting in the patient a shunt valve assembly, and setting the selected pressure of the shunt valve assembly to a pressure that is less than a ventricular pressure of the patient.

In another embodiment, a method of increasing ventricular size in a patient in need thereof comprises implanting in the patient a shunt valve assembly, and setting the selected pressure of the shunt valve assembly to a pressure that is greater than a ventricular pressure of the patient.

During the course of treatment, it is anticipated that increasing or decreasing the selected operating pressure of the valve will be required to be performed by the clinician to effectively manage the patient's condition. However, during use, the valve will be exposed to environmental magnetic fields that may potentially change the operating pressure of the valve. Aspects and embodiments provide a valve mechanism design that facilitates adjusting the valve mechanism using a magnetic field produced by the programmer while resisting adjustment by extraneous environmental magnetic fields.

Further aspects and embodiments are directed to a kit for setting a pressure in a surgically-implantable shunt valve. In some embodiments, the kit comprises a surgically-implantable shunt valve assembly having a magnetically operable motor configured to provide a selected pressure setting of the shunt valve assembly; a pressure reader configured to provide a pressure reading of the surgically-implantable shunt valve assembly; and a programmer having at least one programmer magnet, the at least one programmer magnet being selectively movable and configured to actuate the magnetically operable motor to allow a user to adjust the pressure setting of the surgically-implantable shunt valve assembly to match a pressure setpoint of the programmer.

In some embodiments, the pressure reader further comprises an arrow on an upper surface of the pressure reader.

In some embodiments, the pressure reader further comprises a concave surface defined on a lower surface of the pressure reader.

In some embodiments, the programmer further comprises a user interface.

In some embodiments, the programmer further comprises a first button to increase the pressure setpoint and a second button to decrease the pressure setpoint.

In some embodiments, the programmer further comprises a wheel being rotatable in a first direction to increase the pressure setpoint, and the wheel being rotatable in a second direction to decrease the pressure setpoint.

In some embodiments, the programmer further comprises a cavity on a lower surface of the programmer.

In some embodiments, the pressure reader includes one of a magnet and a Hall sensor.

In some embodiments, the surgically-implantable shunt valve assembly comprises a housing, an exterior of the housing being formed of a physiologically-compatible material; the magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, rotation of the rotor relative to the stator producing the selected pressure setting of the shunt valve assembly; an inlet port positioned between the rotor casing and an exterior of the housing, the inlet port terminating at its rotor casing end in a valve seat; a spring; a valve element biased against the valve seat by the spring, the valve element and the valve seat together forming an aperture; and an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port.

In some embodiments, the surgically-implantable shunt valve assembly includes a rotor marker attached to the rotor such that the rotor marker rotates with the rotor and a housing marker fixedly attached to the housing, wherein a position of the rotor marker relative to the housing marker is indicative of the pressure setting of the surgically-implantable shunt valve assembly.

In some embodiments, the rotor marker comprises tantalum and the housing marker comprises tantalum.

In some embodiments, the magnetically operable motor is a stepper motor having a rotatable rotor, and wherein the surgically-implantable shunt valve assembly further comprises a mechanical brake mechanism magnetically operable between a locked position and an unlocked position and configured, in the locked position, to prevent rotation of the rotor; and an indicator magnet assembly configured to allow an external sensor to magnetically determine a position of the rotor and thereby to determine the pressure setting.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying drawings in which like reference characters refer to the same parts throughout the different views. For purposes of clarity, not every component may be labeled in every drawing. The drawings are not necessarily to scale, emphasis instead being placed upon illustrating the principles of the invention. The drawings are included to provide illustration and a further understanding of the various aspects and embodiments, and are incorporated in and constitute a part of this specification, but are not intended as a definition of the limits of the invention. In the drawings.

DETAILED DESCRIPTION OF THE INVENTION

Aspects and embodiments are directed to a valve assembly that incorporates a magnetic motor configured to increase or decrease the working pressure of the valve either continuously or in finite increments. As discussed in more detail below, by magnetically repositioning a rotor within a casing of the valve assembly, the opening pressure of the valve element may be adjusted, thereby increasing or decreasing the flow of fluid through the valve assembly. Certain embodiments of the valve assembly are adapted for implantation into a patient suffering from hydrocephalus, and may be used to drain CSF.

In particular, certain aspects and embodiments provide an externally and magnetically programmable valve incorporating a magnetic motor and external controller having the following features. The valve is configured such that an operator, for example, a doctor, is able to adjust the valve either continuously or in small pressure increments (e.g., increments of approximately 10 mm $H_2O$) up to a pressure of about 200 mm $H_2O$, and the valve has a "closed" setting of approximately 300-400 mm $H_2O$. The valve is highly resistant to non-programming external magnetic fields in the environment, such as the magnetic field of a 3 Tesla MRI, for example, such that the pressure setting of the valve does not change appreciably when the patient is in the proximity of an MRI machine or other instrument (other than the valve controller) that generates a magnetic field. In certain embodiments, the valve is configured such that the operator (e.g., the doctor) is able to verify the pressure setting of the valve with a method other than X-Rays. Furthermore, according to certain embodiments the valve controller is small, very portable, and battery-operated. These and other features and configurations of the valve according to various embodiments are discussed in more detail below.

Figure 1A:
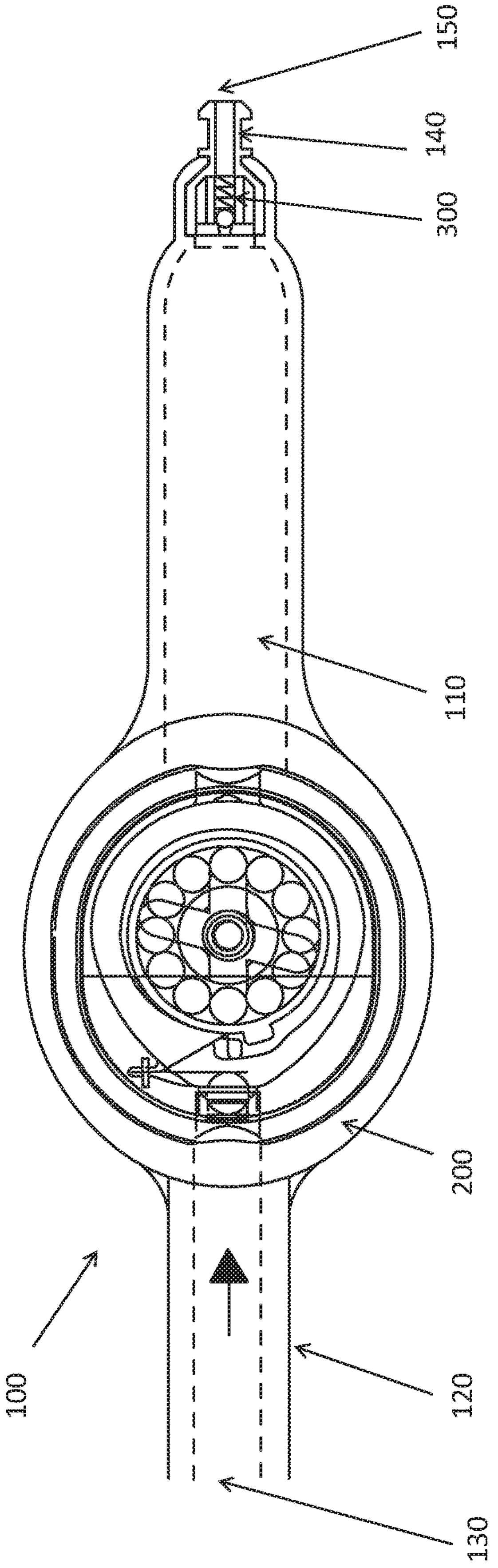
FIG. 1A is a plan view of one example of an implantable valve assembly, showing a top view, according to aspects of the invention.
Figure 1B:
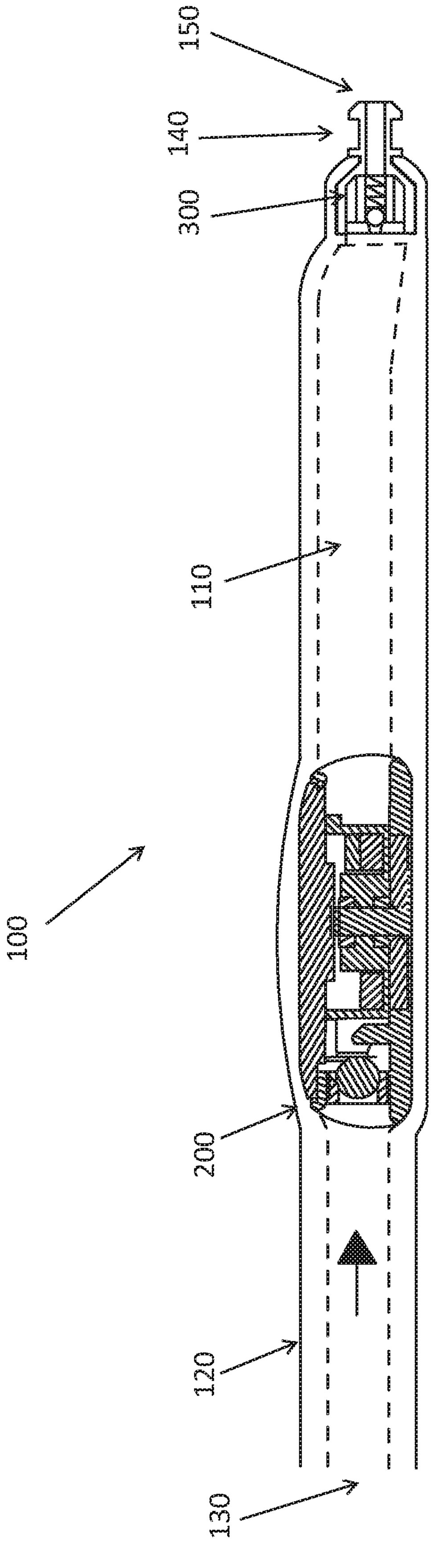
FIG. 1B is a cross-sectional view of the valve assembly of FIG. 1A.

Referring to FIGS. 1A and 1B, there is illustrated one example of an implantable shunt valve assembly 100 including two valves 200 and 300 separated by a pumping chamber 110. In one example, a ventricular catheter 120 can be connected to an inlet 130 of the valve assembly 100, and a drainage catheter can be attached to a connector 140 and connected to an outlet 150 of the valve assembly. Depression of the pumping chamber 110 pumps fluid through the valve 300 toward the outlet 150 and the drainage catheter. Releasing the pumping chamber after it has been depressed pumps fluid through the valve 200. The valve 200 is an externally programmable valve including a magnetic motor, as discussed in more detail below. The second valve 300 can be a check valve, for example. In this case, after passing through the programmable valve 200, fluid flows through the check valve 300 before exiting into the drainage catheter. In one example the programmable valve 200 operates to keep the valve assembly 100 closed until the fluid pressure rises to a predetermined pressure setting of the valve. Generally, the check valve 300 may be set at a low pressure, allowing the pressure setting of the programmable valve 200 including the magnetic motor to control the flow of fluid through the valve assembly 100. In other examples, the second valve 300 can be a gravity-activated valve that allows the valve assembly 100 to automatically adjust in response to changes in CSF hydrostatic pressure that occur when the patient's posture changes (i.e., moving abruptly from a horizontal (recumbent) to a vertical (erect) position). In particular, to avoid the valve opening responsive to these pressure changes, which could cause over-drainage of CSF, the valve assembly 100 can include a gravity activated valve connected in series with and on the outlet side of the programmable valve 200, as shown in FIGS. 1A and 1B, the gravity activated valve being configured to open at higher pressures when the patient is substantially vertical.

Those skilled in the art will appreciate, given the benefit of this disclosure, that the length, size, and shape of various embodiments of the valve assembly 100 can be adjusted. Certain embodiments of the valve assembly 100 may further comprise a reservoir or pre-chamber or antechamber for sampling the fluid and/or injecting pharmaceutical agents or dyes, power on/off devices, anti-siphon or other flow compensating devices, and/or additional catheters. When included, the pre-chamber (not shown in FIGS. 1A and 1B) would be connected between the inlet 130 and the programmable valve 200. According to certain embodiments, the valve assembly 100 may include a combination of the pumping chamber 110, a pre-chamber, the second valve 300 (which can be a check valve or gravity-activated valve, for example), and optionally an anti-siphon device (not shown). In other embodiments, one or more of these components may be omitted. For example, the valve assembly 100 may include the pumping chamber 110 and second valve 300, without a pre-chamber, as shown in FIGS. 1A and 1B. The pumping chamber 110 may also or alternatively be omitted. In such embodiments, after the fluid passes through the programmable valve 200, it flows through the second valve 300. Alternatively, the valve assembly 100 may include a pre-chamber, with or without the pumping chamber 110 or the second valve 300. The valve assembly 100 can be surgically implanted into a patient using well-known procedures.

Figure 2:
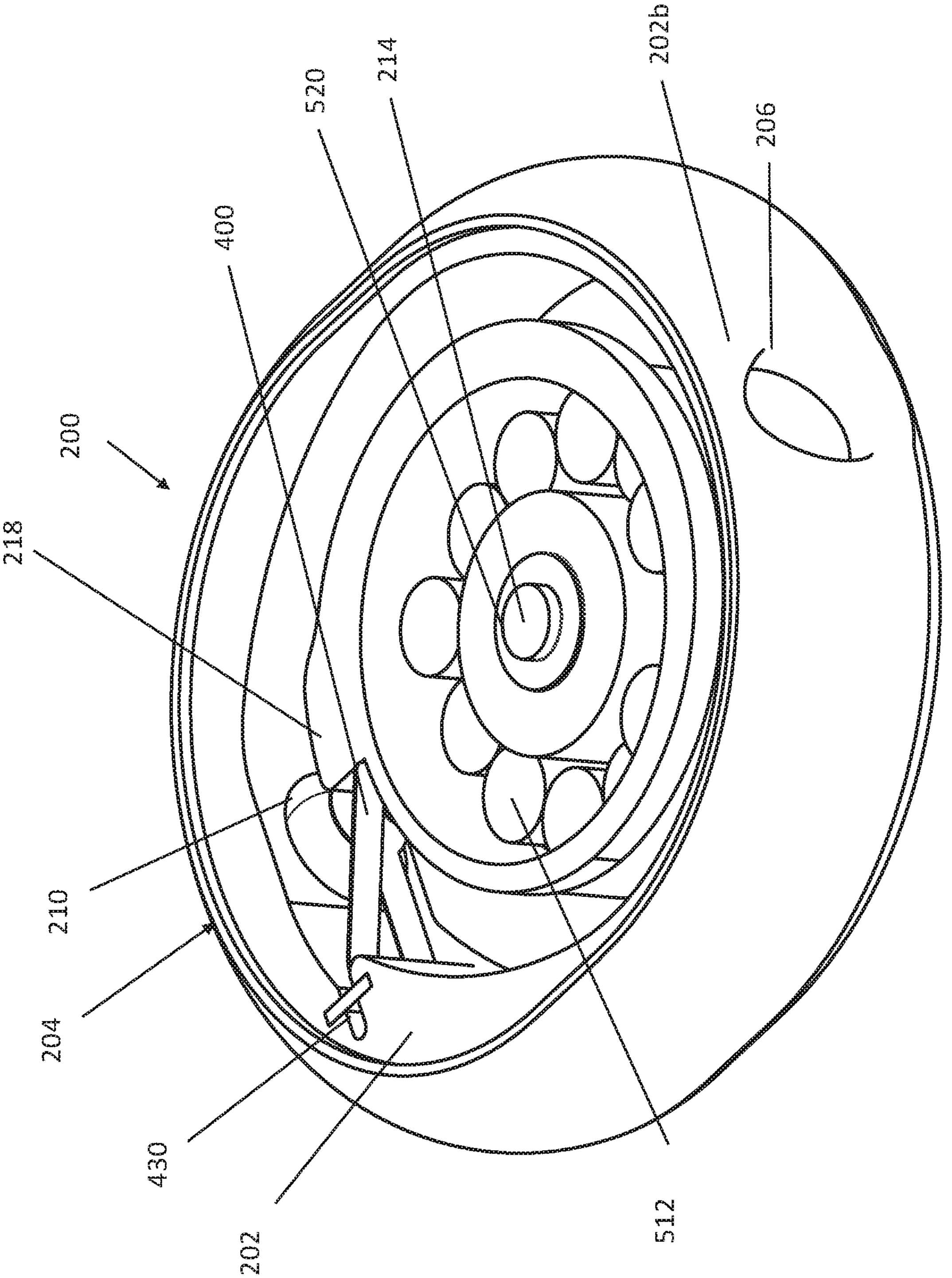
FIG. 2 is a three-dimensional drawing of one example of an implantable valve according to aspects of the present invention.
Figure 3A:
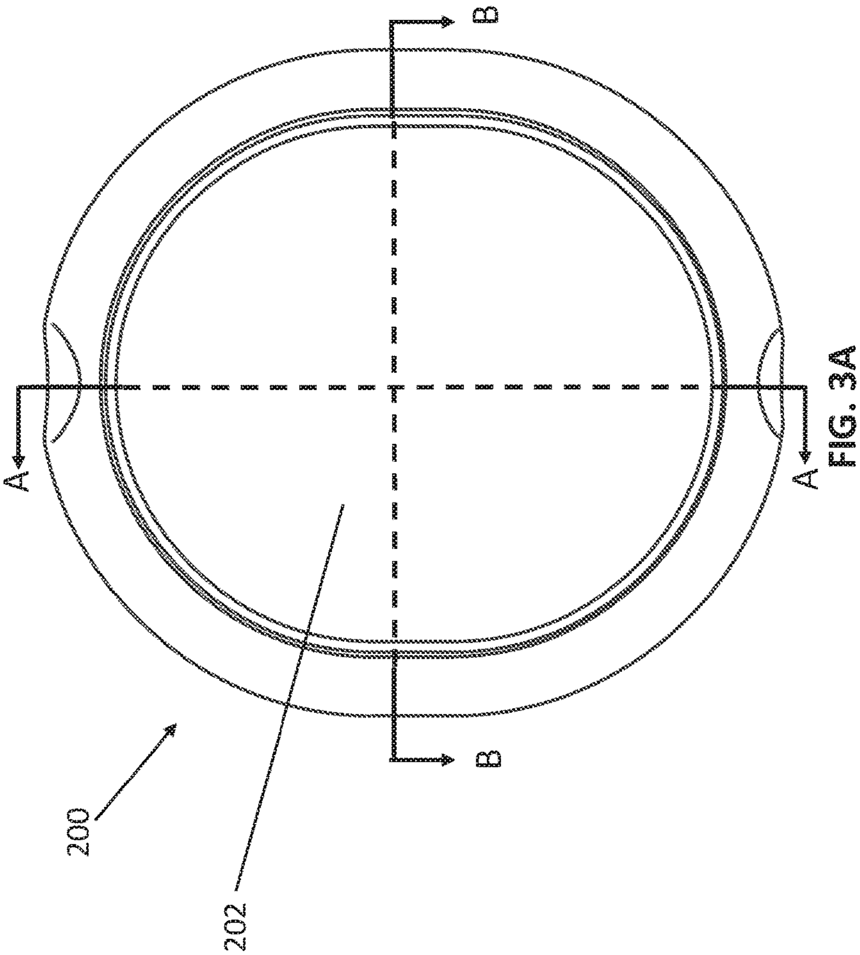
FIG. 3A is a diagram showing a plan view of one example of an implantable valve, corresponding to the example shown in FIG. 2, according to aspects of the invention.
Figure 3B:
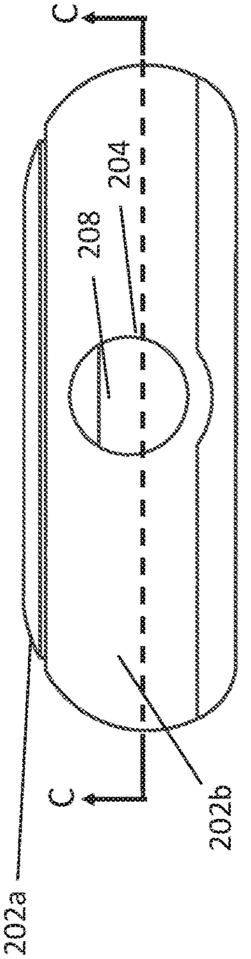
FIG. 3B is a side view of the example of the implantable valve shown in FIG. 3A.

FIG. 2 illustrates a three-dimensional view of one example of an implantable magnetically programmable valve 200 according to certain aspects. FIGS. 3A and 3B illustrate external views of the implantable magnetically programmable valve 200 of FIG. 2, according to certain embodiments. FIG. 3A is a plan view and FIG. 3B is an end view. The valve 200 includes a valve body 202 (also referred to as a housing) that houses the components of the valve. The valve 200 includes an inlet port 204 and an outlet port 206. The inlet port 204 may be connected to a proximal (or inflow) catheter, and the outlet port 206 may be connected to a distal or outflow catheter. In the case of a valve assembly that shunts CSF fluid, the proximal catheter may be the ventricular catheter 120 or a lumbar catheter. In this case, the CSF fluid from the ventricle enters the ventricular catheter or lumbar catheter and enters the inlet port 204 of the valve assembly 100. The distal catheter acts as the drainage catheter connected to the connector 140 to direct fluid to a remote location of the body (such as the right atrium (VA shunting) of the heart or the peritoneal cavity (VP or LP shunting) for drainage.

The valve body 202 may include a top cap 202*a* and a bottom cap 202*b* that mates with the top cap 202*a* to form a sealed enclosure that is suitable for implantation into the human body. The "top" of the valve 200 is the side of the device oriented to face up toward the patient's scalp when implanted. The valve body 202 may be made from any physiologically compatible material. Non-limiting examples of physiologically compatible materials include polyethersulfone and silicone. As will be appreciated by those skilled in the art, the valve body 202 may have a variety of shapes and sizes, at least partially dependent on the size, shape, and arrangement of components within the valve 200.

Figure 4A:
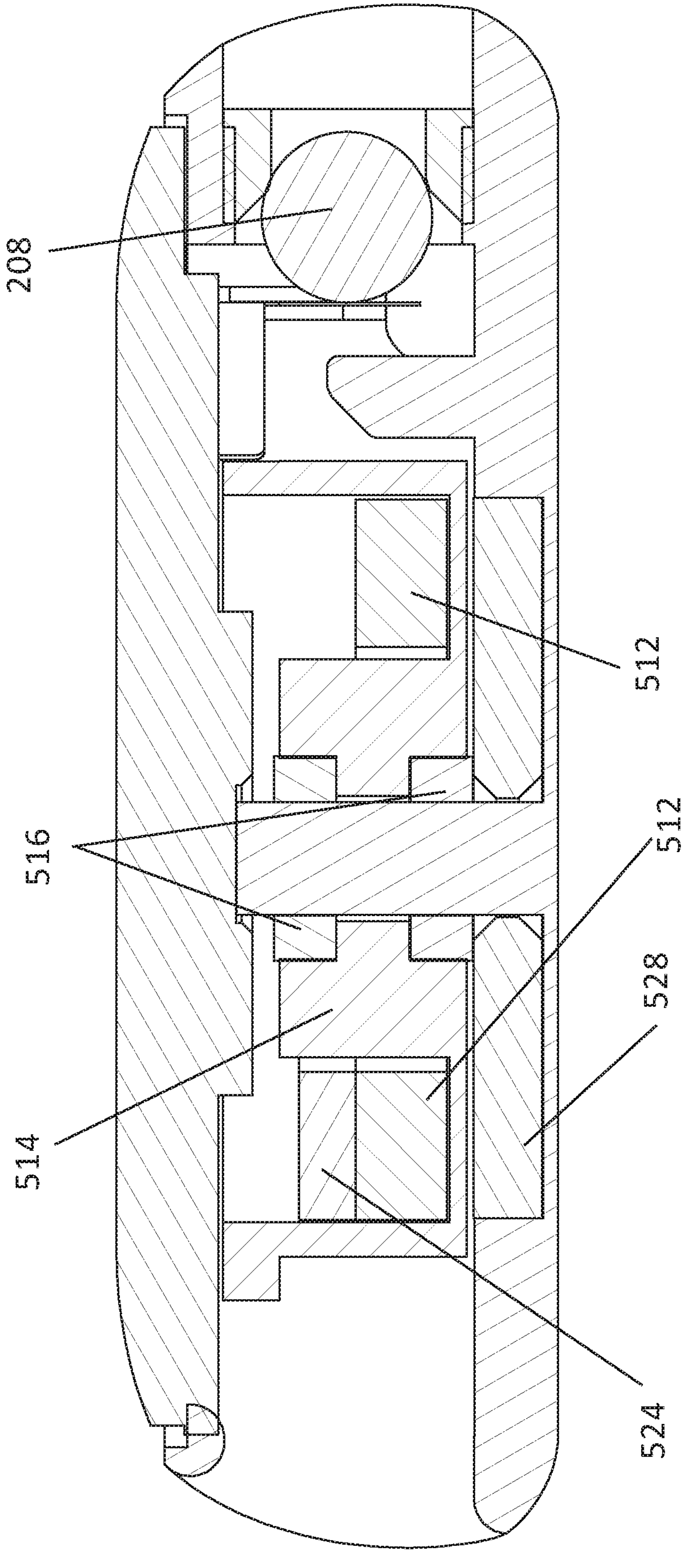
FIG. 4A is a cross-sectional view of one example of the valve of FIGS. 2 and 3A-B taken along line A-A in FIG. 3A.
Figure 4B:
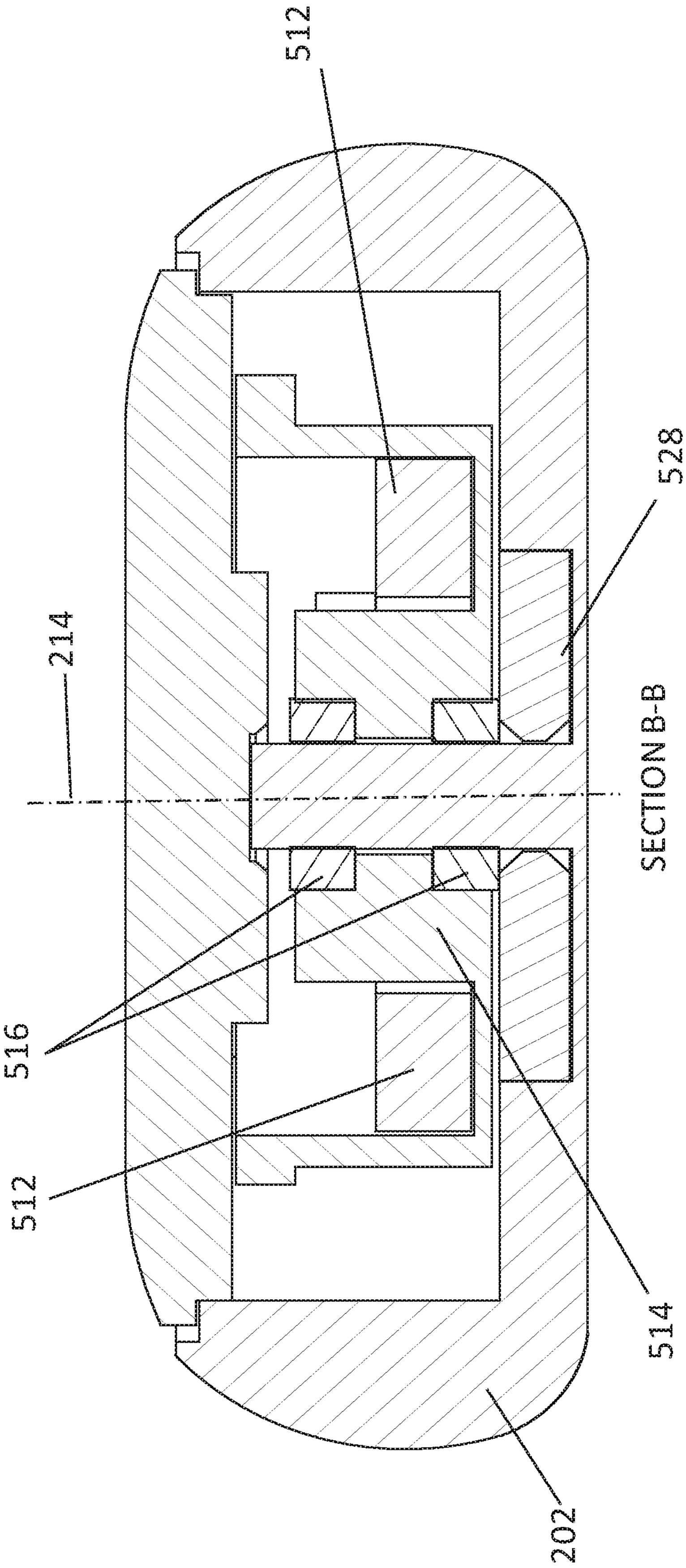
FIG. 4B is a cross-sectional view of the example of the valve of FIGS. 2 and 3A-B taken along line B-B in FIG. 3A.
Figure 4C:
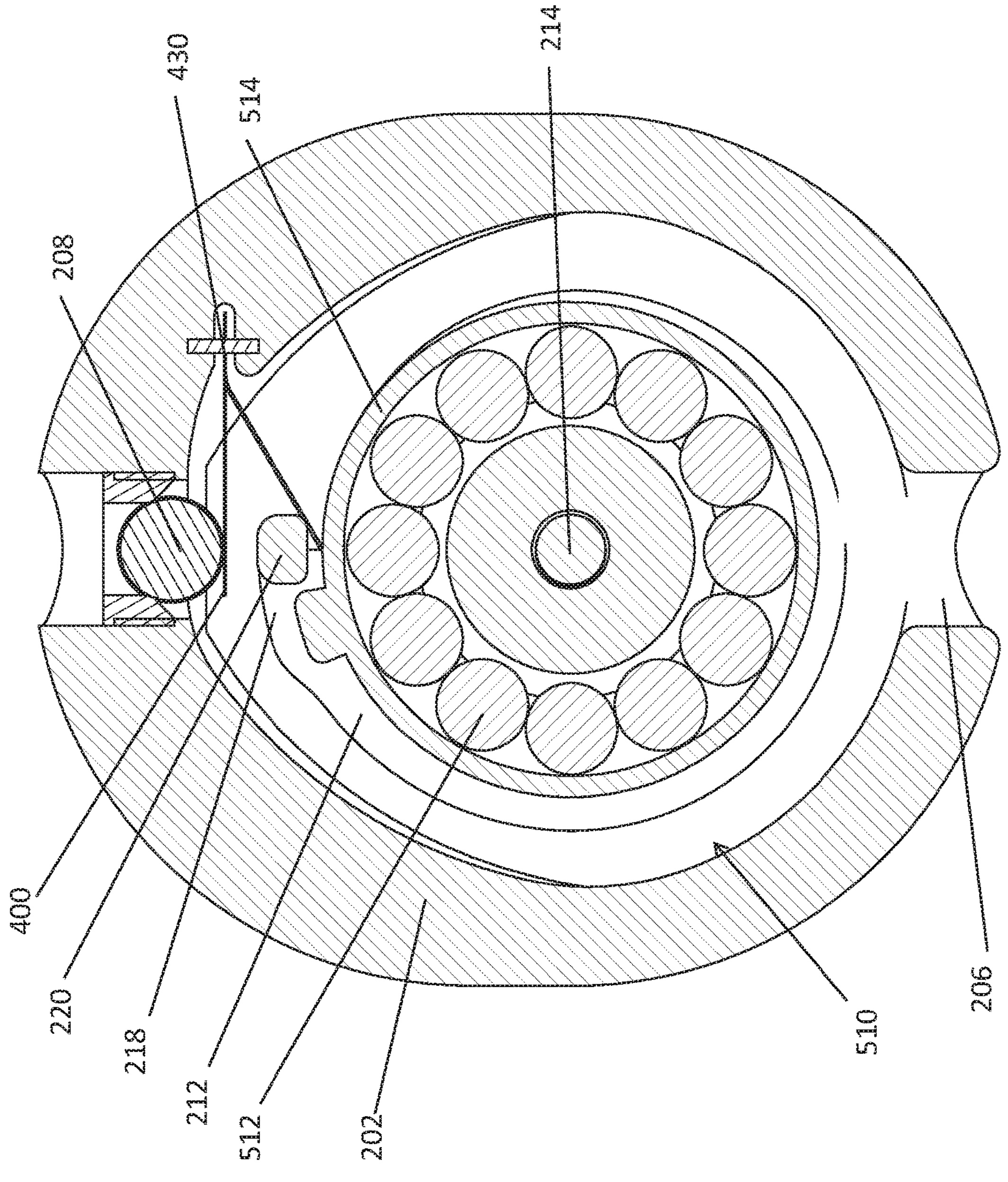
FIG. 4C is a cross-sectional view of the example of the valve of FIGS. 2 and 3A-B taken along line C-C in FIG. 3A.
Figure 5:
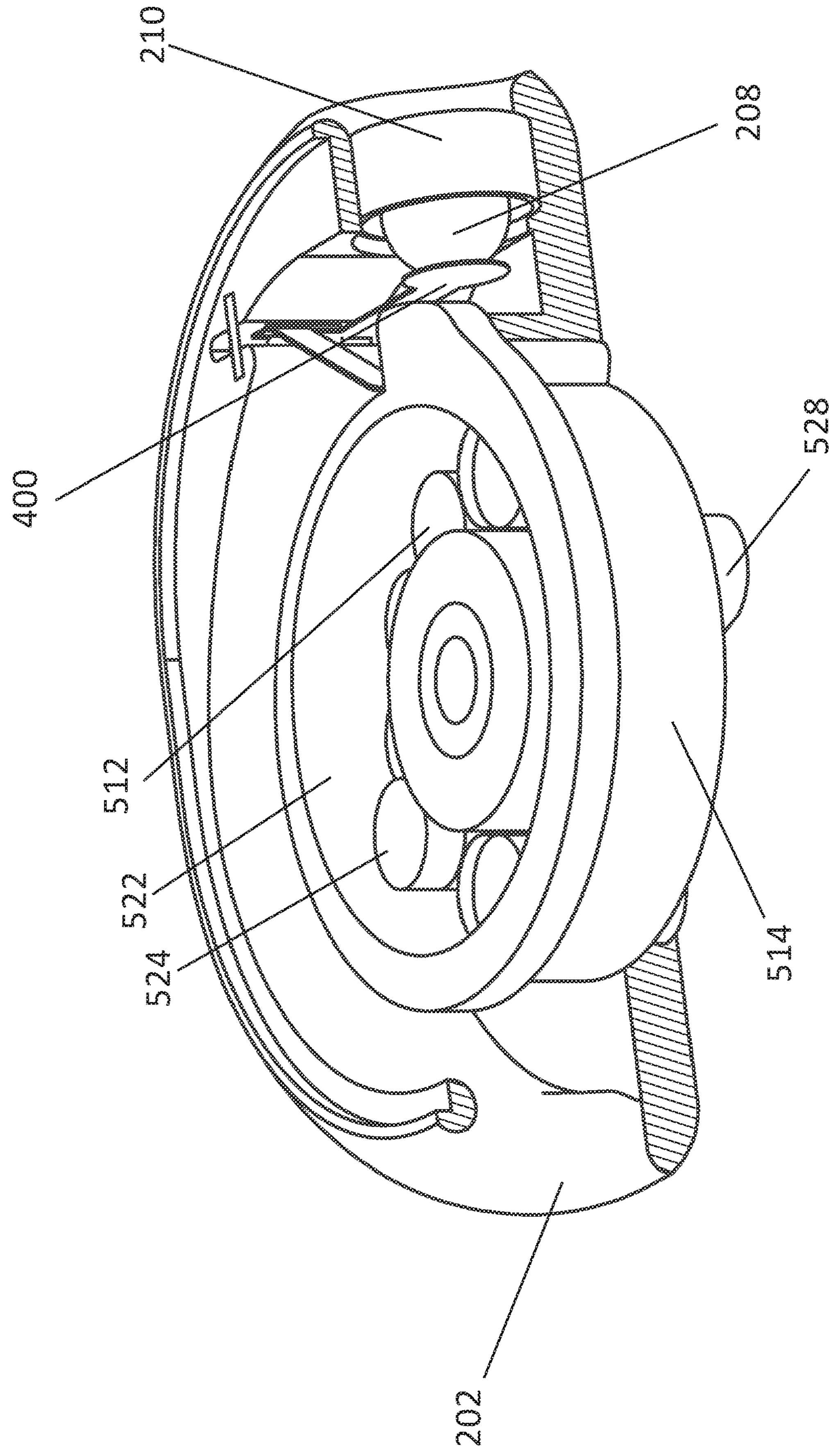
FIG. 5 is a three-dimensional cross-sectional view of an example of the valve of FIGS. 2 and 3A-B, according to aspects of the invention.

Various aspects and features, and operation, of the valve 200, including operation of the magnetic motor, are discussed below with reference to FIGS. 2, 3A-B and 4A-D. FIG. 4A is a cross-sectional view of one example of the valve 200 taken along line A-A in FIG. 3A and showing certain components of the magnetic motor. FIG. 4B is a three-dimensional cross-sectional view of the example of the valve 200 of FIGS. 2 and 3A-B, taken along line B-B in FIG. 3A and showing certain components of the magnetic motor. FIG. 4C is another cross-sectional view of the example of the valve 200 of FIGS. 2 and 3A-B, taken along line C-C in FIG. 3B and showing certain components of the magnetic motor. FIG. 5 is another cross-sectional view of the example of the valve 200 of FIGS. 2 and 3A-B, taken along line A-A in FIG. 3A.

Referring to FIGS. 2, 3A-B, and 4A-C, according to certain embodiments, the valve 200 includes a valve element 208 biased against a valve seat 210 by a spring 400. The spring 400 may comprise, for example, an extension spring, a compression spring, a helical or coiled spring, a torsional spring, a flat spring, a leaf spring, or a cantilever spring. Certain embodiments of the spring 400 are discussed in more detail below.

Fluid enters the valve 200 via the ventricular catheter, for example, and flows through the inlet port 204, which terminates at its casing end at the valve seat 210. The pressure of the fluid (e.g. CSF) pushes against the valve element 208 and the spring 400 in the direction tending to raise the valve element 208 from the valve seat 210. Surfaces of the valve element 208 and valve seat 210 together define an aperture, and the size or diameter of the aperture determines the rate and amount of fluid flow through the valve 200. The valve element 208 preferably has a diameter greater than the valve seat 210 such that when the valve element 208 rests against the valve seat 210, the aperture is substantially closed. The valve element 208 is placed on the inlet side of the aperture and is biased against the circular periphery of the aperture, keeping it closed until the CSF pressure in the inlet chamber exceeds a preselected popping pressure. The term "popping pressure" refers to the opening pressure of the valve and is generally, a slightly higher pressure than the working pressure and is required to overcome inertia when the ball has settled in to the seat. The term "working pressure" can also be referred to as the "operating pressure" and is the pressure of the valve while fluid flows through the valve 200. The closing pressure is the pressure of the valve at which the flow of fluid through the valve stops.

The valve element 208 can be a sphere, a cone, a cylinder, or other suitable shape. In the example illustrated in FIGS. 4C and 5, the valve element 208 is a spherical ball. The spherical ball and/or the valve seat 210 can be made from any appropriate material including, for example, synthetic ruby or sapphire. The valve seat 210 provides a complementary surface, such as a frustoconical surface for a spherical valve element such that, in a closed position of the valve 200, seating of the valve element 208 within the valve seat 210, results in a fluid tight seal. The pressure setting, for example, the opening pressure, of such valves is adjusted by altering the biasing force of the valve element 208 against the valve seat 210. In one example the valve element 208 and valve seat 210 may be press-fit into the housing 202, and, once the initial pressure setting is reached, held in place by the friction. In one example of this configuration, the valve element 208 includes a ruby ball, and the valve seat 210 is also made of ruby.

According to one embodiment, biasing of the spring 400 against the valve element 208 is achieved using a magnetic motor that increases or decreases the working pressure of the valve 200 either continuously or in finite increments. According to certain embodiments, the magnetic motor includes a stator 528 and a rotor 510 that rotates relative to the stator 528 responsive to an external magnetic control field. In one example, the rotor 510 rotates about a central axis of rotation 214. Configuration and operation of embodiments of the magnetic motor are discussed in more detail below.

Referring to FIGS. 2, 4A-C, and 5, according to certain embodiments, the rotor 510 includes a plurality of rotor magnet elements 512 arranged in a rotor casing 514. FIGS. 4C and 5 show the plurality of rotor magnet elements 512 arranged in a circle and disposed within the rotor casing 514. Thus, the rotor casing 514 includes an approximately circular channel 522 in which the rotor magnet elements 512 are contained. In one example, the rotor magnet elements 512 are permanent magnets, each having a south pole and a north pole. The rotor magnet elements 512 are arranged approximately in a circle, as shown in FIG. 4C, with alternating polarity, such that, whether viewed from the top (as in FIG. 4C) or bottom, the south and north poles alternate between every rotor magnet element. Thus, at any one angular position, the pole exposed on the top surface of the element is opposite that of the one exposed on the bottom surface. The rotor magnet elements 512 can be fixedly mounted to the rotor casing 514, which can act as a magnet guide to contain and direct rotation of the rotor magnet elements 512. In FIGS. 2, 4C, and 5, the rotor magnet elements 512 are shown as circular disks; however it is to be appreciated that the rotor magnet elements 512 need not be disk-shaped, and can have any shape, such as, but not limited to, oblong, square, rectangular, hexagonal, free-form, and the like. It is preferable that all the rotor magnet elements 512 are either of approximately the same size or approximately the same magnetic strength even if their size varies to ensure smooth rotation of the rotor 510. According to one embodiment, the rotor 510 includes twelve rotor magnet elements 512 arranged in a circle, as shown in FIG. 4C. According to another embodiment, the rotor 510 includes ten rotor magnet elements 512 arranged in a circle, as discussed further below. In other examples the rotor 510 may include other numbers of rotor magnet elements 512, and embodiments of the programmable valve disclosed herein are not limited to including ten or twelve rotor magnet elements.

According to certain embodiments, in addition to the rotor magnet elements 512, the rotor 510 can further include one or more additional reference magnet elements (also referred to as positioning magnets) 524, as shown in FIGS. 4A and 5. The reference magnet elements 524 can be read by a pressure reader as described herein, or the reference magnet elements 524 can be used as positioning magnets to orient an indicator magnet, such as the indicator magnet 552 discussed below with reference to FIG. 32. The reference magnet element(s) 524 can be placed on top of one or more rotor magnet elements 512, and can be used to allow a doctor, for example, to determine a pressure setting of the valve 200 using an external magnetic sensor, such as a Hall sensor, for example, without requiring X-rays or other imaging techniques, as discussed further below.

The rotor 510 is configured to rotate about the rotor axis 214 responsive to an applied external magnetic field that acts upon the stator 528. The rotor 510 thus can further include bearing rings 516 arranged adjacent an inner circumference of the rotor casing 514, as shown in FIGS. 4A and 4B, to allow rotation of the rotor casing 514. The bearing rings 516 may be made of synthetic ruby, for example. In certain examples the magnetic motor includes two bearing rings 516, namely an upper bearing ring and a lower bearing ring, as shown in FIGS. 4A and 4B. However, in other examples the upper bearing ring may be omitted. In this case, the rotor 510 may tilt on the lower bearing ring 516 as it rotates. In certain examples, this tilting may be advantageous in increasing resistance of the magnetic motor to adjustment by extraneous environmental magnetic fields. In other examples, the lower bearing ring 516 may be made sufficiently wide to avoid any tilting of the rotor 510 as it rotates on the bearing ring.

According to one embodiment, magnetic pulses from an external magnetic field are used to selectively magnetize the stator 528, which acts upon the magnetic rotor and thereby controls movement of the rotor 510. The external magnetic field may be produced, for example, by a magnetic coil or permanent magnet that is placed in proximity to the valve assembly, as discussed in more detail below. The stator 528 can be made of a soft magnetic material that can be selectively magnetized, and the magnetic polarity of which can be selectively controlled, by the application of the external magnetic field. For example, the stator 528 can be made of a Nickel-Iron alloy, for example, having approximately 72-83% Nickel. By controlling the magnetization and magnetic polarity of the stator 528, the rotor 510 can be made to rotate in a controlled manner as the rotor magnet elements 512 respond to the changing magnetization and magnetic polarity of the stator 528, as discussed further below.

The valve 200 is configured such that rotation of the rotor 510 controls the spring 400 to adjust the biasing of the valve element 208 against the valve seat 210, thereby adjusting the size of the aperture and controlling the flow of fluid through the valve 200. In one embodiment, the valve 200 includes a cam 212, which engages the spring 400, as shown in FIGS. 2, 4C, and 5. In the illustrated example, the cam 212 is integrated with the rotor casing 514, thereby avoiding the need for a separate cam element. In other embodiments; however, the cam can be coupled to the rotor 510 and positioned in contact with the spring 400 such that rotation of the rotor 510 causes movement of the cam 212 which, in turn, adjusts the tension of the spring 400 against the valve element 208. For example, the cam 212 could be attached to the rotor casing 514 via a central shaft 520, such that the rotor casing 514 and the cam 212 can rotate together about the central axis 214. As used herein the term "cam" refers either to a separate cam element that can be attached to the rotor or to the rotor casing 514 acting as a cam, as in the illustrated examples in which the cam is integrated with the rotor casing.

For certain applications of the valve assembly 100, such as the treatment of hydrocephalus, for example, the pressure range of the valve may be approximately 0-200 mm $H_2O$ or 0-400 mm $H_2O$, for example, which are very low pressure ranges. Furthermore, it may be desirable to make small pressure changes within the range. However, it may not be practicable (due to manufacturing constraints, etc.) to produce a valve assembly in which the cam 212 is capable of making very minute movements, for example, on the order of a few micrometers. Therefore, in order to accommodate the low-pressure range and small incremental changes in pressure, a very soft spring may be required. Conventionally, in order to obtain a sufficiently soft spring, the spring 400 would be very long. However, accommodating a very long, soft spring inside an implantable housing may pose challenges. Accordingly, aspects and embodiments are directed to spring configurations that produce a lever or "gear reduction" effect, such that reasonable (i.e., within standard manufacturing capabilities) movements of the cam 212 may be translated into very small adjustments in low-pressure settings. In particular, certain embodiments include a cantilever spring configuration, as shown in FIG. 6A, for example.

Figure 6A:
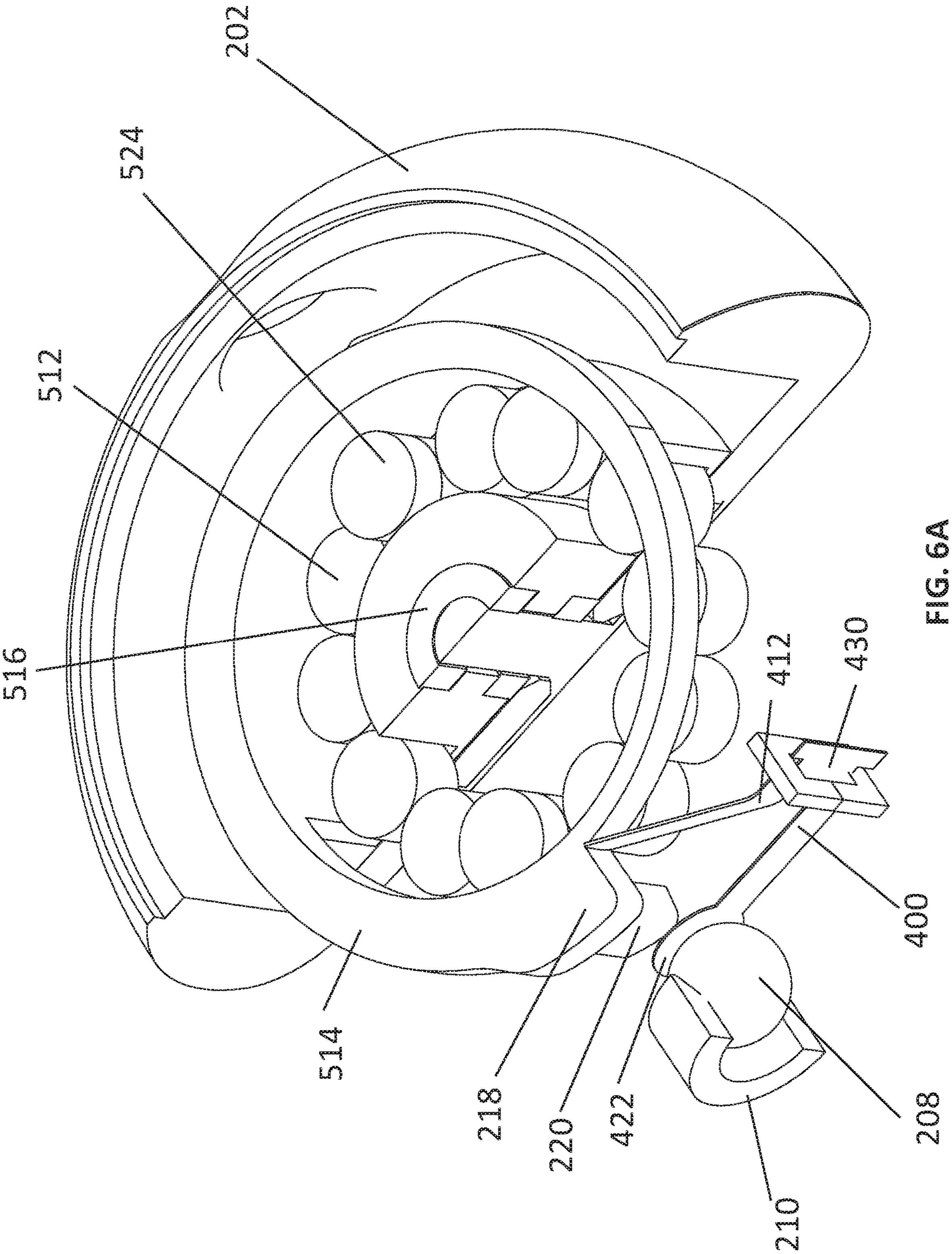
FIG. 6A is a diagram showing an enlarged view of a portion of the valve of FIG. 5, with the cam shown in a position of minimum tension against the biasing spring, according to aspects of the invention.
Figure 6B:
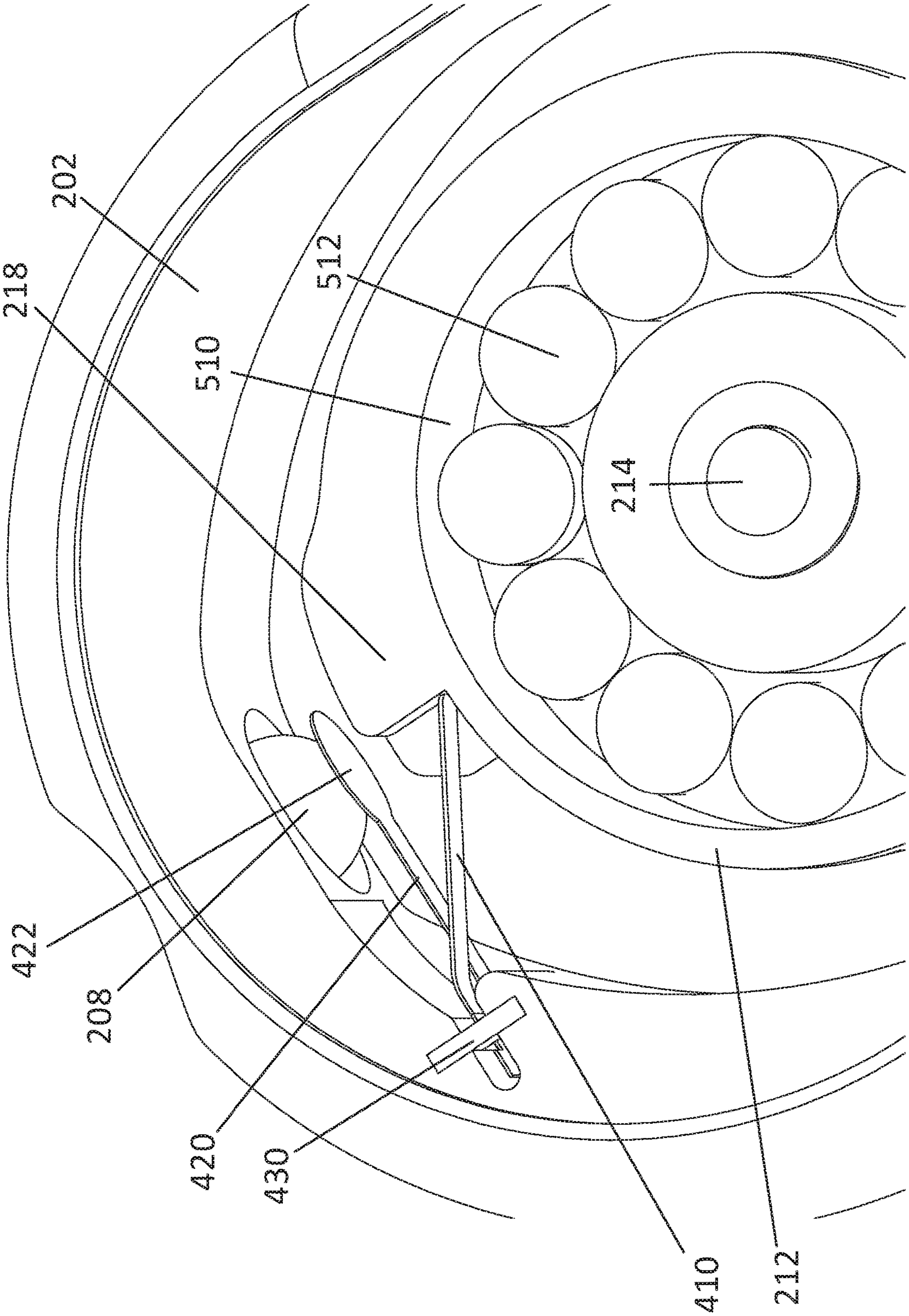
FIG. 6B is a diagram showing another view of a portion of the valve of FIG. 5, with the cam shown in a position of minimum tension against the biasing spring, according to aspects of the invention.
Figure 6C:
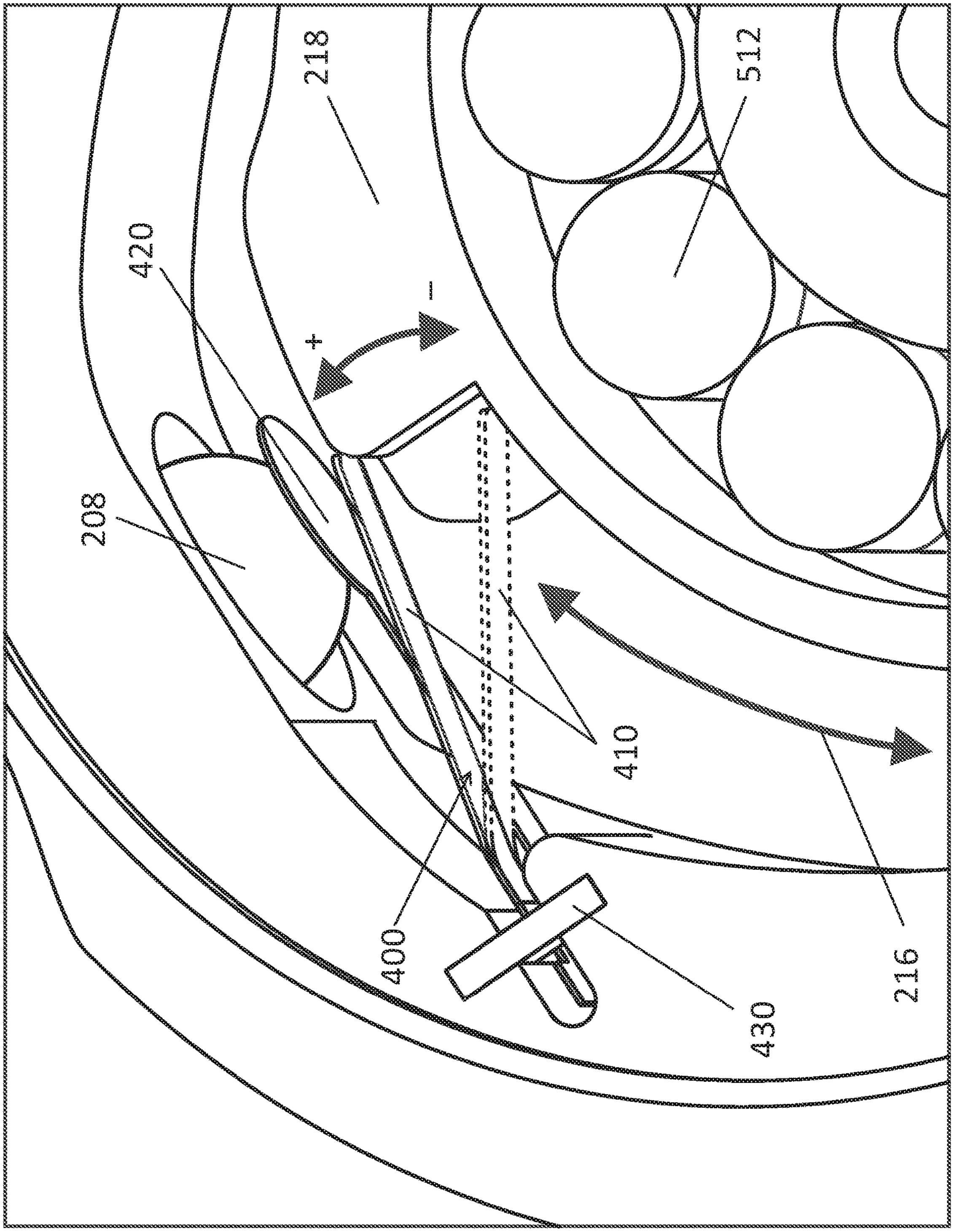
FIG. 6C is a diagram showing an enlarged view of a portion of the valve of FIG. 5, with the cam shown in a position of maximum tension against the biasing spring, according to aspects of the invention.
Figure 6D:
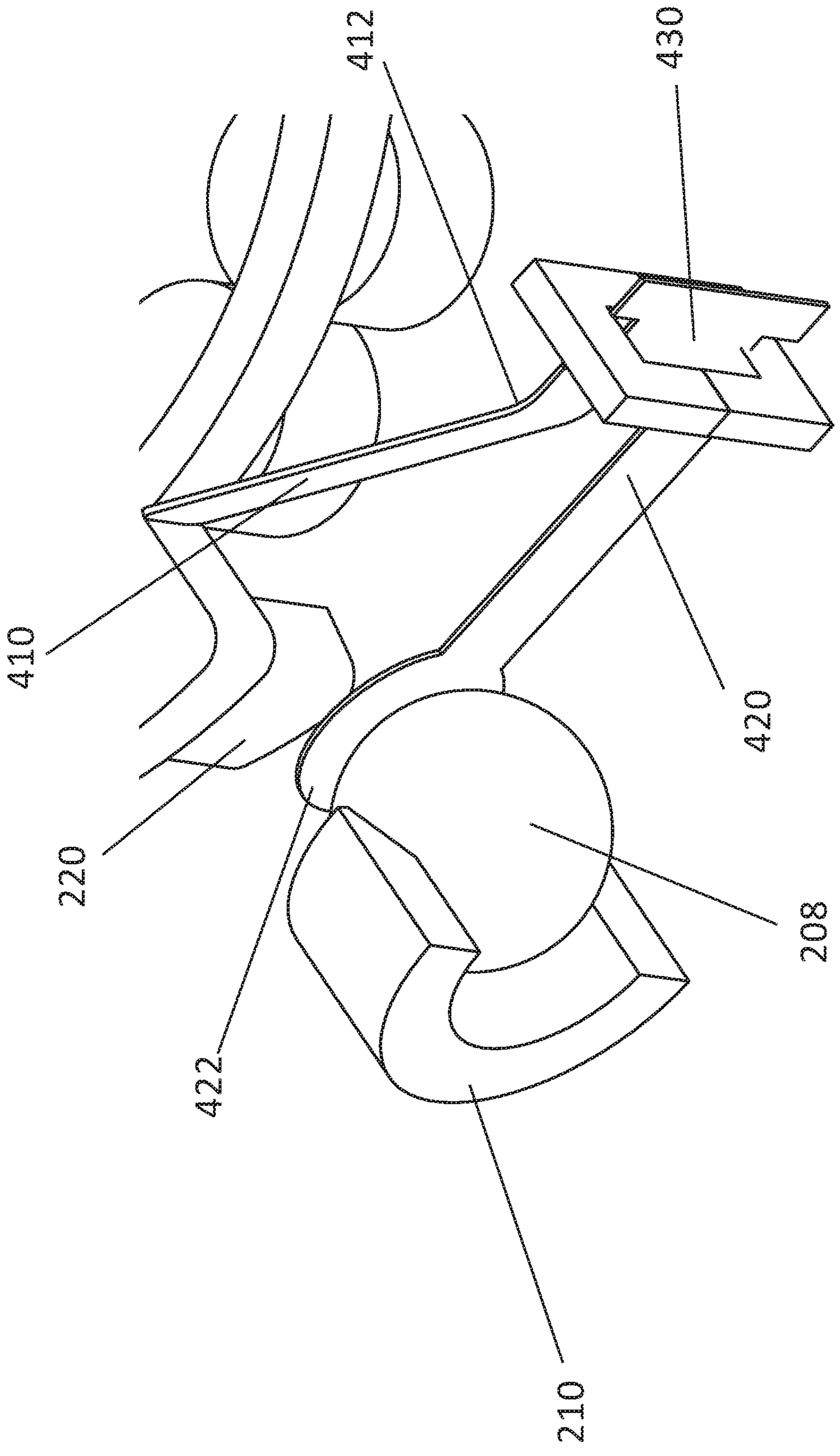
FIG. 6D is a diagram showing an enlarged view of a portion of the valve of FIG. 5, showing an example of the spring biased against the valve element and the cam, according to aspects of the invention.

FIGS. 6A, 6B, 6C, and 6D illustrate views of the portions of the programmable valve 200, showing the cam 212 and the spring 400 biased against the valve element 208. FIGS. 6A and 6B show the cam 212 in the position of minimum tension against the biasing spring 400, and FIG. 6C shows the cam 212 in the position of maximum tension against the biasing spring 400. FIG. 6D shows an enlarged view of one example of the spring 400. In FIG. 6D the spring 400 is shown with the valve element 208 seated in the valve seat 210. In this example the spring 400 is a cantilever spring and includes a first spring arm 410 that is in direct or indirect contact with the cam 212, and a cantilevered arm 420 that is biased against the valve element 208. Both the first spring arm 410 and the cantilevered arm 420 extend in the same direction from a fulcrum 430 (or fixed attachment point of the spring 400). Thus, the cantilevered arm 420 has a fixed end at the fulcrum 430 and a free end 422 that rests against the valve element 208, as shown in FIGS. 6A and 6C. Similarly, the first spring arm 410 has a fixed end at the fulcrum 430 and a free end that engages the cam 212. In certain examples the cantilevered arm 420 may be longer than the spring arm 410. In the illustrated example the spring arm 410 is "bent", including an inflection point 412. This configuration allows for a reduction in the overall size of the spring 400 relative to examples in which the first spring arm is straight. Rotation of the cam 212 causes pressure against the spring arm 410 in contact with the cam, changing the tension in the spring 400. That pressure is spread and reduced through the spring structure, such that resulting pressure applied against the valve element 208 by the cantilevered arm 420 can be very low, and in particular, can be within a desired range (e.g., 0-200 mm $H_2O$, as mentioned above), without placing difficult or impracticable constraints on the rotational movement of the cam 212. By appropriately selecting the relative lengths of the two arms 410 and 420, and the widths of each arm, the equivalent of a lever or gear reduction mechanism may be achieved. Thus, a sufficiently soft spring to provide the low pressures (e.g., 0-200 mm H2O) needed for certain applications may be achieved using a short, two-armed spring 400, rather than a conventional long spring.

Figure 7A:
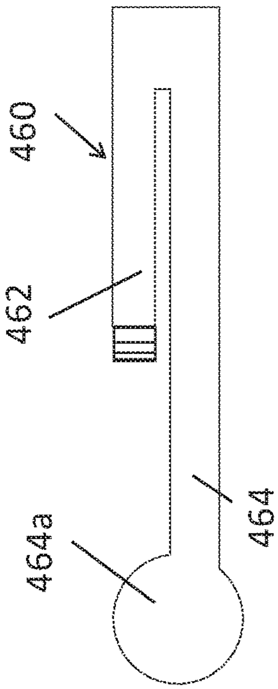
FIG. 7A is a diagram showing an example of a flat spring according to aspects of the present invention.
Figure 7B:
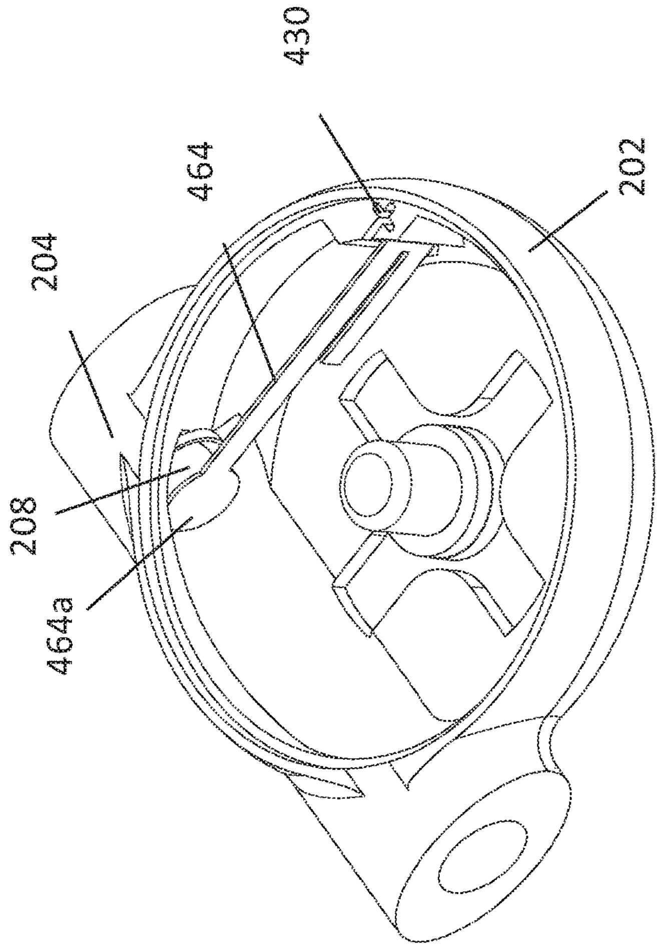
FIG. 7B is a partial perspective view showing an example of the flat spring of FIG. 7A installed in a valve according to aspects of the present invention.

The spring 400 can have a variety of different shapes and configurations, not limited to the example shown in FIGS. 6A-D. For example, FIG. 7A and FIG. 7B show a flat spring 460. FIG. 7A shows the flat spring alone, and FIG. 7B shows the spring installed in a valve and biased against the valve element 208. The flat spring 460 includes a first spring arm 462 that is in direct or indirect contact with the cam 212 and a cantilevered arm 464 that is biased against the valve element 208. In this example, the cantilevered arm 464 includes a rounded end portion 464*a* that rests against the valve element 208. Both the first spring arm 462 and the cantilevered arm 464 are flat and extend from a fulcrum 430. The cam 212 is not shown in FIG. 7B.

Figure 8A:
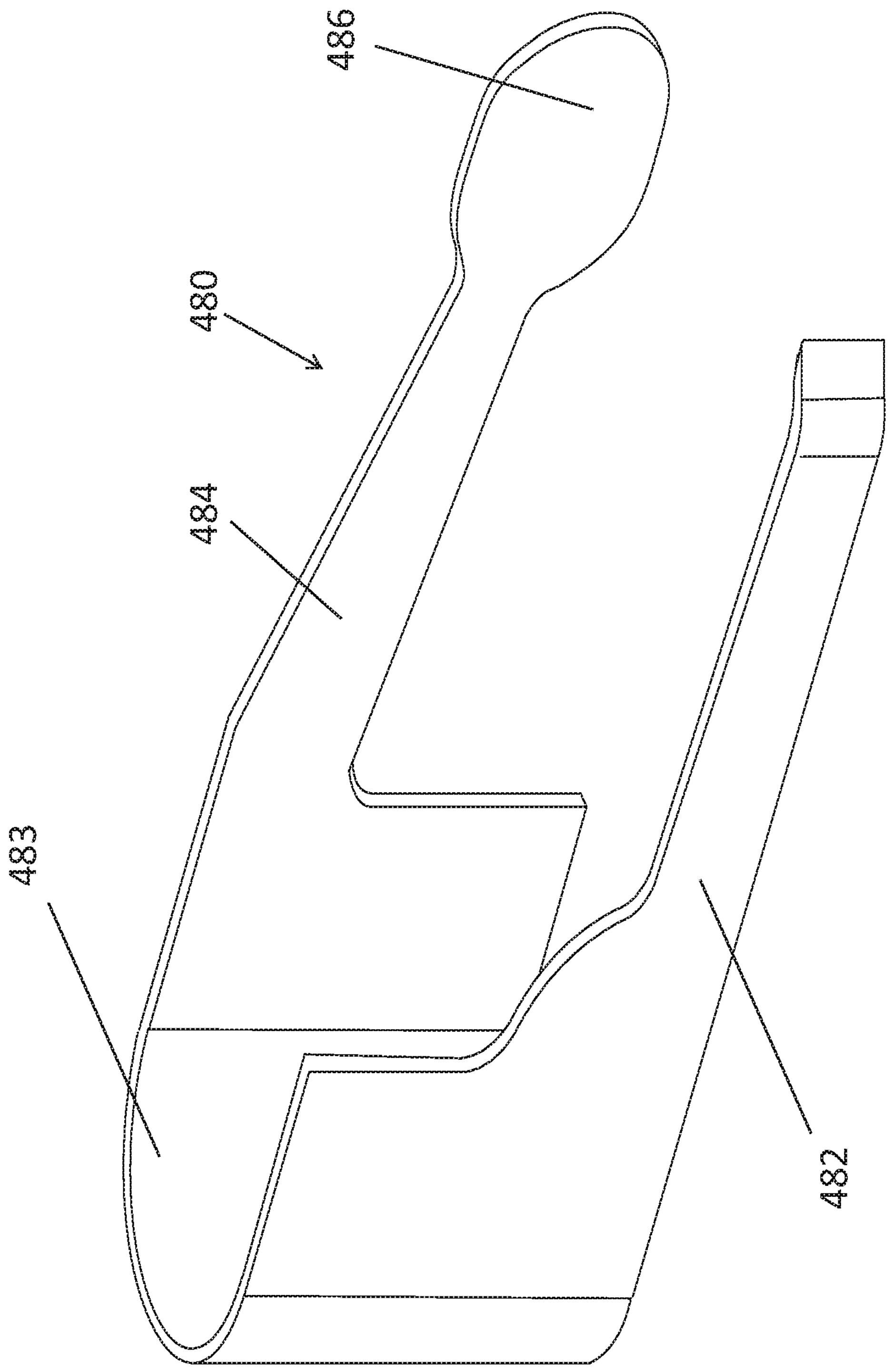
FIG. 8A is a diagram showing an example of a u-shaped spring according to aspects of the present invention.
Figure 8B:
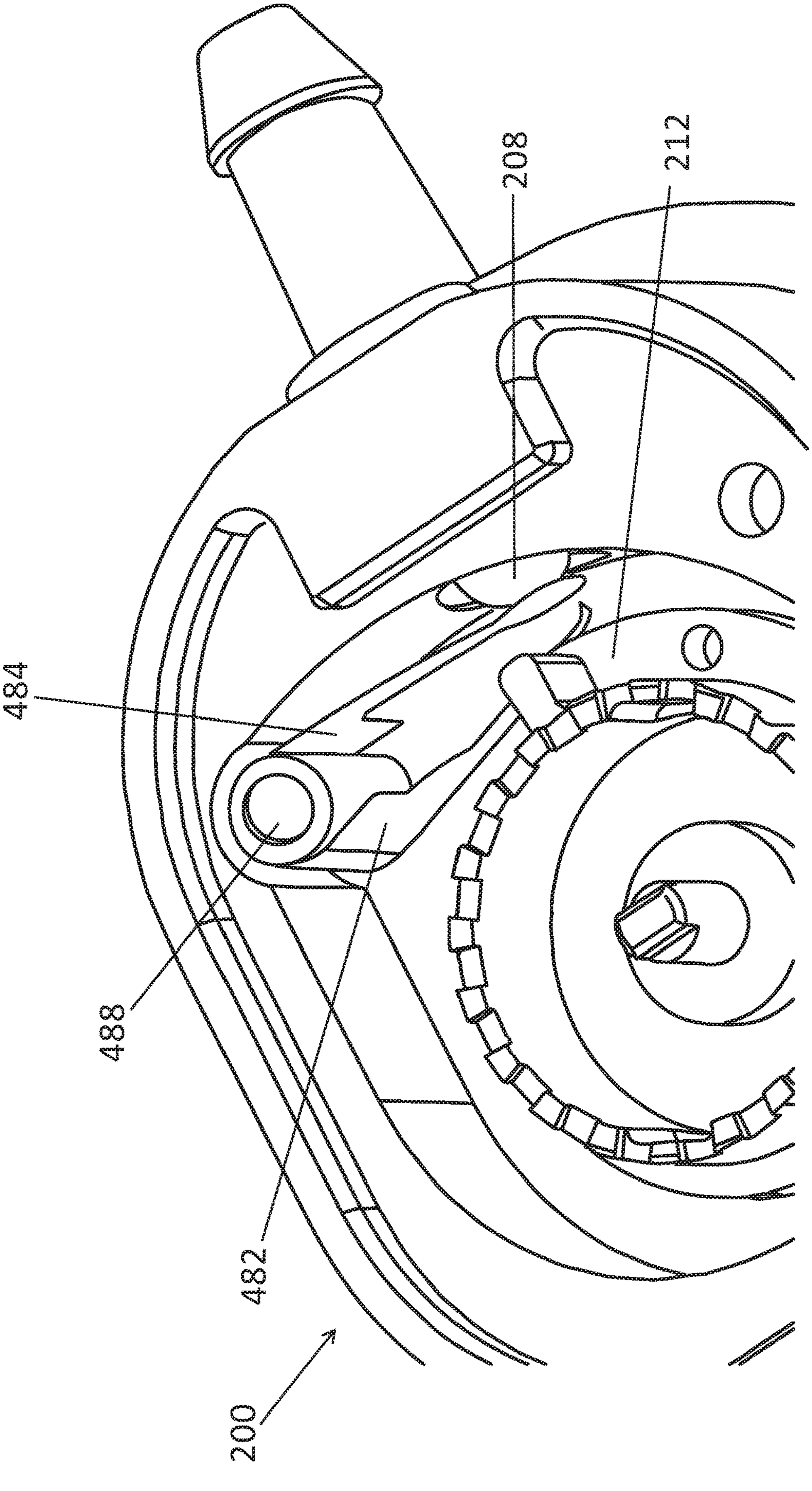
FIG. 8B is a diagram showing the u-shaped spring of FIG. 8A installed in a programmable valve, according to aspects of the present invention.

FIGS. 8A and 8B show an example of a u-shaped cantilevered spring 480. FIG. 8A shows the u-shaped spring 480 alone. FIG. 8B is a sectional view of a portion of an example of the programmable valve 200 showing the u-shaped spring 480 installed in the valve 200. The u-shaped spring 480 includes a first spring arm 482 that is in direct or indirect contact with the cam 212 and a cantilevered arm 484 that is biased against the valve element 208. The cantilevered arm 484 has a free end 486 that rests against the valve element 208. The first spring arm 482 and the cantilevered arm 484 are connected by a u-shaped portion 483 that is supported by a post 488. In some embodiments, the u-shaped portion 483 is spring biased around the post 488 so the u-shaped portion 483 frictionally engages the post 488.

Figure 8C:
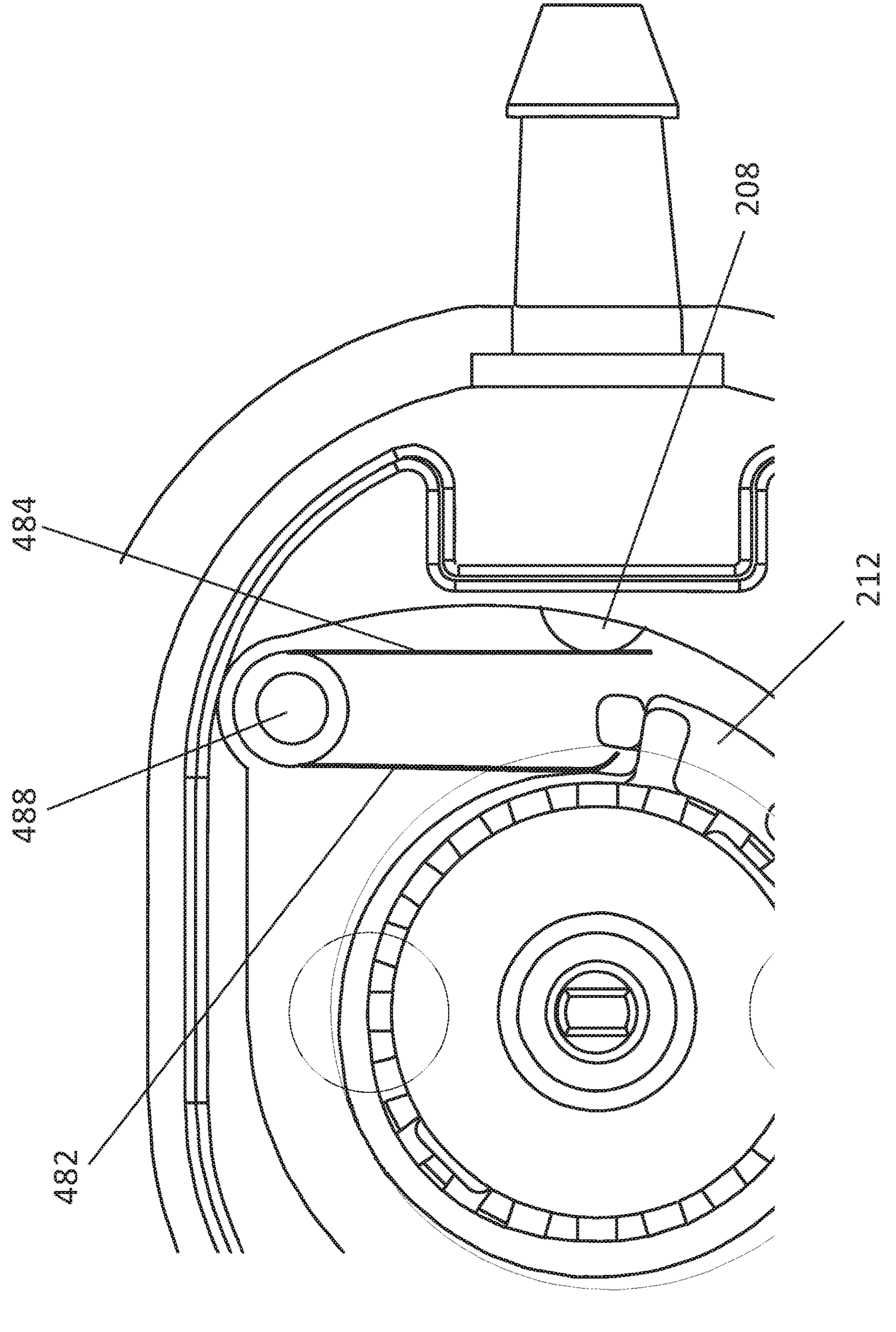
FIG. 8C is a diagram showing a portion of the programmable valve of FIG. 8B when the programmable valve is set at the lowest pressure setting.
Figure 8D:
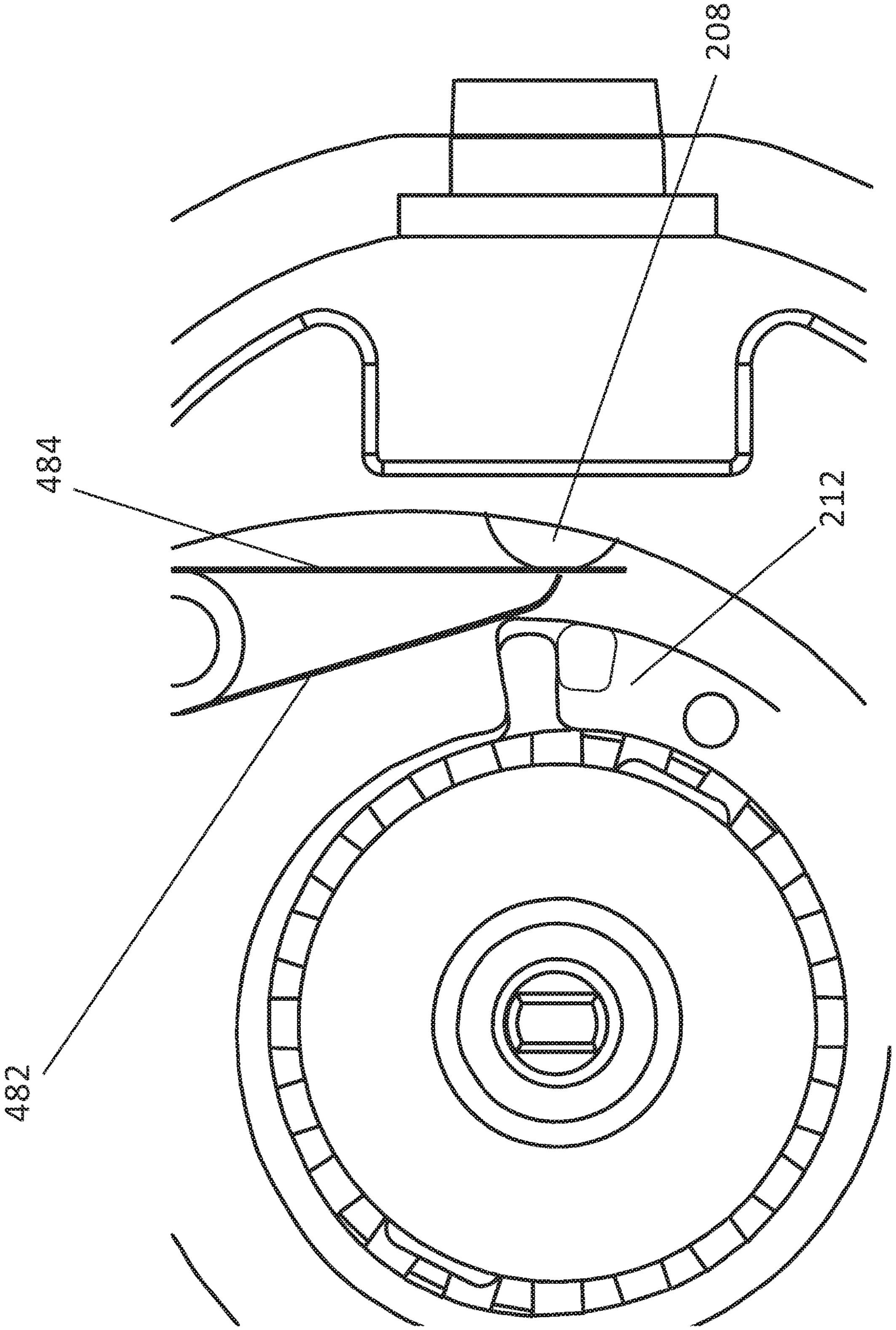
FIG. 8D is a diagram showing a portion of the programmable valve of FIG. 8B when the programmable valve is set at the highest pressure setting.

Similar to FIGS. 6B and 6C discussed above, FIGS. 8C and 8D show examples of the u-shaped spring 480 positioned corresponding to different pressure settings of the programmable valve 200. FIG. 8C shows the u-shaped spring 480 when the cam 212 is oriented such that the programmable valve 200 is set at the lowest pressure setting. FIG. 8D shows the u-shaped spring 480 when the cam 212 is oriented such that the programmable valve 200 is set at the highest pressure setting.

Figure 9A:
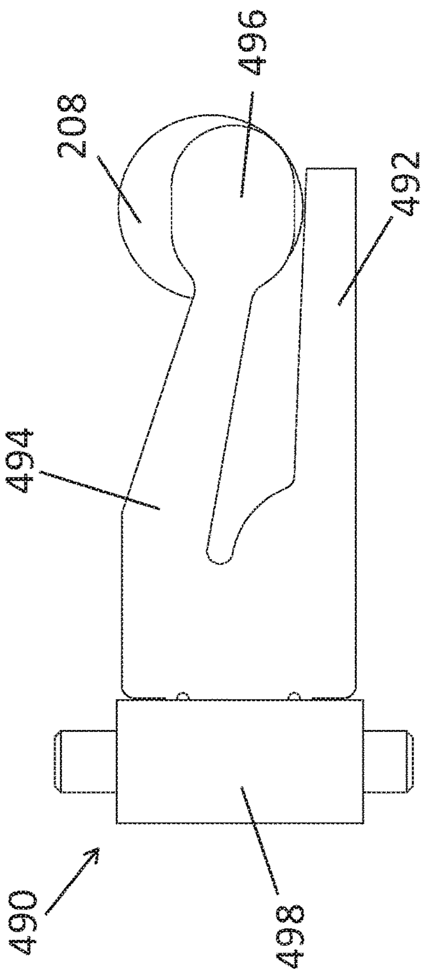
FIG. 9A is a diagram illustrating another example of a spring according to aspects of the present invention.
Figure 9B:
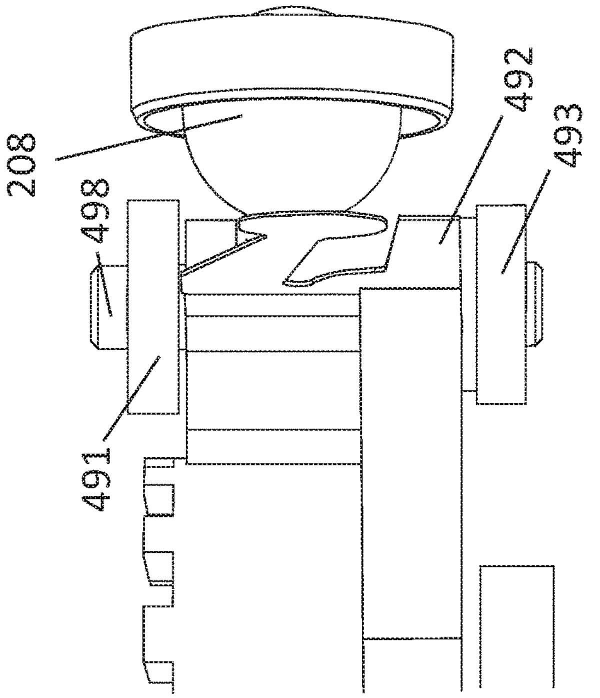
FIG. 9B is a diagram showing the spring of FIG. 9A engaging a valve element, according to aspects of the present invention.

FIG. 9A shows another example of a cantilevered spring 490 having a first spring arm 492 that is configured to be in direct or indirect contact with the cam 212 and a cantilevered spring arm 494 that is biased against the valve element 208. The cantilevered spring arm 494 has a free end 496 that rests against the valve element 208. In this example, the first spring arm 492 and the cantilevered spring arm 494 are secured to a post 498, for example, by welding. FIG. 9B shows an example of the spring 490 of FIG. 9A in a programmable valve 200. The post 498 is configured to rotate on two ruby bearings 491 and 493. One ruby bearing 491 is positioned at an upper portion of the post 498 and the second ruby bearing 493 is positioned at a lower portion of the post 498. The ruby bearings 491, 493 allow the post 498 to pivot with respect to the valve body 202.

As will be appreciated by those skilled in the art, given the benefit of this disclosure, the spring 400 may have other configurations in addition to those described above and shown in the drawings.

In certain examples as the cam 212 rotates, the force exerted against the spring 400 is adjusted in fine increments or continuously over a range from minimum force to maximum force. As shown in FIG. 6C, when the cam 212 is in the position in which the maximum pressure is exerted by the cam 212 against the spring 400, the cantilevered arm 420 is moved toward the valve element 208. Thus, the pressure setting of the valve 200 is highest for this position of the cam 212. In one example, pressure exerted by the cam 212 against the spring 400, and therefore the tension in the spring 400, increases with clockwise rotation of the cam 212, as indicated by arrow 216. However, those skilled in the art will appreciate, given the benefit of this disclosure, that the rotor 510, cam 212, and spring 400 may alternatively be configured such that counter-clockwise rotation of the rotor 510 increases the tension in the spring 400.

As described above, the valve element 208 and valve seat 210 form an aperture through which the fluid flows. The inlet port 204 can be oriented such that fluid enters the aperture (or, in other words, pushes against the valve element) in a direction perpendicular to a central axis of the rotor 510. The inlet port 204 can also be oriented such that fluid enters the aperture (or pushes against the valve element) in a direction that is perpendicular to the central axis 214 of the rotor 510. In certain aspects, when the inlet port 204 is oriented such that fluid enters the aperture in a direction perpendicular to the central axis 214 of the rotor 510, the cam 212 directly or indirectly produces horizontal displacement of the spring 400, as shown in FIGS. 6A and 6B, for example.

The cam 212 in embodiments of the valve assembly 100 disclosed herein, in any configuration, can have a constant or linear slope, a piecewise linear slope, a non-linear slope and combinations of such slopes in the surface(s) that engage the spring 400. If the cam 212 has a linear slope, rotation of the cam 212 increases or decreases the pressure setting in a linear way. If the cam 212 has a non-linear slope, the pressure, for example, can increase more towards the end of the rotation. This allows the possibility of having minute increments of pressure initially, for example, between 0 and 200 mm $H_2O$, and larger increments of pressure thereafter. For example, the cam 212 illustrated in FIGS. 6A and 6B includes a surface with a non-linear slope that engages the first arm 410 of the spring 400. Specifically, the cam 212 includes a projection 218, which alters the rate of increase in the pressure exerted by the cam 212 on the spring 400 as the cam 212 rotates. Thus, in certain examples the force exerted by the cam 212 on the spring 400 increases in a substantially linear manner over the majority of the rotational cycle of the cam 212; however, toward the end of the cycle, the force increases more dramatically due to the influence of the projection 218.

In certain applications, for example, in the treatment of hydrocephalus in children, it may be desirable to be able to determine whether or not the patient is still in need of the valve after some time of use or whether hydrocephalus has become arrested and is no longer in need of shunting. For example, depending on the cause of hydrocephalus, after several years of using an implanted shunt valve assembly 100, the patient may no longer need the valve. One method of testing to determine whether or not the valve is still needed in the patient is to significantly increase the pressure of the spring 400 against the valve element 208, thereby almost completely closing the valve 200, and observe the patient's condition thereafter. Accordingly, the above-described configuration in which the step pressure increase is significantly larger at or close to the maximum pressure position of the spring 400 and cam 212 may advantageously allow this testing to be performed. If the patient's condition deteriorates after the pressure setting of the valve 200 is significantly increased, the pressure setting may simply be decreased again, by rotating the cam 212. Thus, this configuration provides a safe quasi-OFF setting for the valve 200, without having the valve 200 completely closed or removed.

According to certain examples the magnetic motor may include a rotor stop or cam stop 220 that prevents 360 degree rotation of the cam 212, and thereby prevents the valve from being able to transition immediately from fully open to fully closed, or vice versa, in one step. The cam 212 can rotate either clockwise or anticlockwise up to the position set by the cam stop 220, and then must rotate in the opposite direction. Thus, a full rotation of the cam 212 is required to transition the valve from fully open to fully closed, or vice versa, rather than only a small step or incremental rotation.

In certain examples, after the valve assembly 100 is manufactured, a calibration device is typically needed to adjust the pressure settings. For example, in certain embodiments the spring 400 may be constructed such that it is linear with respect to each step, that is, with each step of rotation of the cam 212, the spring 400 is tensioned so that the pressure of the valve 200 goes up by X amount, and this is true for each additional step of rotation. Accordingly, it may be necessary to calibrate the device to set the cam 212 at a given position and pre-tension the spring 400 to an appropriate pressure for that position. Therefore, after the valve 200 is assembled and during the calibration, there may be a flow of nitrogen (or some other fluid) through the valve assembly.

Figure 10A:
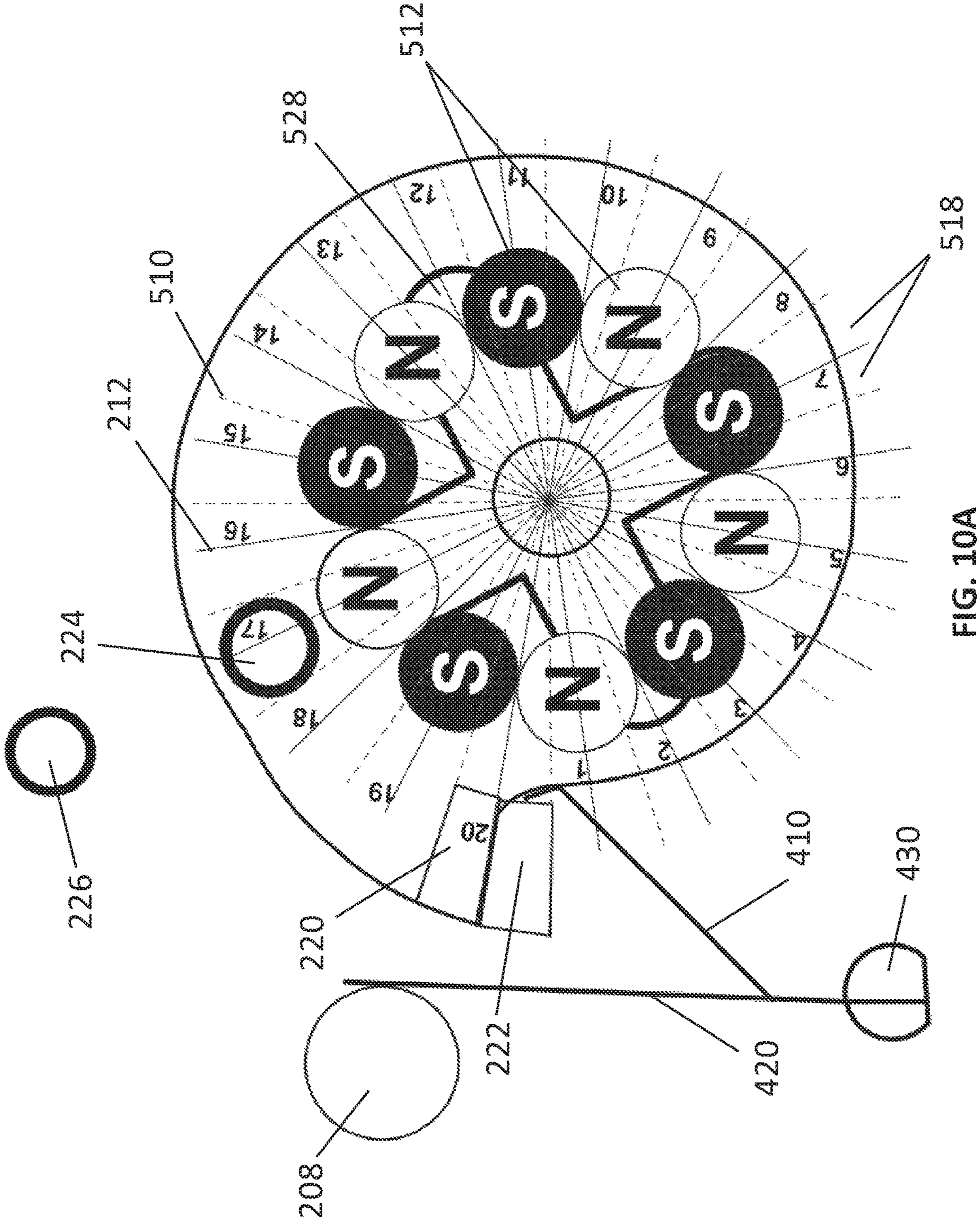
FIG. 10A is a schematic diagram of one example of a rotor for use in embodiments of a magnetically-operable implantable valve according to aspects of the present invention, showing the rotor positioned for a minimum pressure setting of the valve.
Figure 10B:
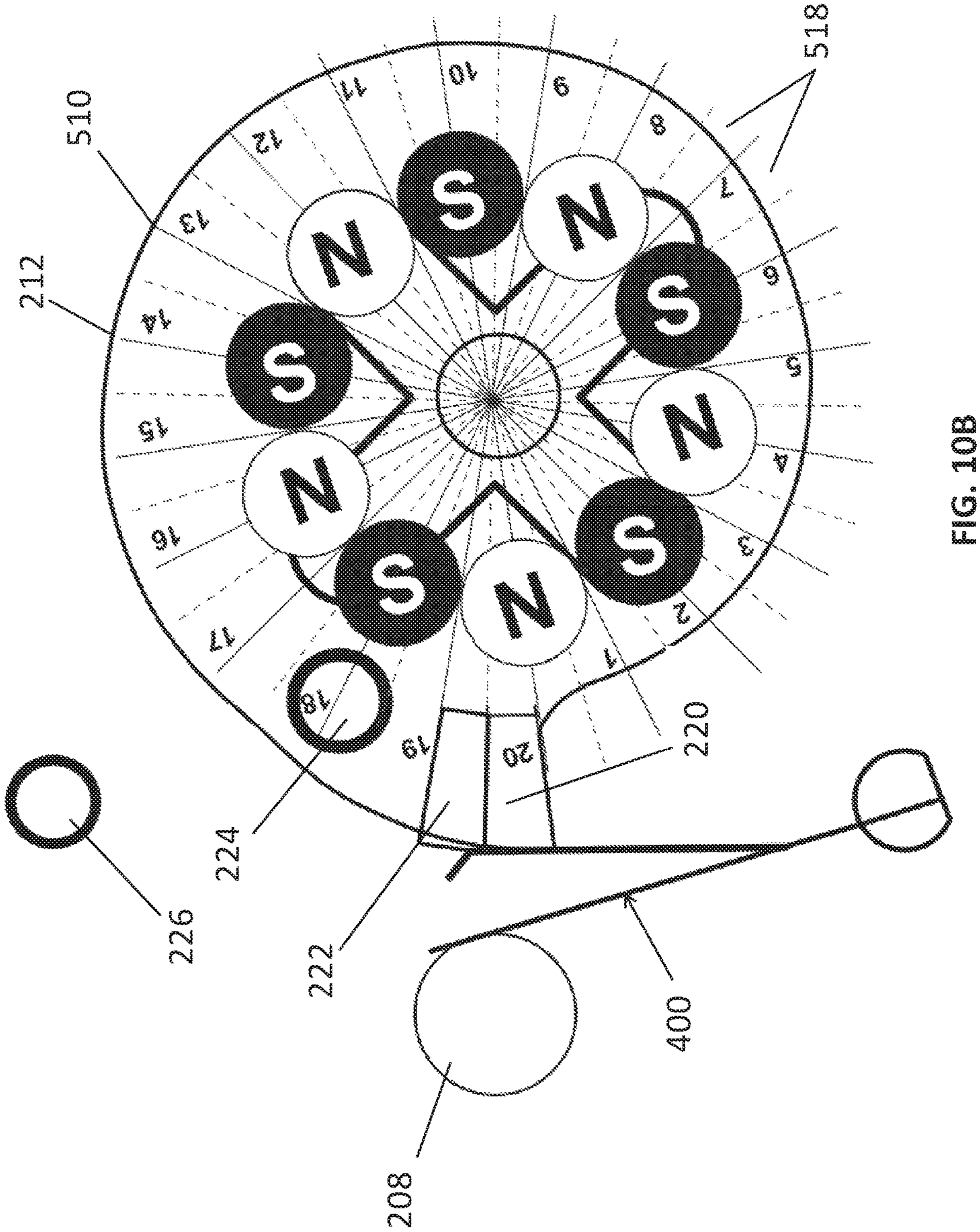
FIG. 10B is a schematic diagram of the rotor of FIG. 10A showing the rotor positioned for a maximum pressure setting of the valve.

FIGS. 10A and 10B schematically illustrate an example of the magnetic rotor 510 including ten rotor magnet elements 512 arranged in a circle, as discussed above, and configured such that clockwise rotation increases the pressure setting of the programmable valve 200. FIG. 10A shows the rotor 510 and the spring 400 in the position of minimum tension on the spring, corresponding to a lowest pressure setting of the valve 200. FIG. 10B shows the rotor 510 and the spring 400 after clockwise rotation from position shown in FIG. 10A into the position of maximum tension on the spring, corresponding to a highest pressure setting of the valve 200. As discussed above, the rotor 510 may rotate through a plurality of incremental steps, indicated at 518, each step corresponding to a defined change in the pressure setting of the valve 200. As also discussed above, the rotor 510 may include the cam stop 220 which may prevent 360 degree rotation of the cam 212, and thereby prevents the valve from being able to transition immediately from fully open to fully closed, or vice versa, in one step. In one example, schematically illustrated in FIGS. 10A and 10B, at the maximum and minimum pressure settings of the valve 200, the cam stop 220 abuts a housing stop 222. The cam stop 220 and housing stop 222 are sized and arranged such that the cam stop cannot pass the housing stop, thereby preventing further rotation of the cam in the same direction. Accordingly, when the rotor 510 is in the position of the minimum pressure setting of the valve 200 (FIG. 10A), the rotor must rotate clockwise, thereby gradually increasing the pressure setting of the valve. Counter-clockwise rotation, which would transition the valve 200 from the minimum pressure setting to the maximum pressure setting in one step is prevented by the cam stop 220 and housing stop 222. Similarly, when the rotor 510 reaches the position corresponding to the maximum pressure setting of the valve 200 (FIG. 10B), further clockwise rotation of the cam is prevented by cam stop 220 and the housing stop 222, such that the rotor must rotate counter-clockwise, thereby gradually decreasing the pressure setting of the valve.

As also shown schematically in FIGS. 10A and 10B, in certain examples the valve 200 may include a pair of radiopaque markers, namely a rotor marker 224 and a housing marker 226, that can be seen in an X-ray and indicate the position of the rotor 510, and therefore the pressure setting of the valve 200. In one example the pair of radiopaque markers 224 and 226 are localized in such a way that at the lowest pressure setting of the valve, the two markers are aligned with the center of the cam, as shown in FIG. 10A. The housing marker 226 is fixed in the housing of the valve 200 and does not rotate with the rotor 510, whereas the rotor marker 224 rotates with the cam/rotor.

In some embodiments, the radiopaque markers 224, 226 include tantalum. In some embodiments, the radiopaque markers 224, 226 include tantalum spheres and/or tantalum beads.

As discussed above, because embodiments of the valve assembly 100 comprise a magnetically actuated rotor 510, the pressure setting of the implanted programmable valve 200 can be adjusted by positioning an external adjustment device (also referred to herein as a valve programmer) in proximity to the implanted valve 200 but external to the body. The valve programmer includes a magnetic field generator, along with various control and input/output (I/O) components to allow a user (e.g., a doctor) to control the valve programmer to set and optionally read the pressure setting of the implanted programmable valve 200. In certain embodiments, the magnetic field generator can include an arrangement of electromagnets, as discussed below with reference to FIGS. 11A, 13, 15, 16A-H, 17, and 18A-H. In other embodiments, the magnetic field generator can include one or more permanent magnets, and the valve programmer can be battery operated, as discussed further below with reference to FIGS. 11B, 11C, 19-22, 23A-E, and 24.

Figure 11A:
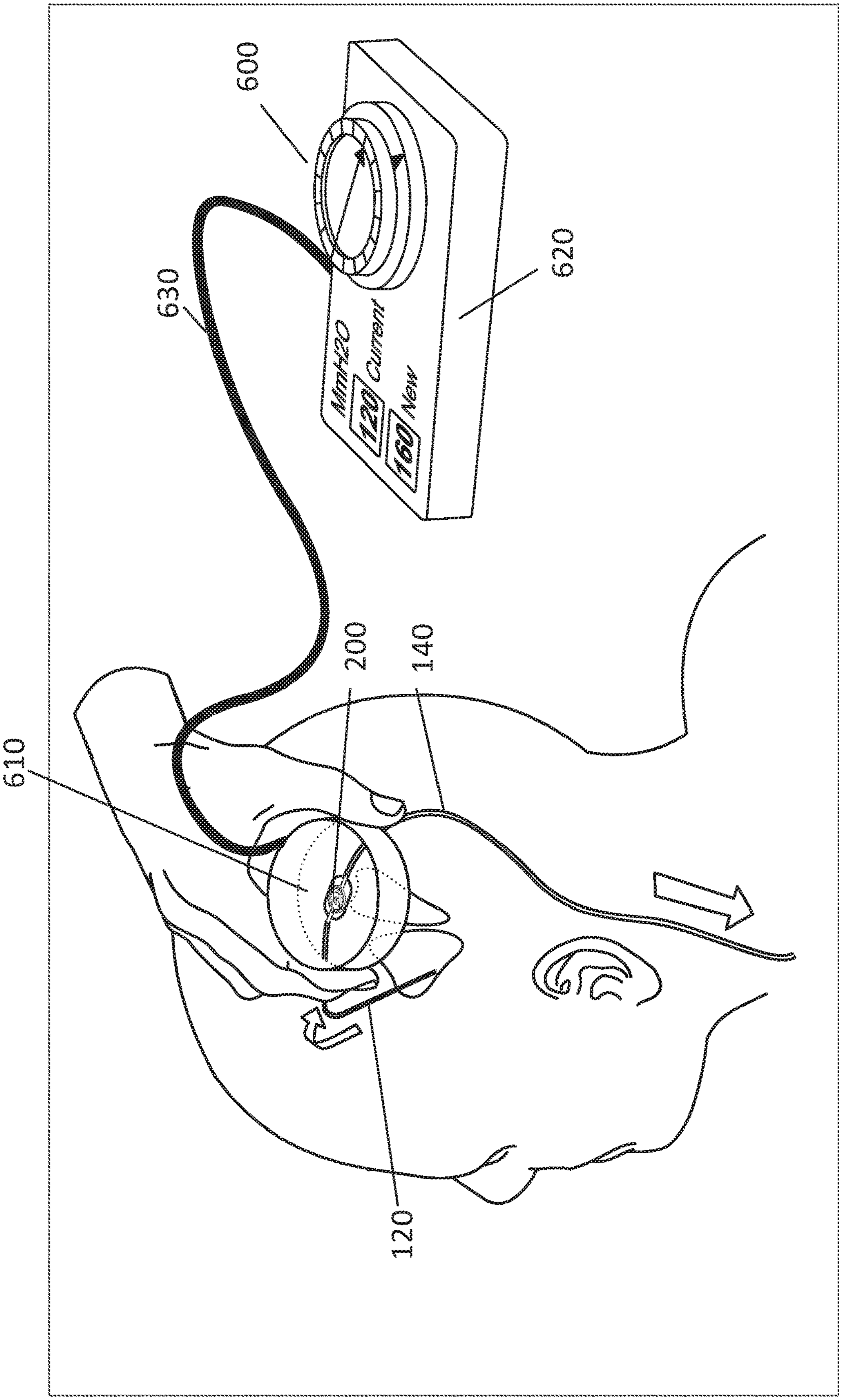
FIG. 11A is a diagram of an implanted valve and an example of an external valve programmer with a control and display, according to aspects of the invention.

FIG. 11A illustrates a valve programmer 600 including a transmitter head 610 which may be placed over the patient's head at a location over an implanted magnetically-programmable valve 200. The transmitter head 610 includes a magnetic field generator, as discussed further below, that applies magnetic pulses to selectively magnetize the stator 528 and thereby cause rotation of the rotor 510. Fluid flows from the ventricle, through a ventricular catheter 120, through the implanted valve, into the distal catheter connected to the connector 140, which then drains the fluid at a remote location of the body (such as the right atrium of the heart or to the peritoneal cavity). The valve programmer 600 may send a magnetic signal through the transmitter head 610 to effect rotation of the rotor 510. A control device 620 may be used to control the transmitter head 610 to produce the magnetic pulses, as discussed further below, and may be coupled to the transmitter head 610 via a communications link 630, such as a cable or wireless link, for example.

Figure 12:
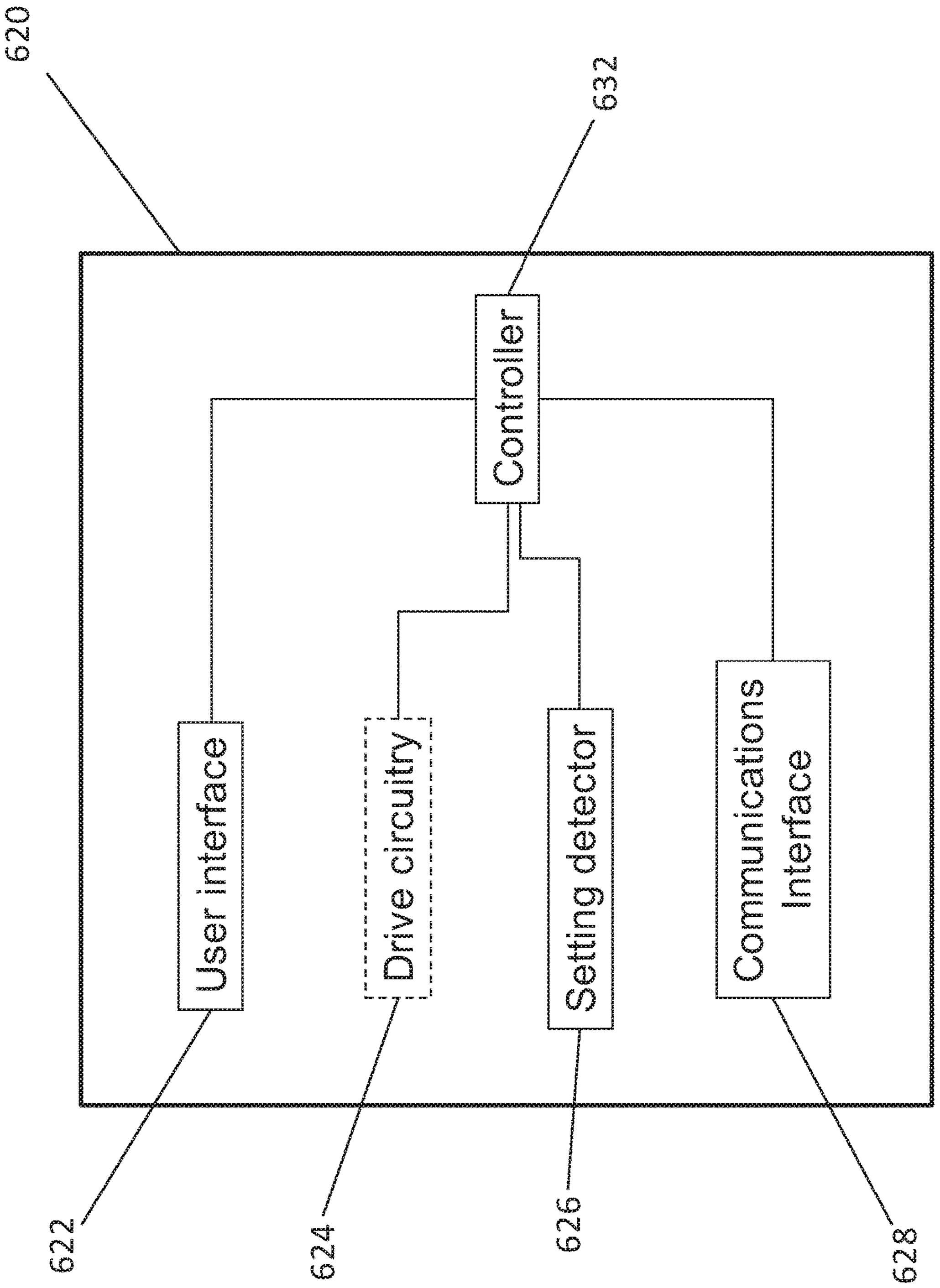
FIG. 12 is a block diagram of one example of an external control device that can be used in combination with an implantable programmable valve according to aspects of the invention.

Referring to FIG. 12, according to certain embodiments, the control device 620 can include a variety of components or modules to enable a user to control the adjustment device to alter the pressure setting of the implantable valve 200, and to determine the current pressure setting of the valve. The control device 620 can include a user interface 622 that allows a user to interact with the control device. The user interface can include one or more displays or input devices, such as input keys, touch screens, etc., to allow a user to view and adjust the pressure settings of the valve 200. In certain embodiments the control device 620 can further include drive circuitry 624 in communication with the transmitter head 610. A controller 632 may be used to provide instruction to the drive circuitry 624 to drive the magnetic field generator in the transmitter head 610 with a predetermined current, duration, cycle, etc., based on instructions received via the user interface 622, for example. The controller 632 may further receive inputs from a setting detector 626, and control the user interface 622 to display the valve pressure setting responsive to information received from the setting detector. The controller 632 may be preprogrammed, for example, by computer instructions stored on a computer readable medium or device, such as a hard disk drive, an optical disk readable by an optical disk reader, a flash memory device, and the like. The control device 620 may be operated to allow a user to adjust the valve 200 through the programmable controller 632 and to determine a setting of the valve 200. In some embodiments, the control device 620 may further include a communication interface 628, which can be used to connect the control device 620 to another device, such as an application server of a networked computer for similarly controlling or otherwise operating the valve 200.

Figure 11B:
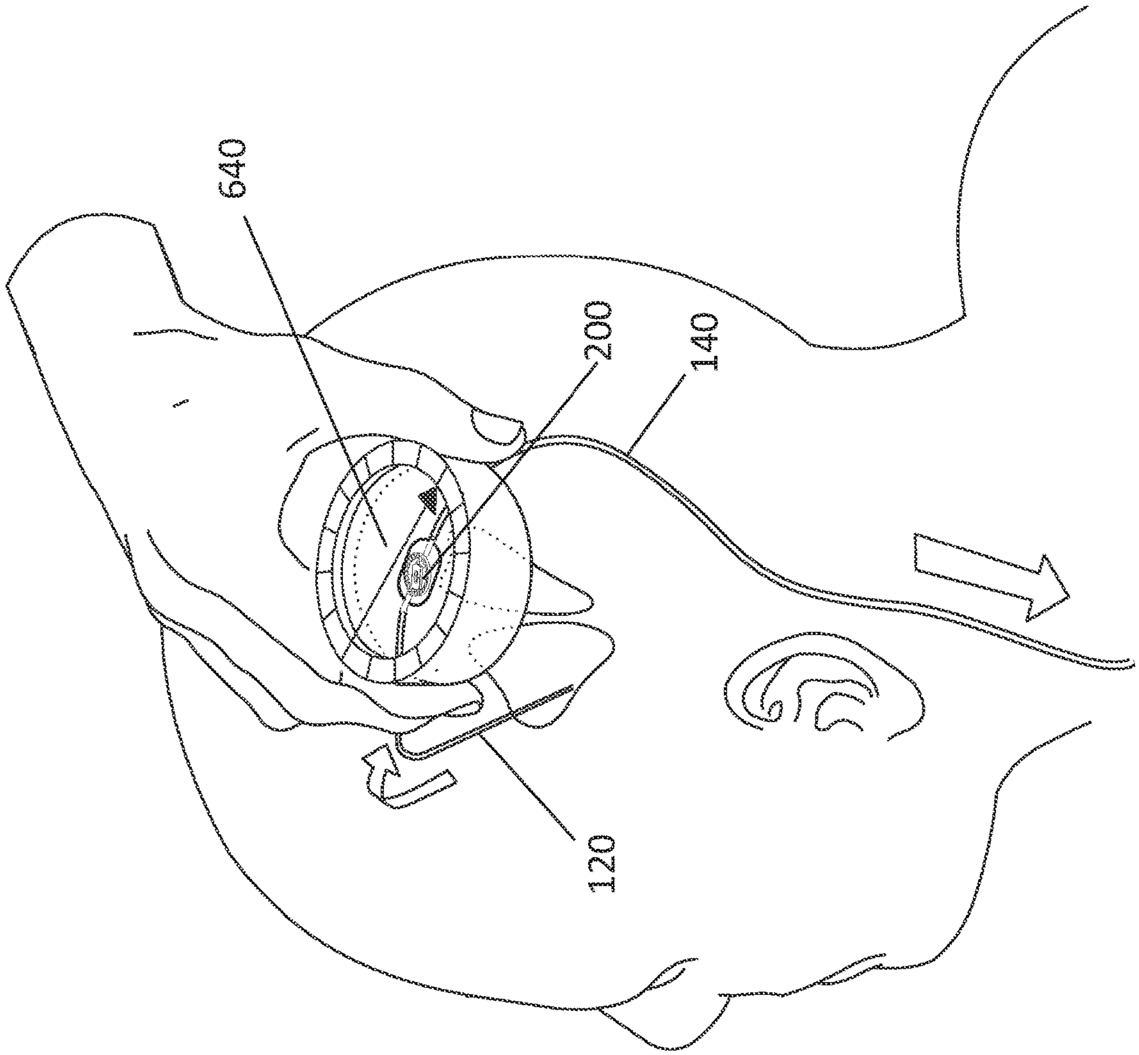
FIG. 11B is a diagram of an implanted device and another example of an external programmer according to aspects of the invention.

FIG. 11B illustrates another embodiment of an external adjustment device 640 that includes a single integrated device, rather than a separate transmitter head 610 and control device 620 as in the example of FIG. 11A. According to one example, the external adjustment device 640 includes permanent north and south magnets that generate a magnetic field, which when rotated, selectively magnetizes the stator 528 and thereby causes rotation of the rotor 510.

Figure 11C:
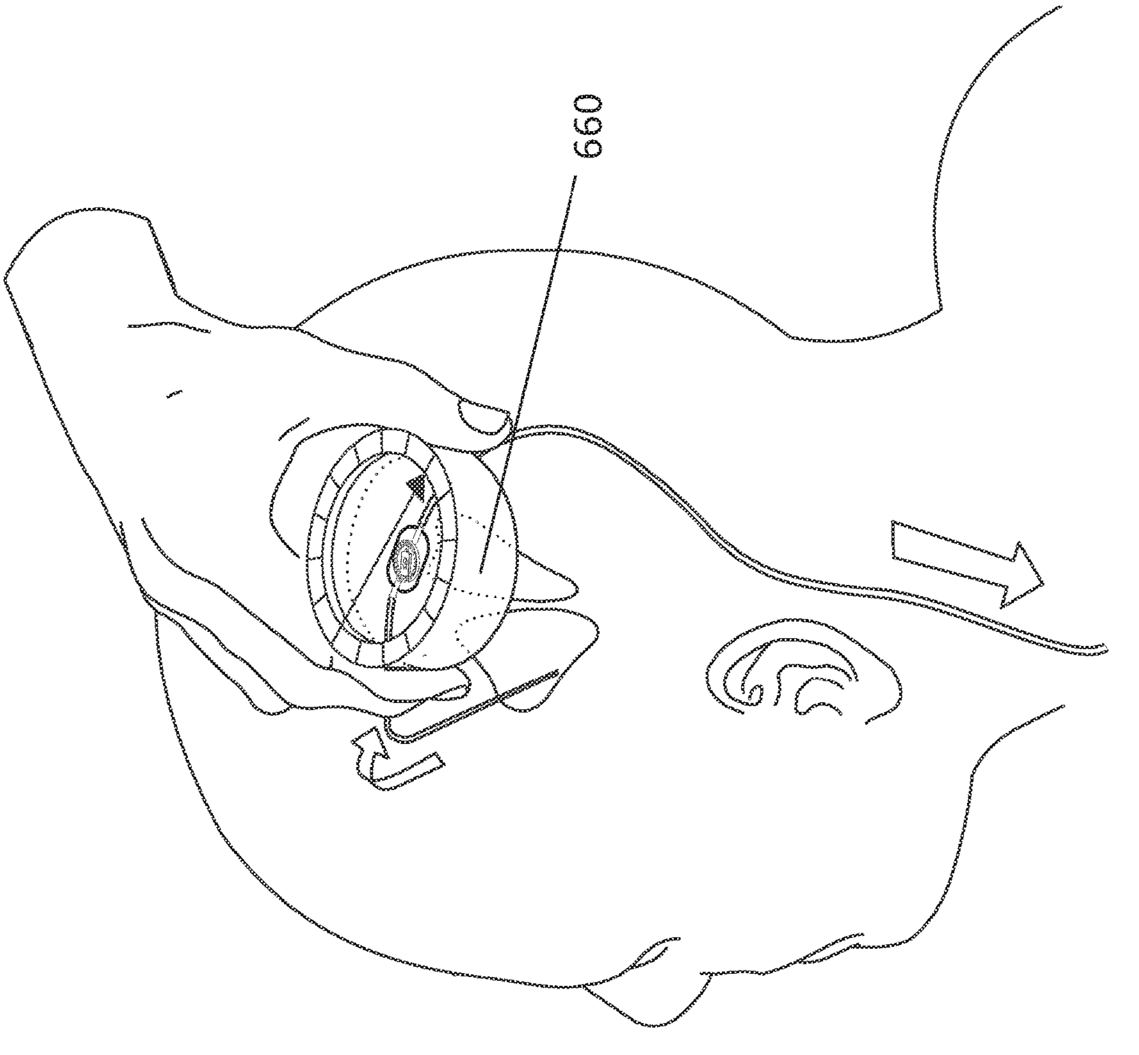
FIG. 11C is a diagram of an implanted valve and an example of a pressure reading device for reading the pressure setting of the valve, according to aspects of the invention.

FIG. 11C illustrates an example of an external valve reading device that includes a valve reading device (pressure reader) 660 for detecting the positional aspect of the rotor 510 in determining the pressure setting of the valve 200. In the illustrated example the pressure reader 660 includes a mechanical compass; however, in other examples the mechanism can be electronic, including a magnetic positional sensor, for example. Embodiments of the pressure reader are discussed in more detail below. In certain examples the pressure reader can be incorporated into embodiments of the valve programmer 600 of FIG. 11A, and configured to determine the positional aspect of the rotor 510, or otherwise read the pressure setting of the valve 200, when the magnetic field generator in the transmitter head 610 is off.

Figure 13:
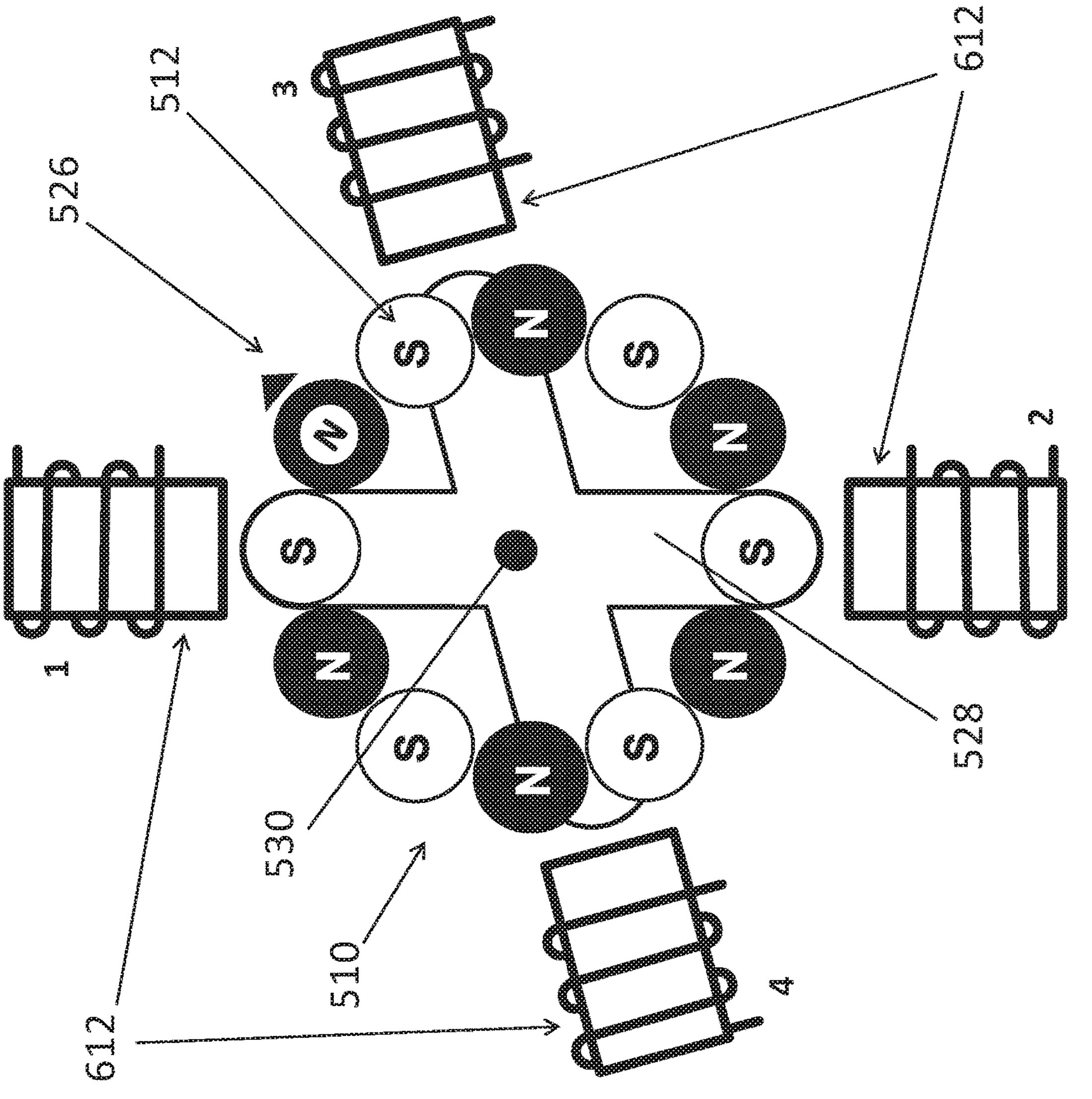
FIG. 13 is a diagram showing operation of one example of a magnetic motor including twelve rotor magnet elements and controlled by a controller including a plurality of electromagnets according to aspects of the invention.
Figure 14:
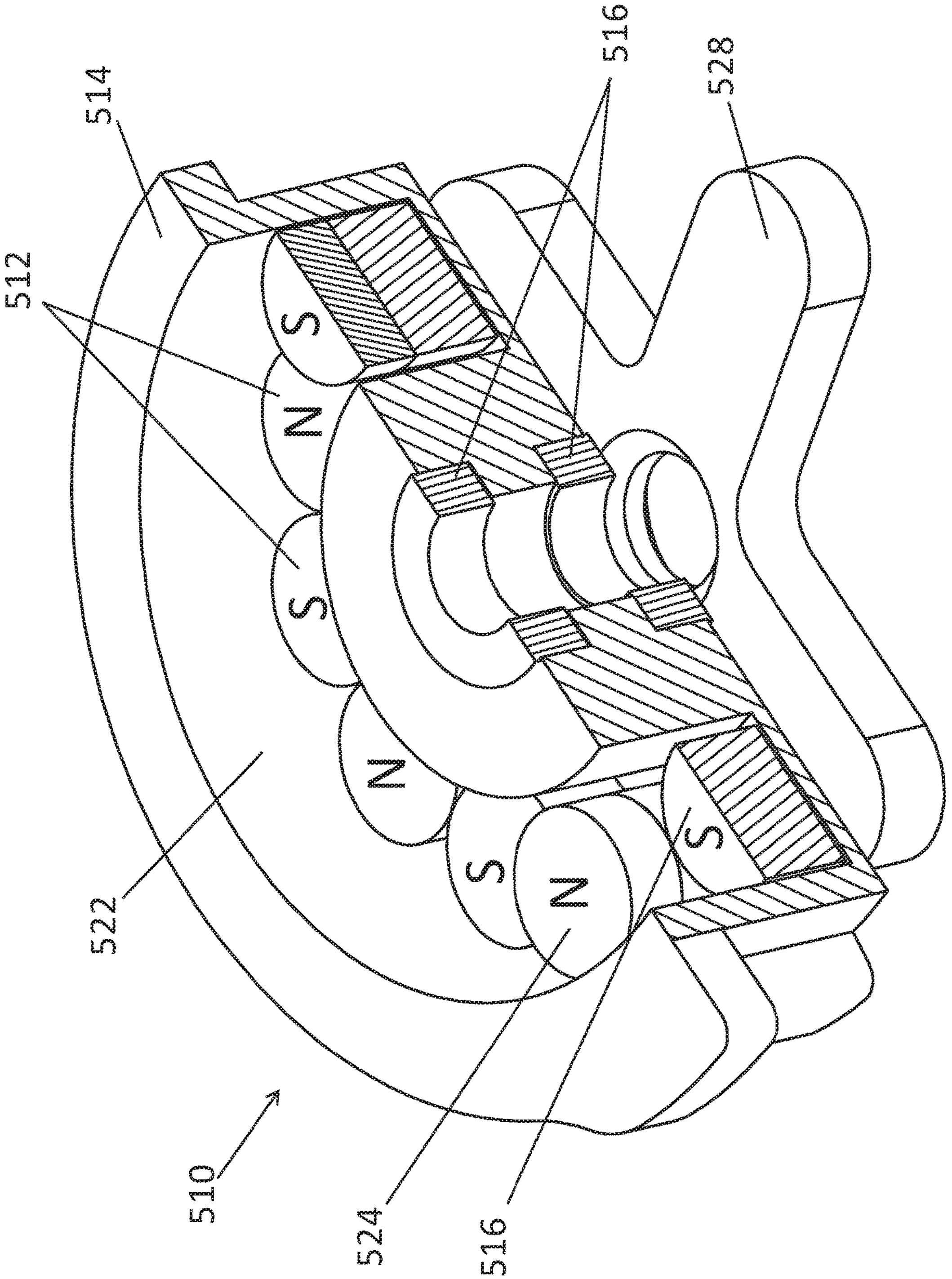
FIG. 14 is a three-dimensional partial cross-sectional view of one example of a magnetic motor according to aspects of the invention.

According to certain embodiments, valve pressure adjustments can be made by applying a pulsed magnetic field to the vicinity of the programmable shunt valve as shown diagrammatically in FIGS. 13, 14, 15, 16A-H, 17, and 18A-H. The transmitter head 610 is placed in proximity to the implanted valve 200. In one embodiment, the transmitter head 610 contains four electromagnets, illustrated schematically in FIG. 13 as coils 1, 2, 3, and 4, which are separately controlled by the external control device 620 (for example, via drive circuitry 624 as discussed above). In the example shown in FIGS. 13 and 14 and as discussed above, the magnetically operable motor of the implanted valve 200 includes the rotor 510, having twelve rotor magnet elements 512 arranged with alternating polarity in channel 522 of the rotor casing 514), as discussed above. The motor further includes the stator 528 positioned below the rotor 510. In the illustrated example, the stator 528 has an X shape. Thus, in this example, the four electromagnets (also referred to as coils) in the transmitter head 610 are positioned such that coils 1 and 3 and coils 2 and 4 are closer to one another than are coils 1 and 4 and coils 2 and 3, as shown in FIG. 13. The four electromagnets can further be positioned equidistant from a central axis 530. When the transmitter head 610 is positioned properly over the implanted valve 200, the central axis 530 of the electromagnets is coincident with the axis of rotation 214 of the rotor 510, and each electromagnet is aligned at the same angular position as one arm of the stator 528, as shown in FIG. 13. It is not, however, necessary that this alignment be exact. Embodiments are tolerant of alignment errors, which may be unavoidable owing to the inability of the user to see the rotor 510 or the stator 528 and to the small size of those elements relative to the size of the external electromagnets.

Each of electromagnets 1, 2, 3, and 4 can be energized to have either the north or south polarity facing the stator 528, or each can remain off altogether. Movement of rotor 510, in the desired direction and through the desired angle, is achieved by energizing the electromagnets in the sequences shown in the tables in FIG. 15 (clockwise rotation) or FIG. 17 (counter-clockwise rotation), which in turn magnetizes the stator 528, which then attracts or repels the rotor magnet elements 512 (depending on polarity), causing rotation of the rotor 510.

For example, referring to FIGS. 15 and 16A-H, clockwise motion is achieved by first energizing both electromagnets 1 and 2 to south polarity, and leaving electromagnets 3 and 4 off (step 1). In the next step (step 2) electromagnets 1 and 2 are left off, and electromagnets 3 and 4 are both energized to south polarity. In step 3, electromagnets 1 and 2 are both energized to north polarity, while electromagnets 3 and 4 remain off, and in step 4, electromagnets 1 and 2 are left off while electromagnets 3 and 4 are energized to north polarity. The sequence repeats itself after the fourth step.

Figure 15:
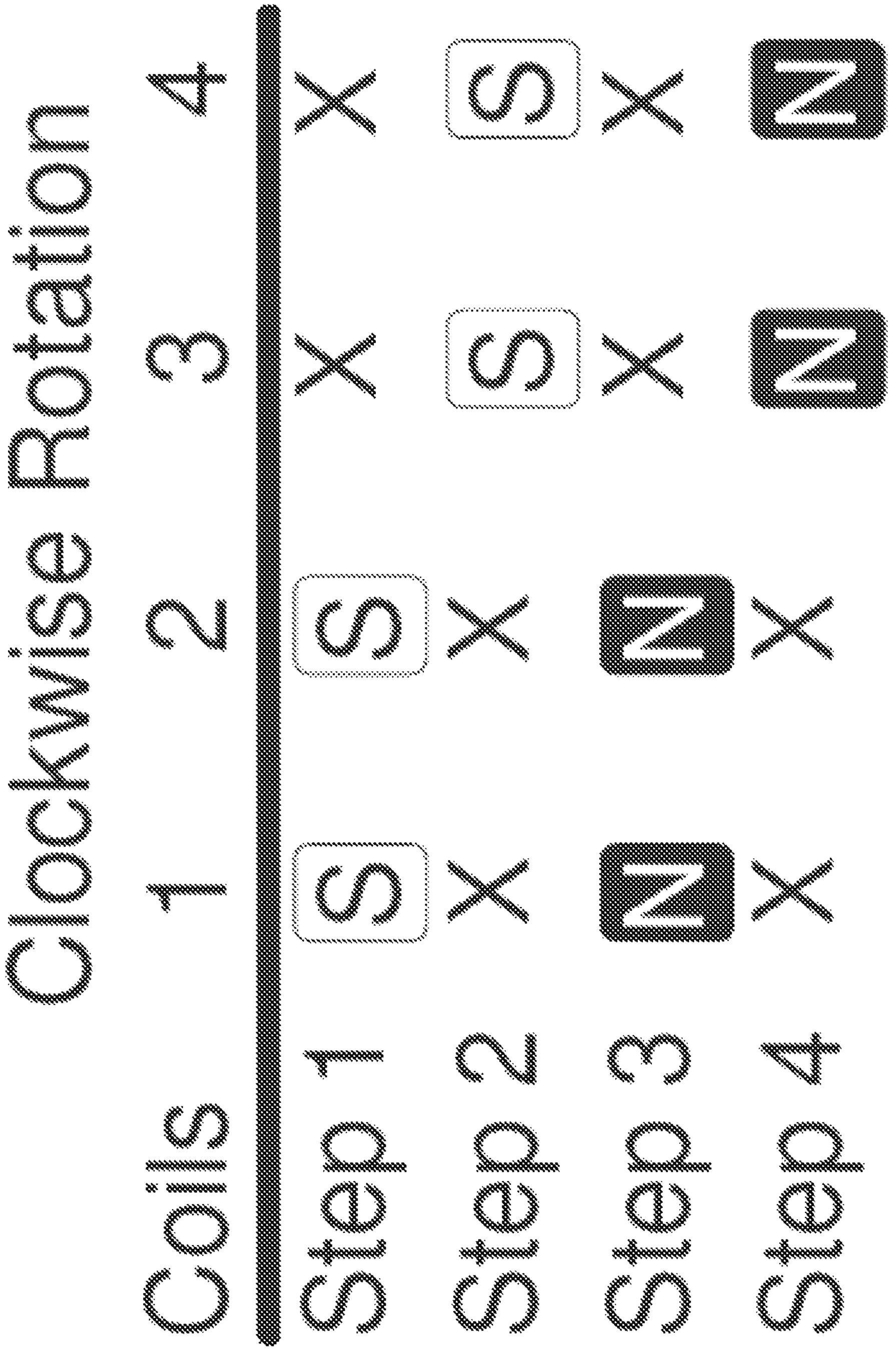
FIG. 15 is a table showing an example of a sequence of energizing the electromagnets of the controller of FIG. 13 to effect clockwise rotation of the magnetic rotor, according to aspects of the invention.
Figure 16A:
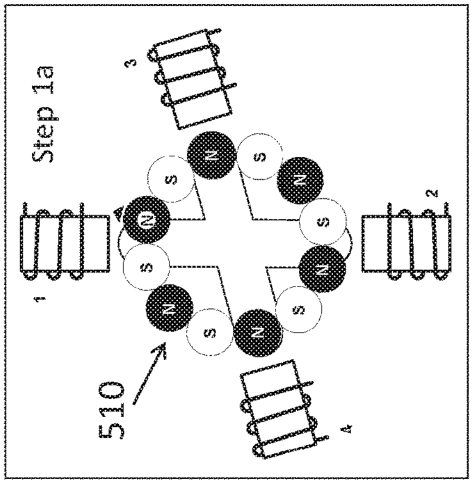
FIGS. 16A-H are diagrams showing the magnetic polarity of the stator and movement of the rotor responsive to the energizing sequence of FIG. 15.
Figure 16B:
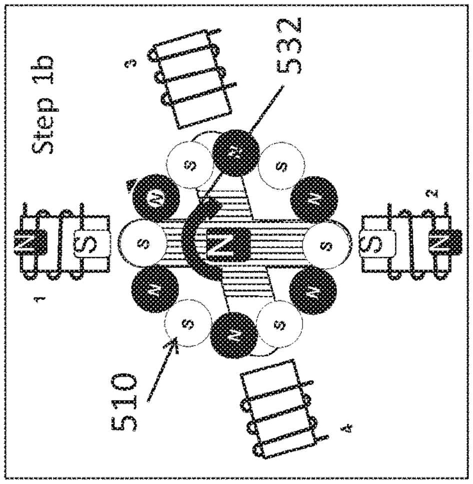
Figure 16C:
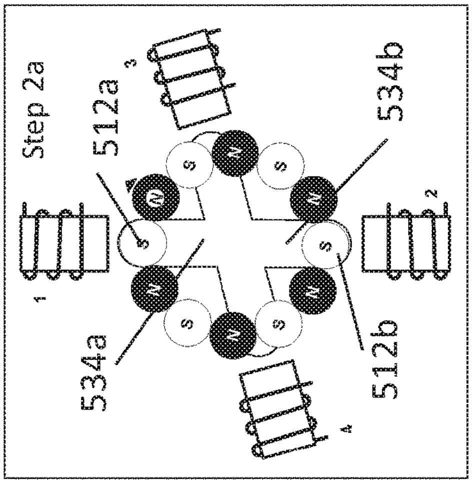
Figure 16D:
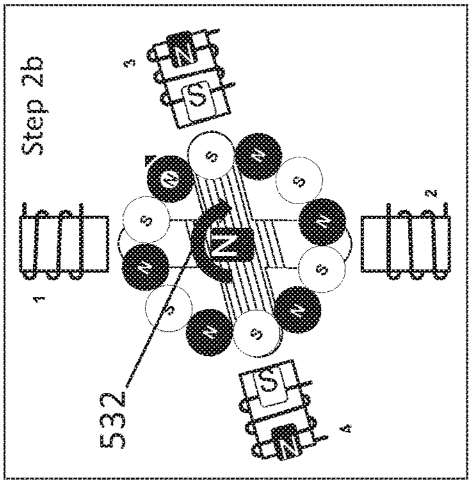
Figure 16E:
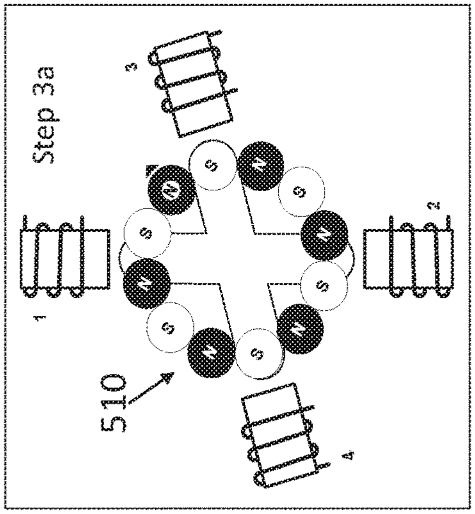
Figure 16F:
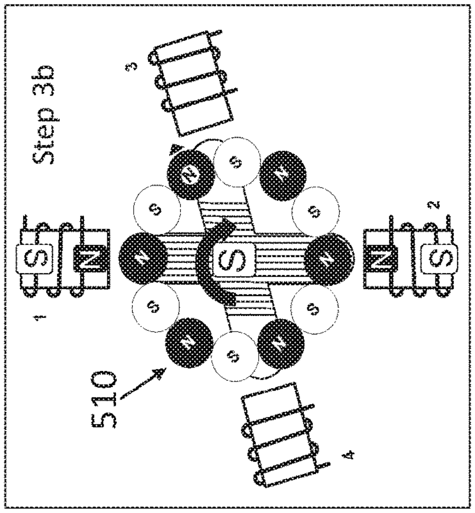
Figure 16G:
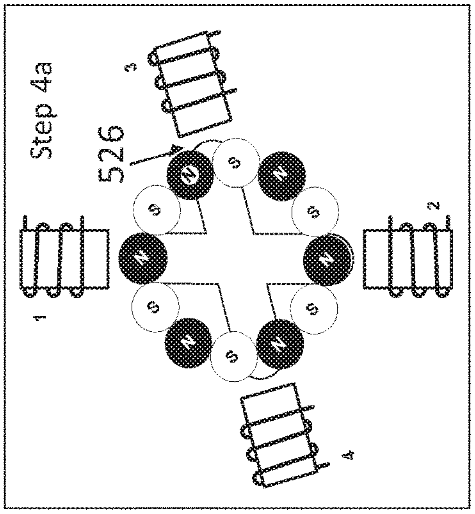
Figure 16H:
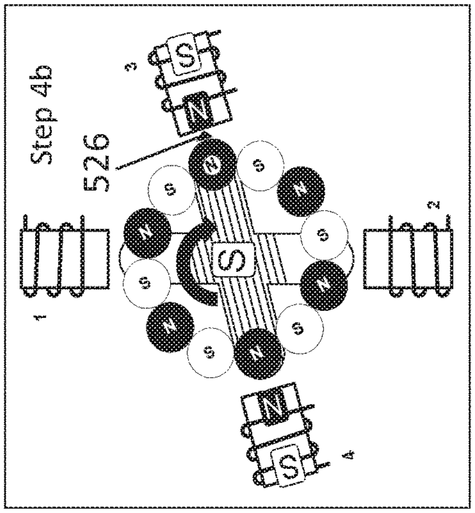

The rotor 510 is shown in FIG. 16B in the position reached after the first step (the polarities of the rotor magnet elements 512 are those corresponding to the bottom surface). As shown in FIGS. 16A and 16B, energizing the electromagnets 1 and 2 such that the south poles are towards the stator 528, and face towards each other, causes the stator 528 to become magnetized with a north polarity. Accordingly, the now north-magnetized stator 528 pulls those rotor magnet elements 512 having south polarity towards itself, while repelling those rotor magnet elements 512 having north polarity. The result is clockwise rotation of the rotor 510, as indicated by arrow 532. Rotation of the rotor 510 may further be seen through FIGS. 16A-H by observing the changing position of reference marker 526. Similarly, in step 2 when electromagnets 3 and 4 are energized such that the south poles are towards the stator 528, and face towards each other, the stator 528 is again magnetized with a north polarity, and acts on the rotor magnet elements 512 to induce further clockwise rotation of the rotor 510, as shown in FIGS. 16C and 16D. FIGS. 16E-H demonstrate the operation corresponding to steps 3 and 4 of FIG. 15. In particular, energizing the electromagnets 1 and 2 such that the north poles are towards the stator 528, and face towards each other (step 3), causes the stator 528 to become magnetized with a south polarity, as shown in FIG. 16E. Accordingly, the now south-magnetized stator 528 pulls those rotor magnet elements 512 having north polarity towards itself, while repelling those rotor magnet elements 512 having south polarity. The result is further clockwise rotation of the rotor 510, as indicated by arrow 532 and shown in FIG. 16F. Similarly, in step 4 when electromagnets 3 and 4 are energized such that the north poles are towards the stator 528, and face towards each other, the stator 528 is again magnetized with a south polarity, and acts on the rotor magnet elements 512 to induce further clockwise rotation of the rotor 510, as shown in FIGS. 16G and 16H.

Movement of rotor 510 is influenced predominantly by the stator 528 positioned beneath the rotor 510 and close to the rotor magnet elements 512 of the rotor 510. Thus, the applied external magnetic field from the electromagnets 1, 2, 3, and 4 does not directly cause movement of the rotor 510, but instead controls magnetization and polarity of the stator 528, which then acts upon the rotor magnet elements 512 to induce rotation of the rotor 510. The number of rotor magnet elements 512 and the shape of the stator 528 are selected such that two conditions are met. First, when one pair of radially opposite stator arms is aligned with one pair of radially opposite rotor magnet elements 512 (e.g., referring to FIG. 16C, stator arms 534*a* and 534*b* are aligned with rotor magnet elements 512*a* and 512*b*, respectively) the other two stator arms are each staggered halfway between two of the rotor magnet elements 512, as shown in FIG. 16C, for example. Second, each pair of radially opposite rotor magnet elements (e.g., 512*a* and 512*b* in FIG. 16C) has the same magnetic polarity. In operation, control device 620 energizes the electromagnets closest to the pair of stator arms staggered between two rotor magnet elements 512, thereby causing the rotor 510 to move through an angle corresponding to one half the width of one rotor magnet element 512. As discussed above, in one example there are twelve magnetic rotor elements 512 and thus 24 angular increments in one full revolution of the rotor 510. Furthermore, this configuration, in which radially opposite rotor magnet elements 512 have the same magnetic polarity and radially opposite electromagnets are also energized to have the same magnetic polarity facing the stator 528 (e.g., south in FIG. 16A) advantageously results in the magnetically programmable valve being highly resistant to other (non-programming) magnetic fields. Randomly applied magnetic fields resulting from natural phenomena or external devices unrelated to the control device 620 (e.g., MRI machines) are highly unlikely to have two same poles (e.g., both poles being either north or south) applied at opposite ends of the stator 528. To the contrary, an external, non-programming field is far more likely to have side-by-side north and south poles, which will fail to uniformly magnetize the stator 528, as is required for controlled operation (as shown in FIGS. 16A-H) and therefore will fail to cause unwanted or accidental rotation of the rotor 510. In contrast, a conventional magnetic rotor, such as that disclosed in U.S. Pat. No. 4,615,691, for example, the rotor includes radially opposite permanent magnets having opposite magnetic polarities (as shown in FIG. 9 of U.S. Pat. No. 4,615,691), along with a cross-shaped stator that is magnetized with one half having one polarity and the other half having the opposite polarity, unlike the stator 528 disclosed herein, which is uniformly magnetized with a single magnetic polarity responsive to the external programming field, as discussed above. Consequently, the conventional device is far more susceptible to unwanted rotation, and therefore unwanted adjustment of the pressure settings of the valve, due to external non-programming magnetic fields.

As discussed above, in one example the rotor 510 includes twelve rotor magnetic elements 512; however, in other examples the rotor 510 can be sized and designed to include a different number of rotor magnet elements 512 (e.g., eight), provided that radially opposite elements have the same magnetic polarity. Further, in other examples in which the rotor 510 is configured to be operated by a differently configured valve programmer, as discussed in more detail below, the rotor may be sized and designed to accommodate a number of rotor magnet elements 512 such (e.g., ten) that radially opposite rotor magnet elements have opposite polarity.

Figure 17:
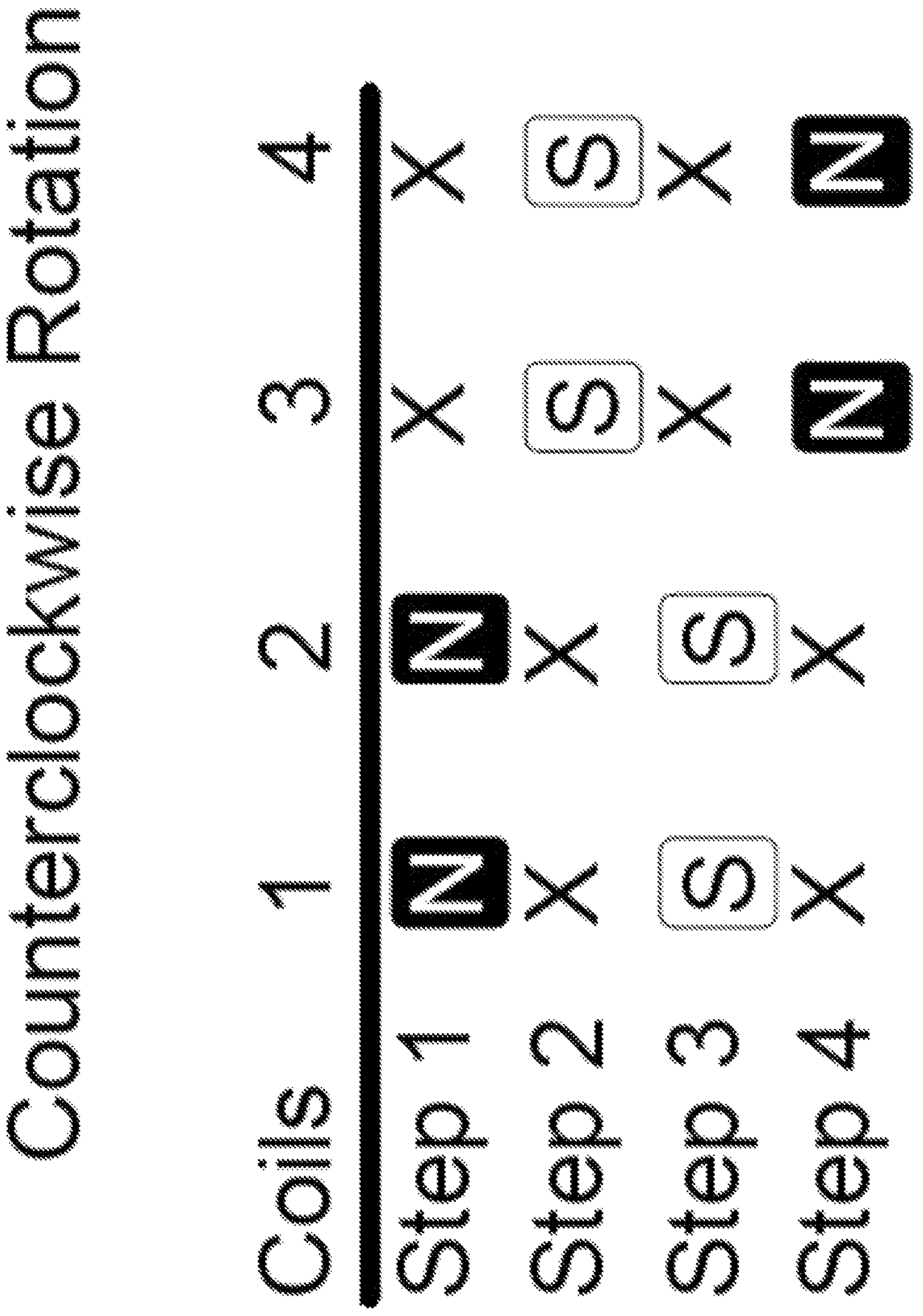
FIG. 17 is a table showing an example of a sequence of energizing the electromagnets of the controller of FIG. 13 to effect counter-clockwise rotation of the magnetic rotor, according to aspects of the invention.

Similar operation can be initiated to induce counter-clockwise rotation of the rotor 510. For example, FIG. 17 is a table, similar to that illustrated in FIG. 15, showing an example of an energizing sequence of the electromagnets of the device of FIG. 13 to effect counter-clockwise rotation of the rotor 510. FIGS. 18A-H illustrate the magnetic polarities of the electromagnets and stator 528, and resulting movement of the rotor 510, corresponding to the sequence shown in FIG. 17.

Figure 18A:
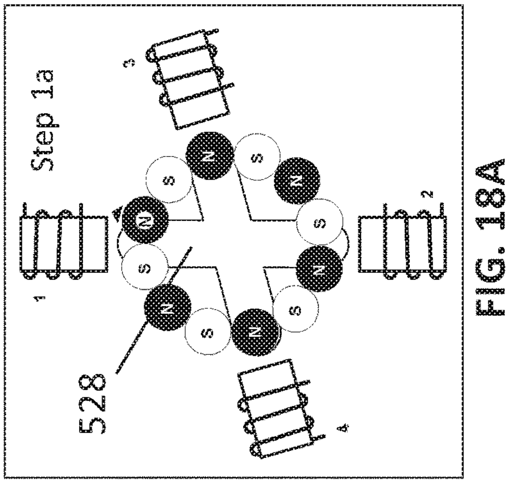
FIGS. 18A-H are diagrams showing the magnetic polarity of the stator and movement of the rotor responsive to the energizing sequence of FIG. 17.
Figure 18B:
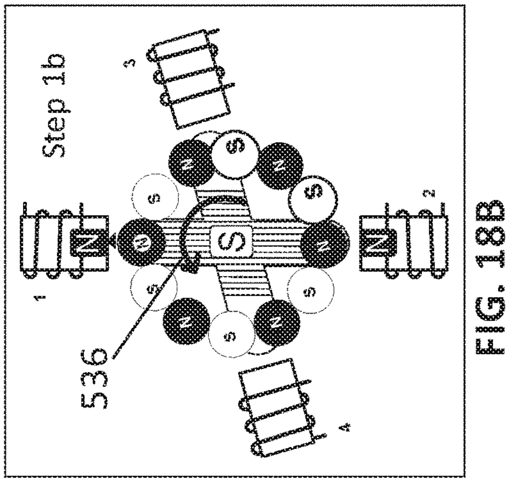
Figure 18C:
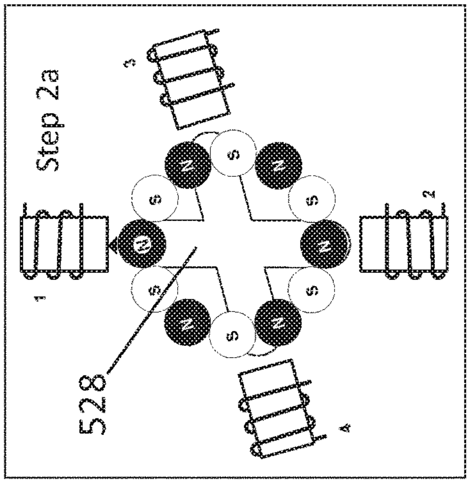
Figure 18D:
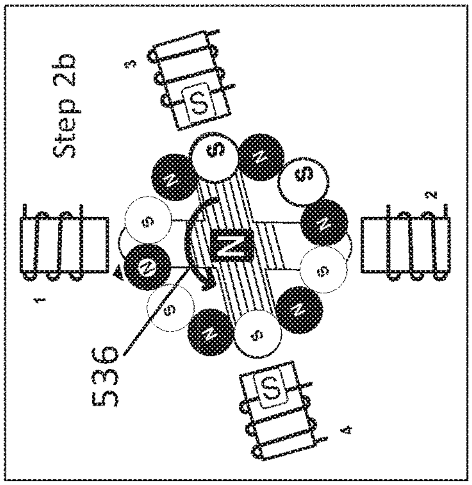
Figure 18E:
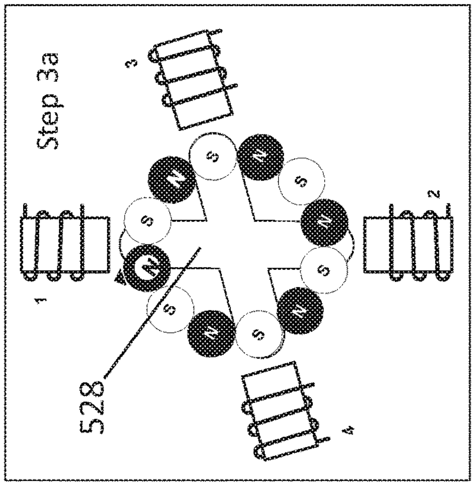
Figure 18F:
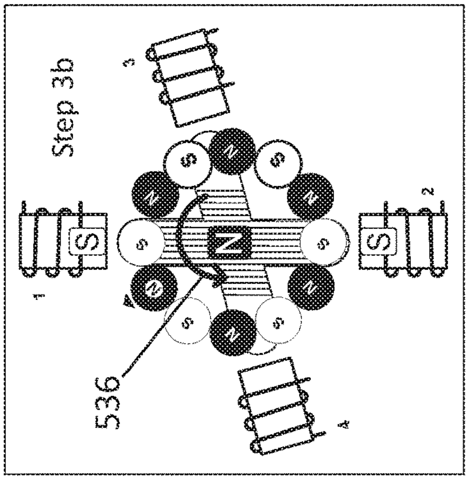
Figure 18G:
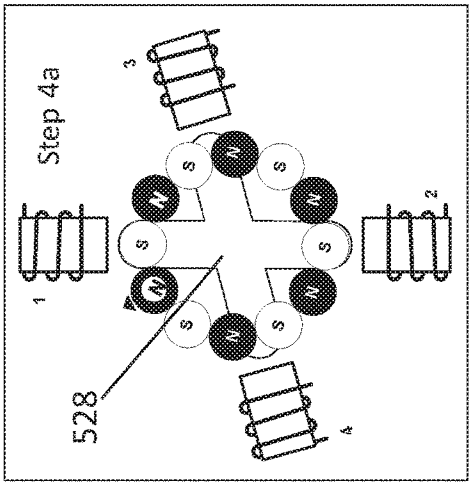
Figure 18H:
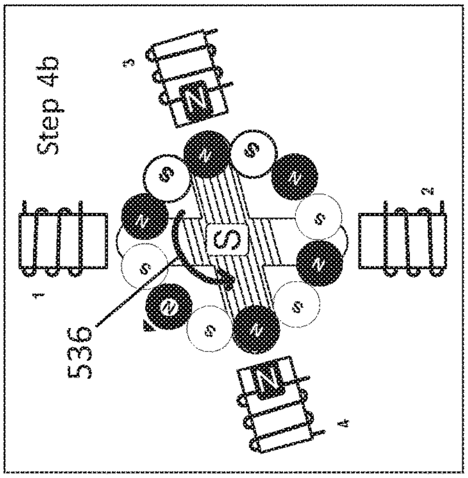

Thus, referring to FIGS. 17 and 18A-H, counter-clockwise motion is achieved by first energizing both electromagnets 1 and 2 to north polarity, and leaving electromagnets 3 and 4 off (step 1). In the next step (step 2) electromagnets 1 and 2 are left off, and electromagnets 3 and 4 are both energized to south polarity. FIGS. 18A-D correspond to steps 1 and 2, with FIG. 18B showing the rotor 510 in the position reached after step 1, and FIG. 18D showing the rotor 510 in the position reached after step 2. As shown in FIGS. 18A-B, energizing the electromagnets 1 and 2 to north polarity causes the stator 528 to become magnetized to south polarity, and induces counter-clockwise rotation of the rotor 510, indicated by arrow 536, by acting on the rotor magnet elements 512 as discussed above. Similarly, as shown in FIGS. 18C-D, energizing the electromagnets 3 and 4 to south polarity causes the stator 528 to become magnetized to north polarity, and induces further counter-clockwise rotation of the rotor 510, indicated by arrow 536. In step 3, electromagnets 1 and 2 are both energized to south polarity, while electromagnets 3 and 4 remain off, and in step 4, electromagnets 1 and 2 are left off while electromagnets 3 and 4 are energized to north polarity. FIGS. 18E-H demonstrate the operation corresponding to steps 3 and 4 of FIG. 17. In particular, energizing the electromagnets 1 and 2 such that the south poles are towards the stator 528, and face towards each other (step 3), causes the stator 528 to become magnetized with a north polarity, as shown in FIG. 18E. Accordingly, the now south-magnetized stator 528 pulls those rotor magnet elements 512 having north polarity towards itself, while repelling those rotor magnet elements 512 having south polarity. The result is further counter-clockwise rotation of the rotor 510, as indicated by arrow 536 and shown in FIG. 18F. Similarly, in step 4 when electromagnets 2 and 3 are energized such that the north poles are towards the stator 528, and face towards each other, the stator 528 is magnetized with a south polarity, and acts on the rotor magnet elements 512 to induce further counter-clockwise rotation of the rotor 510, as shown in FIGS. 18G and 18H. The sequence repeats itself after the fourth step. Each step results in an increment of angular movement of the rotor 510 corresponding to one half the width of one rotor magnet element 512, as discussed above.

Although operation of the magnetic motor and transmitter head 610 is discussed above with reference to a rotor including twelve rotor magnet elements 512, given the benefit of this disclosure, those skilled in the art will appreciate that operation of the transmitter head 610 and its electromagnets can be adjusted for a rotor having a different number of rotor magnet elements, such as ten rotor magnet elements, for example.

Thus, using an implanted valve 200 having the magnetic motor discussed above, along with an external controller that includes a control device 620 and transmitter head 610 having the four electromagnets 1, 2, 3, and 4, the pressure setting of the implantable valve can be non-invasively controlled in small increments. The configuration of the cam 212 and the tension in the spring 400 can be designed and calibrated such that each angular increment of the rotor 510 produces a well-defined selected change in the pressure setting of the valve (e.g., 10 mm $H_2O$). In one example, the control device 620 can be configured to allow the user to enter a desired pressure setting for the valve, and then automatically activate the transmitter head 610, using one of the sequences shown in FIG. 15 or 17, for example, to achieve the selected pressure setting.

In one example, to ensure an accurate pressure setting of the valve 200, the control device 620 can be configured to first activate the counter-clockwise rotation sequence of FIG. 17 to set the valve 200 to its fully open position, and then activate the clockwise rotation sequence of FIG. 15 to set the valve 200 to the selected pressure setting entered by the user. According to certain examples, when the counter-clockwise rotation sequence is activated, the valve programmer is configured to actuate the rotor 510 to rotate through a sufficient number of counter-clockwise steps such that the rotor will be positioned such that the valve 200 has its lowest pressure setting. As discussed above, the presence of the cam stop 220 and housing stop 222 prevent the rotor from continuing to rotate past the minimum pressure setting position. After the programmer stops the counter-clockwise rotation sequence, it may start the clockwise sequence from a known position (the position corresponding to the minimum pressure setting and with the cam stop 220 abutting the housing stop 222). The valve programmer 700 may actuate the rotor 510 to rotate through a selected number of clockwise steps so as to program the valve 200 to the pressure setting selected by the user.

Although the example discussed above uses clockwise rotation of the rotor 510 to program the pressure setting of the valve 200 (and counter-clockwise rotation to set the rotor to a known position from which to begin the programming sequence), those skilled in the art will appreciate, given the benefit of this disclosure, that the system (valve and programmer) can instead be configured for the opposite arrangement, namely to use counter-clockwise rotation of the rotor to program the pressure setting of the valve (and clockwise rotation to set the rotor to a known position from which to begin the programming sequence).

In some instances it may be preferable that the external valve programmer can be battery operated. Transmitter heads such as transmitter head 610 that include electromagnets may require too much power (to energize the electromagnets) to be battery-powered. Accordingly, further aspects and embodiments are directed to a valve programmer, such as the example valve programmers illustrated in FIG. 11B, that incorporates permanent magnets along with a small DC motor, such as a stepper motor, for example, to provide a very low power controller that can be used with the implanted valve 200 and that can be battery-powered.

Figure 19:
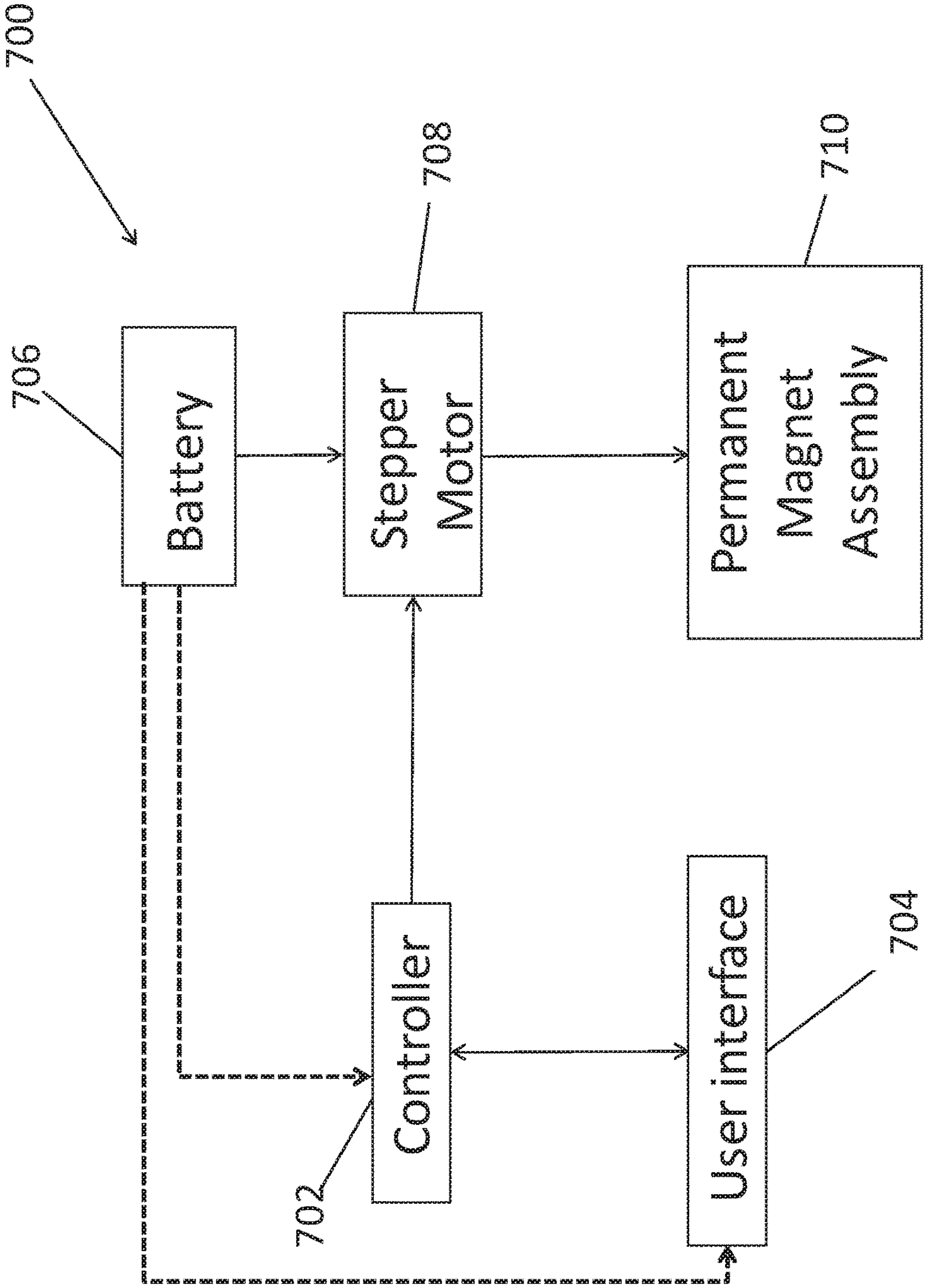
FIG. 19 is a block diagram of another example of an external valve programmer that can be used with embodiments of the implantable valve assembly according to aspects of the invention.

Referring to FIG. 19 there is illustrated a block diagram of one example of a valve programmer 700 incorporating permanent magnets rather than electromagnets. The valve programmer 700 includes a controller 702, a user interface 704, a battery 706, a stepper motor 708, and a permanent magnet assembly 710. These components can be packed together in a single housing that can be held near the implanted valve 200 to control and adjust the pressure setting of the valve 200, as illustrated in FIG. 11B, for example. Alternatively, certain components, such as the permanent magnet assembly 710, stepper motor 708 and battery 706 can be packaged together, optionally including a controller that may perform all or some of the functionality of the controller 702, and user interface 704 (optionally with a controller that may perform all or some of the functionality of the controller 702) can be packaged separately to allow the user to more conveniently view the user interface 704 while operating the valve programmer 700. For example, the user interface 704 can be implemented as an application running on a mobile computing device, such as a smartphone or table computer, for example, that allows the user to view the pressure setting of the valve 200 and enter commands (such as to select a desired pressure setting of the valve 200). The user interface 704 can receive pressure setting information from the controller 702, for example, and transmit the user commands to the other, optionally separately packaged components of the valve programmer 700, for example to the controller 702 or to the stepper motor 708 to actuate the permanent magnet assembly 710 to adjust the pressure setting of the valve 200.

Figure 20A:
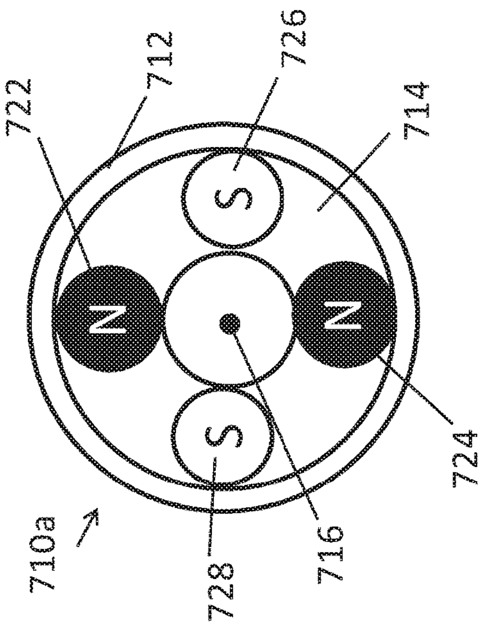
FIG. 20A is a diagram of one example of a permanent magnet assembly for the external valve programmer of FIG. 19, according to aspects of the invention.

FIG. 20A is an illustration of one example of a permanent magnet assembly 710*a* that can be used in the valve programmer 700 according to certain embodiments. The permanent magnet assembly 710*a* includes a housing 712 and a rotatable magnet guide 714 disposed within the housing 712 and configured to rotate about a central axis of rotation 716. In one example, the stepper motor 708 drives rotation of the magnet guide 714 under control of the controller 702. The rotation of the magnet guide 714 can be continuous or a series of discrete steps. A plurality of permanent magnets are mounted to or within the magnet guide 714 such that the permanent magnets rotate with the magnet guide 714. In the example illustrated in FIG. 20A there are four permanent magnets 722, 724, 726, and 728. The two radially opposite permanent magnets have the same magnetic polarity. For example, as illustrated in FIG. 20A, permanent magnets 722 and 724 have north polarity while permanent magnets 726 and 728 have south polarity. This configuration is appropriate for controlling the rotor 510 having twelve rotor magnet elements 512, for example.

Figure 20B:
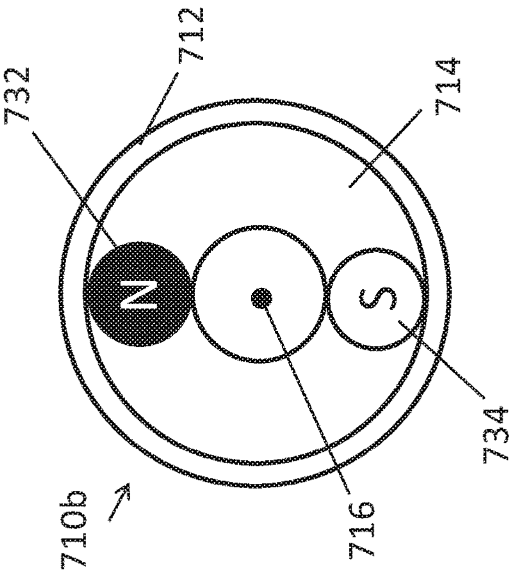
FIG. 20B is a diagram of another example of a permanent magnet assembly for the external valve programmer of FIG. 19, according to aspects of the invention.

Those skilled in the art will appreciate that a wide variety of modifications to the permanent magnet assembly 710 can be made. For example, although the four permanent magnets 722, 724, 726, and 728 are illustrated in FIG. 20A as being round, they may have other shape, such as, but not limited to, rectangular, oval, bar-shaped, rod-shaped, and the like. Additionally, there may be more than or fewer than four permanent magnets. For example, FIG. 20B illustrates a configuration in which the permanent magnet assembly 710*b* includes a pair of permanent magnets 732 and 734 of opposite magnetic polarity. This configuration may be appropriate for controlling the rotor 510 having ten rotor magnet elements 512, instead of twelve, for example. In another example, the permanent magnet assembly 710*b* can include a single diametrically magnetized permanent magnet, rather than two separate magnets of opposite polarity. It is further to be appreciated that any of the permanent magnets 722, 724, 726, 728, 732, or 734 can be comprised of a cluster of multiple permanent magnets of the same magnetic polarity, rather than being single permanent magnets. Actuated by the stepper motor 708, the magnet guide 714, and therefore the plurality of permanent magnets 722, 724, 726, and 728, or 732 and 734, rotate about the axis of rotation 716. When the valve programmer 700 is placed over the implanted valve 200, the permanent magnet assembly 710 magnetizes the stator 528. Rotation of the magnet guide 714 changes the magnetization of the stator 528, and thereby induces movement of the rotor 510, similarly as discussed above with respect to the transmitter head 610.

Figure 21A:
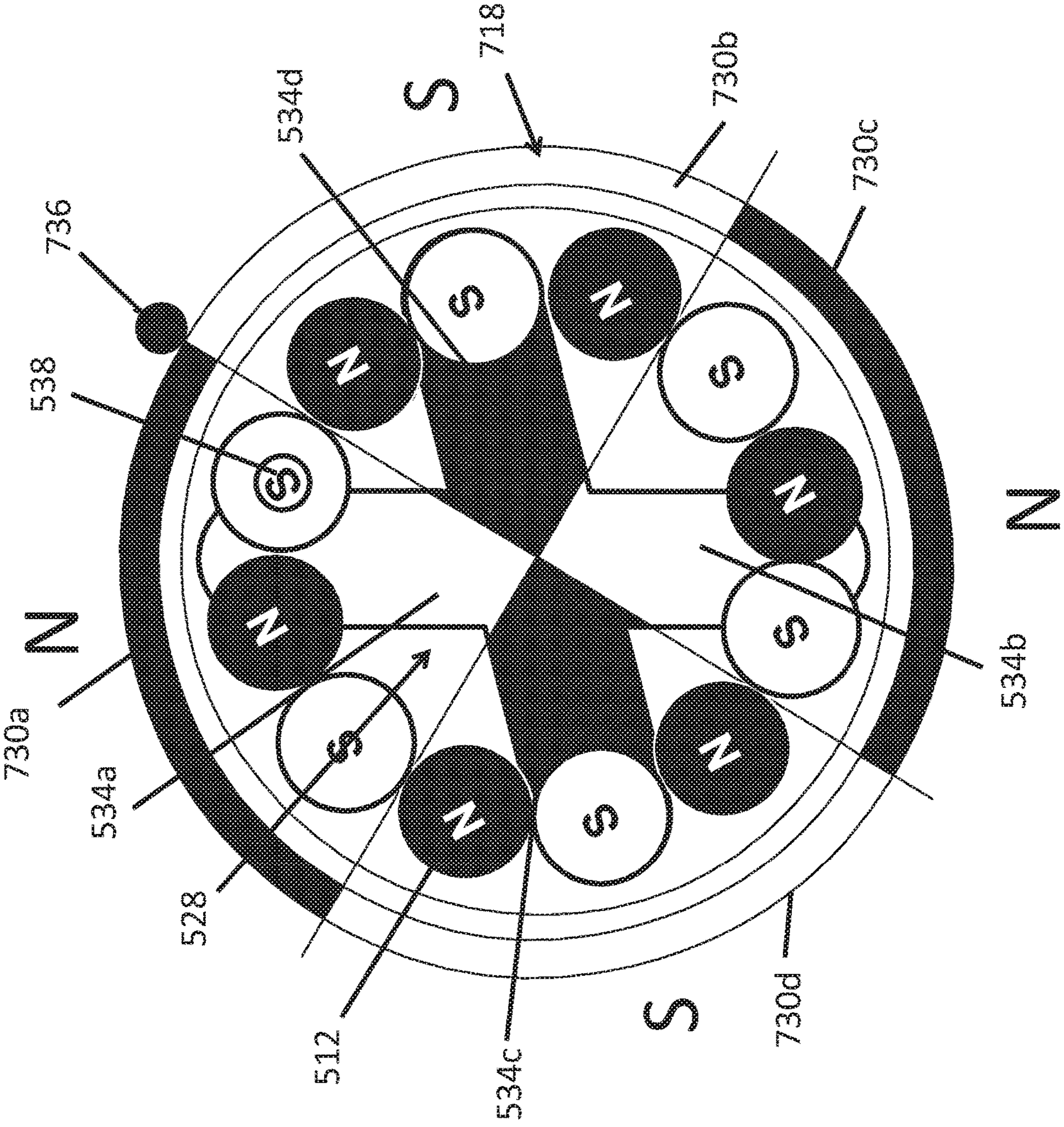
FIGS. 21A-E are diagrams illustrating an example of the changing magnetic polarity of the stator and movement of the rotor under control of an example of an external valve programmer incorporating the permanent magnet assembly of FIG. 20A, according to aspects of the invention.

FIGS. 21A-E diagrammatically illustrate an example of the changing magnetic polarity of the stator 528, and resulting rotation of the rotor 510, responsive to rotation of the magnet guide 714 for the example of the valve programmer 700 including the permanent magnet assembly 710*a* of FIG. 20A. In FIGS. 21A-E, the permanent magnet assembly 710*a* is diagrammatically represented by ring 718. As shown in FIG. 21A, for example, the ring 718 has four magnetic quadrants, two of each magnetic polarity (730*a* and 730*c* are north, and 730*b* and 730*d* are south) and with radially opposite quadrants having the same magnetic polarity, corresponding to the four permanent magnets 722, 724, 726, and 728 shown in FIG. 20A. The ring 718 includes a controller reference marker 736 which is intended to illustrate rotation of the magnet guide 714 through FIGS. 21A-E and which does not necessarily correspond to a physical structure. Similarly, a rotor reference marker 538 is illustrated on one of the rotor magnet elements 512 to illustrate rotation of the rotor 510 through FIGS. 21A-E.

Referring to FIG. 21A, in a first position, the two oppositely positioned permanent magnets having south polarity (permanent magnets 726 and 728 in FIG. 20A) corresponding to quadrants 730*b* and 730*d* of ring 718 cause the opposing stator arms 534*c* and 534*d* to which they are closest or aligned to be magnetized to north. Similarly, the other two oppositely positioned permanent magnets having north polarity (permanent magnets 722 and 724 in FIG. 20A) corresponding to quadrants 730*a* and 730*c* of ring 718 cause the other two opposing stator arms 534*a* and 534*b* to which they are closest or aligned to be magnetized to south. The stator arms 534*a* and 534*b* now magnetized to south are staggered between two rotor magnet elements of opposite magnetic polarity, and therefore pull the north-polarized rotor magnet elements 512*a* and 512*b* while repelling the south-polarized rotor magnet elements 512*c* and 512*d*, resulting in rotation of the rotor 510 to the position shown in FIG. 21B. The rotor 510 rotates through an angle corresponding to one half the width of one rotor magnet element 512, as illustrated by the relative displacement of the rotor reference marker 538 from FIG. 21A to FIG. 21B. The degree of rotation of the rotor 510 corresponds to a 45 degree rotation of the ring 718, as illustrated by the relative displacement of the controller reference marker 736 from FIG. 21A to FIG. 21B.

Figure 21B:
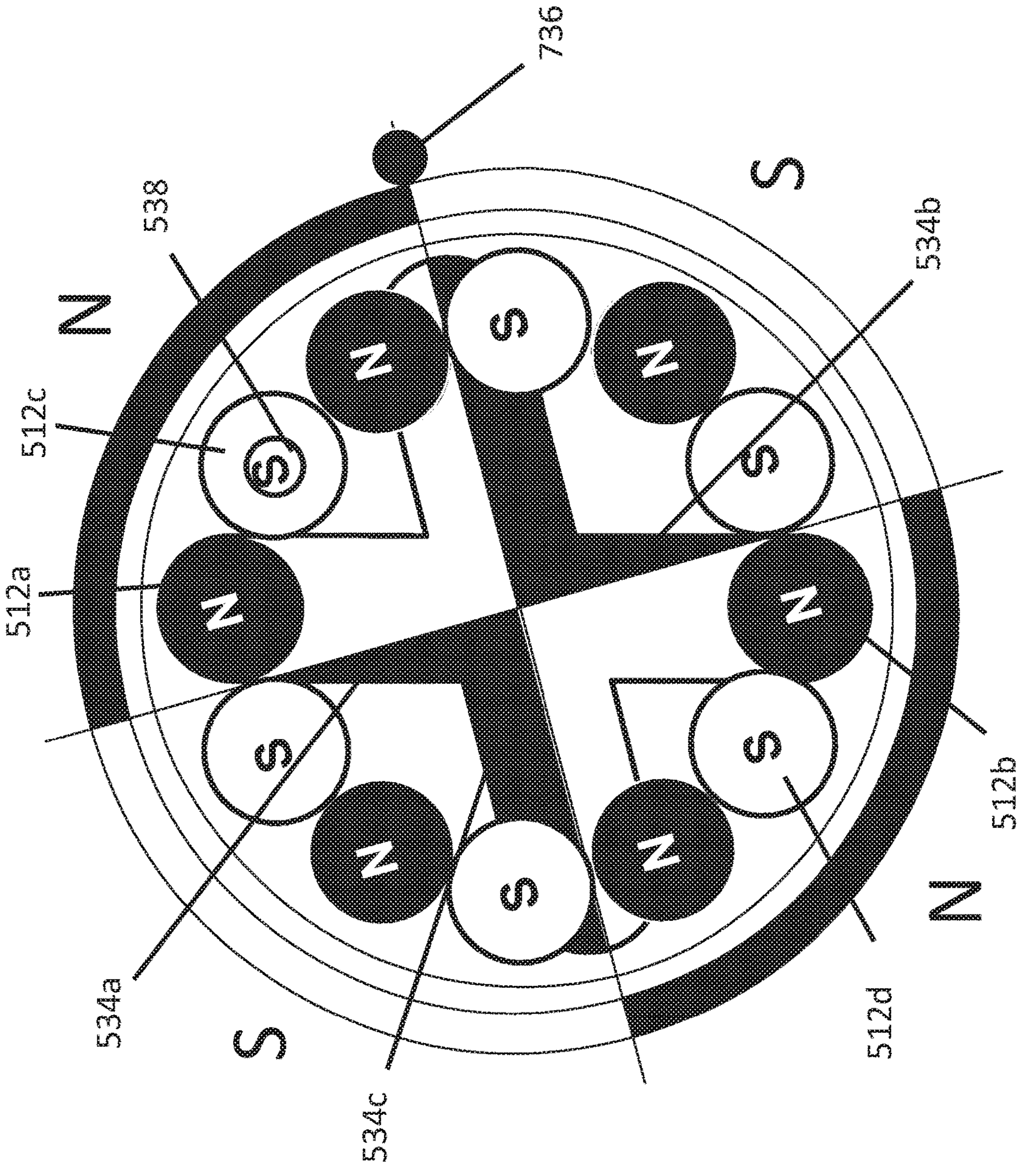

In FIG. 21A, the four permanent magnets 722, 724, 726, and 728, represented by quadrants 730*a-d* of the ring 718, are each aligned with one of the stator arms 534*a-d*, respectively. Referring to FIG. 21B, in this second position, which is achieved by 45 degrees of rotation of the ring 718 (i.e., as indicated by the reference marker 736 of the permanent magnet assembly 710*a*) from the first position (FIG. 21A), each of the four permanent magnets 722, 724, 726, and 728, represented by quadrants 730*a-d* of the ring 718, is now staggered across two stator arms. As a result, each of the stator arms 534*a-d* has a split magnetic polarization, with a portion of each arm being magnetized to north and another portion being magnetized to south, as shown in FIG. 21B.

Figure 21C:
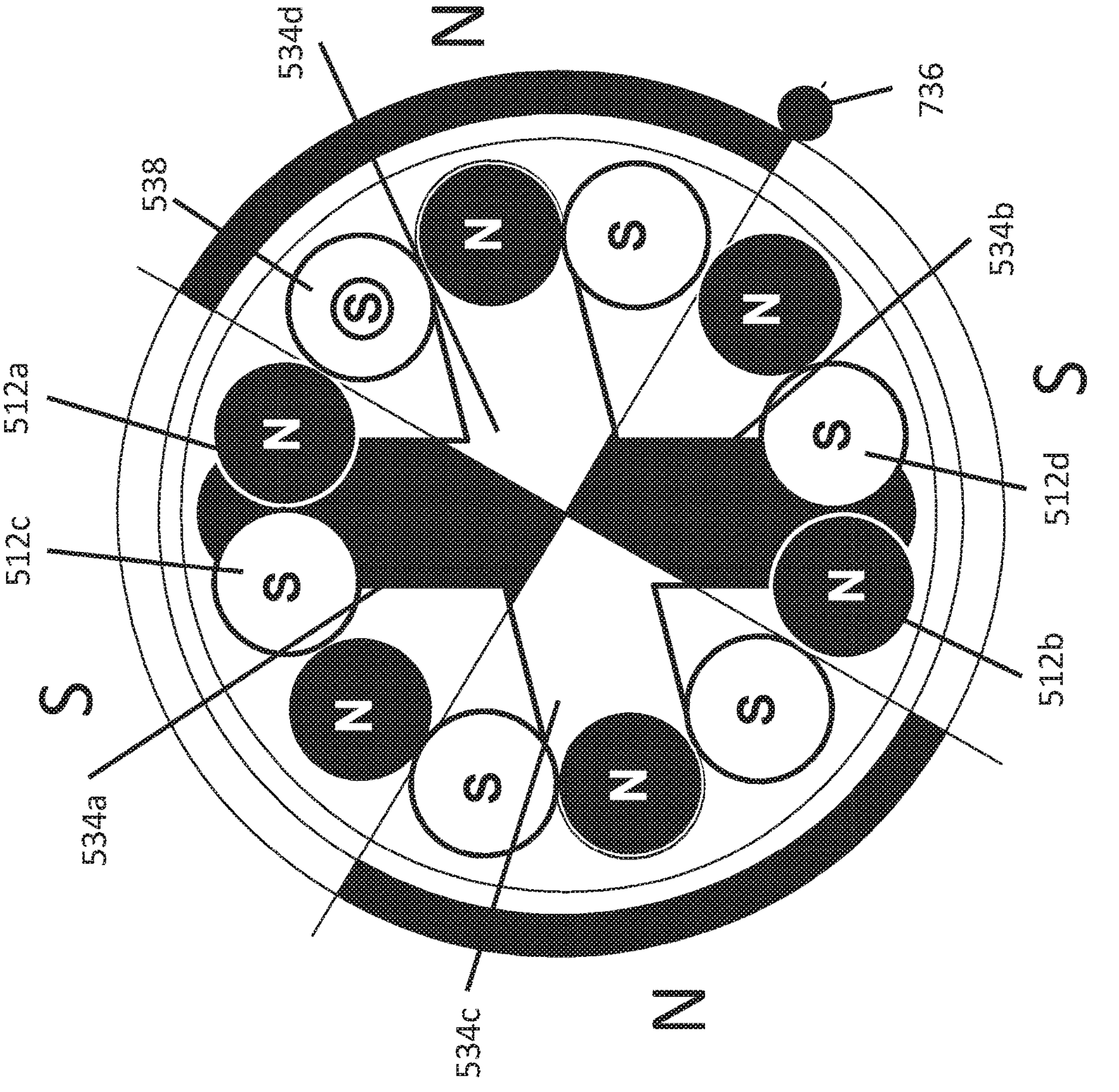

Referring to FIG. 21C, a further 45 degree rotation of the magnet guide 714 as indicated by the reference marker 736 re-aligns the four permanent magnets 722, 724, 726, and 728 of the permanent magnet assembly 710*a* with the stator arms 534*a-d*. As shown, opposing stator arms 534*a* and 534*b* are now magnetized to north, and opposing stator arms 534*c* and 534*d* are now magnetized to south. The stator arms 534*a* and 534*b* now magnetized to north are again staggered between two rotor magnet elements 512 of opposite magnetic polarity, and therefore repel the north-polarized rotor magnet elements 512*a* and 512*b* and pull the south-polarized rotor magnet elements 512*c* and 512*d*, resulting in another angular increment (corresponding to one half the width of one rotor magnet element 512) of rotation of the rotor 510 to the position shown in FIG. 21D.

Figure 21D:
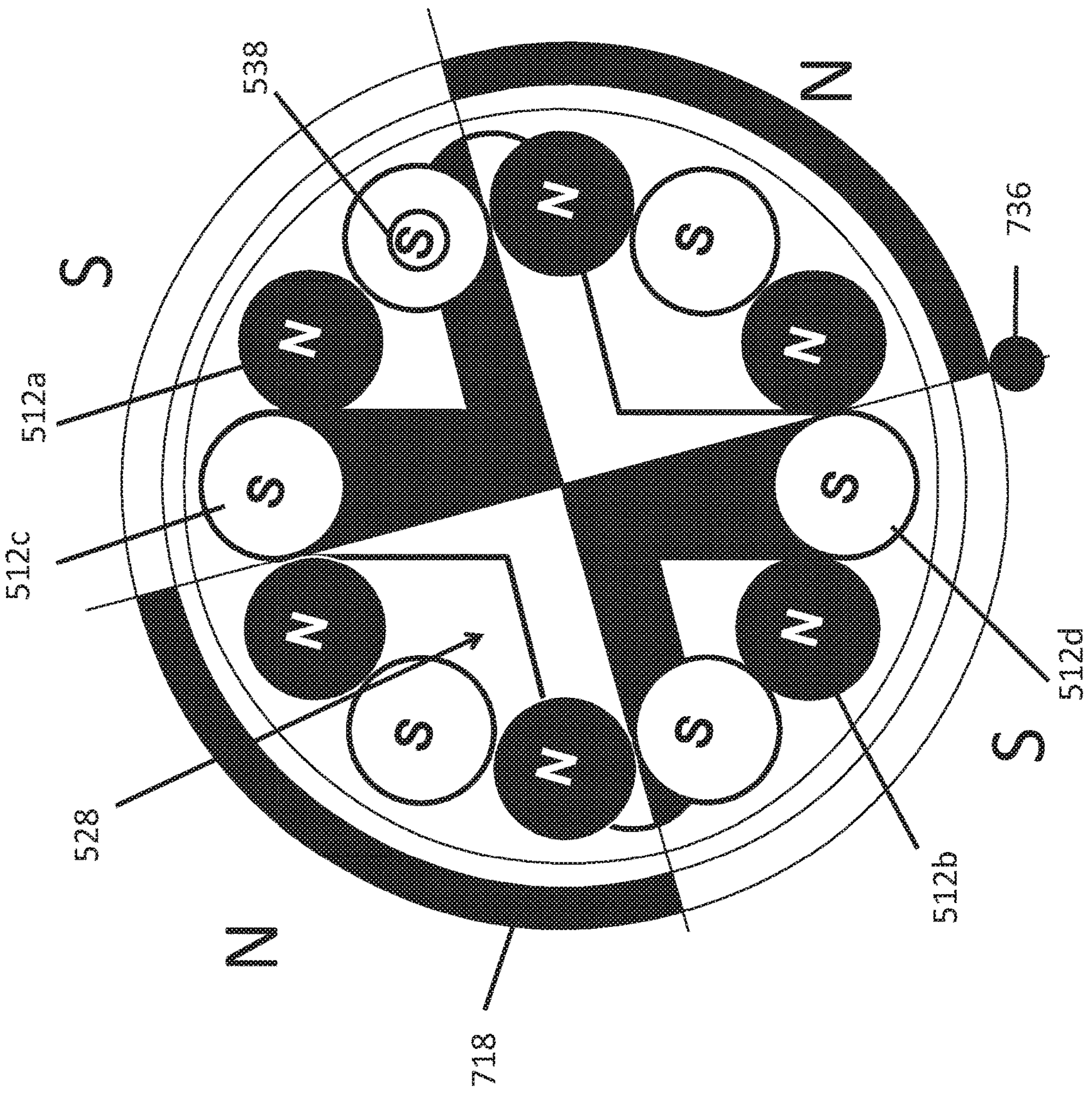

Referring to FIG. 21D, a further 45 degree rotation of the magnet guide 714, represented by ring 718 and indicated by the reference marker 736, again results in the arms of the stator 528 each having split magnetic polarity. Another 45 degree rotation of the magnet guide 714 returns the stator 528 to the magnetic polarity configuration of FIG. 21A and causes rotor 510 to rotate by another angular increment, as shown in FIG. 22. The cycle continues to repeat with further rotation as shown in FIG. 21E of the magnet guide 714 for the external permanent magnets 722, 724,726, and 728 of FIG. 20A.

Figure 21E:
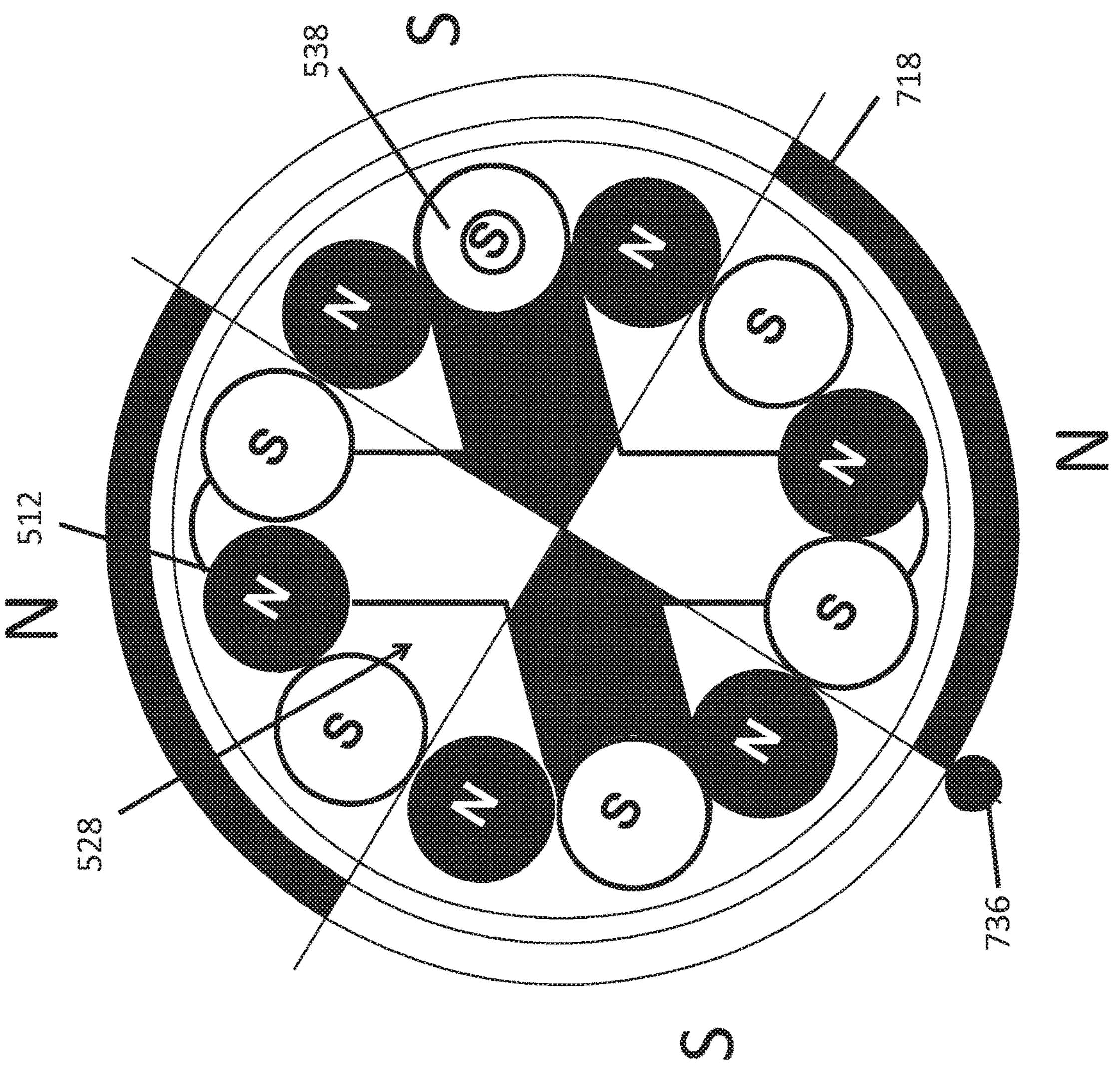
Figure 22:
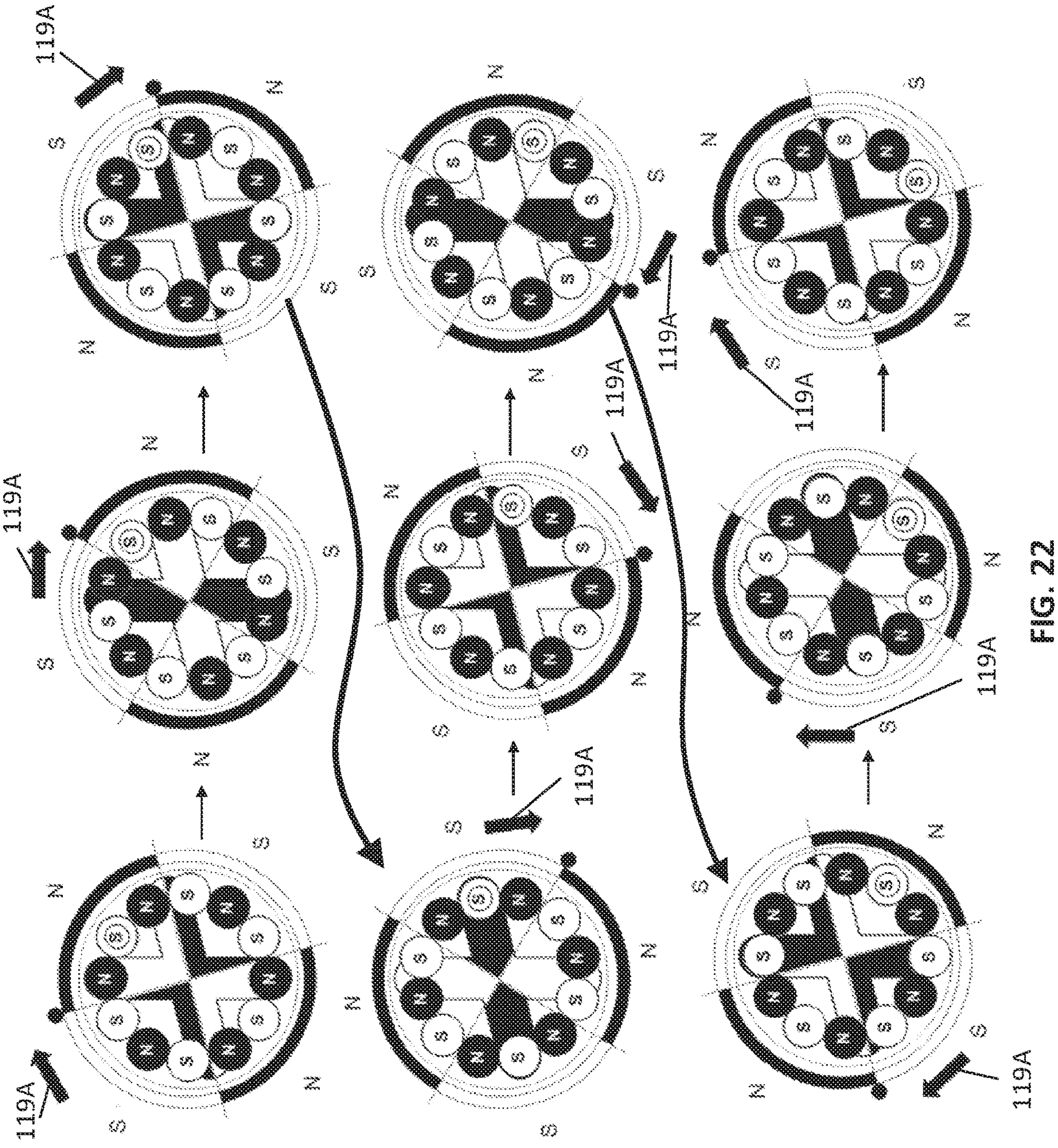
FIG. 22 is a flow diagram illustrating an example of the changing polarity of the stator and movement of the rotor as exemplified in FIGS. 21A-E representative of one full rotation of an external permanent magnet valve programmer, according to aspects of the invention.

Thus, for the implementation of the rotor 510 shown in FIG. 4C, for example (circular arrangement of twelve rotor magnets 512) and the valve controller including the permanent magnet arrangement shown in FIG. 20A, 180 degrees of rotation of the magnet guide 714 (as can be seen by comparing the positions of the controller reference marker 736 in FIGS. 21A and 21E) results in four angular increments of rotation of the rotor 510 (corresponding to movement equivalent to two times the width of one rotor magnet element 512), as may be seen by comparing the positions of the rotor reference marker 538 in FIGS. 21A and 21E. Thus, three complete revolutions of the magnet guide 714 results in one complete revolution of the rotor 510. This "gear reduction" effect achieved through the indirect action of the valve programmer 700 on the rotor 510 (via the stator 528) advantageously allows for very small incremental movements of the rotor 510 without requiring correspondingly small movements in the valve programmer 700. This can improve ease of use of the valve programmer 700 by a user, or simplification of manufacture of the valve programmer 700 because the magnet guide 714 is not required to be as small as the rotor 510 of the implantable valve 200.

Adjustments in the gear ratio between the valve programmer 700 and the rotor 510 can be achieved by altering the configuration (e.g., number of magnets) of the permanent magnet assembly or the rotor 510. For example, using a similar rotor arrangement as shown in FIG. 4C, but with ten rotor magnets instead of twelve rotor magnets, and the permanent magnet assembly with two permanent magnets 732 and 734 of FIG. 20B instead of that of FIG. 20A, results in five complete revolutions of the magnet guide 714 causing one complete revolution of the rotor 510. As will be appreciated by those skilled in the art, given the benefit of this disclosure, various other combinations of external permanent magnets and rotor magnets can be implemented, and are considered as part of this disclosure and intended to be within the scope of the present invention.

FIG. 22 is a flow diagram showing rotation of the valve programmer and corresponding changing magnetization of the stator and rotation of the rotor, in accord with the operation discussed above with reference to FIGS. 21A-E. Arrows 119A show rotation of the rotor at each step in the flow diagram.

In certain examples the valve programmer 700 can be packaged in a hand-held housing 762 such that it is comfortable and easy for a user to use. FIGS. 23A-23D illustrate an example 760 of the valve programmer 700. In this example, the valve programmer 760 has a shape that is similar to a computer mouse. As shown, in some embodiments, the valve programmer 760 has rounded corners on its outer surfaces, and may have an overall rounded shape, which may be easy and/or comfortable for a user to hold. In some embodiments, the valve programmer 760 can be easily held by a user in one hand.

Figure 23A:
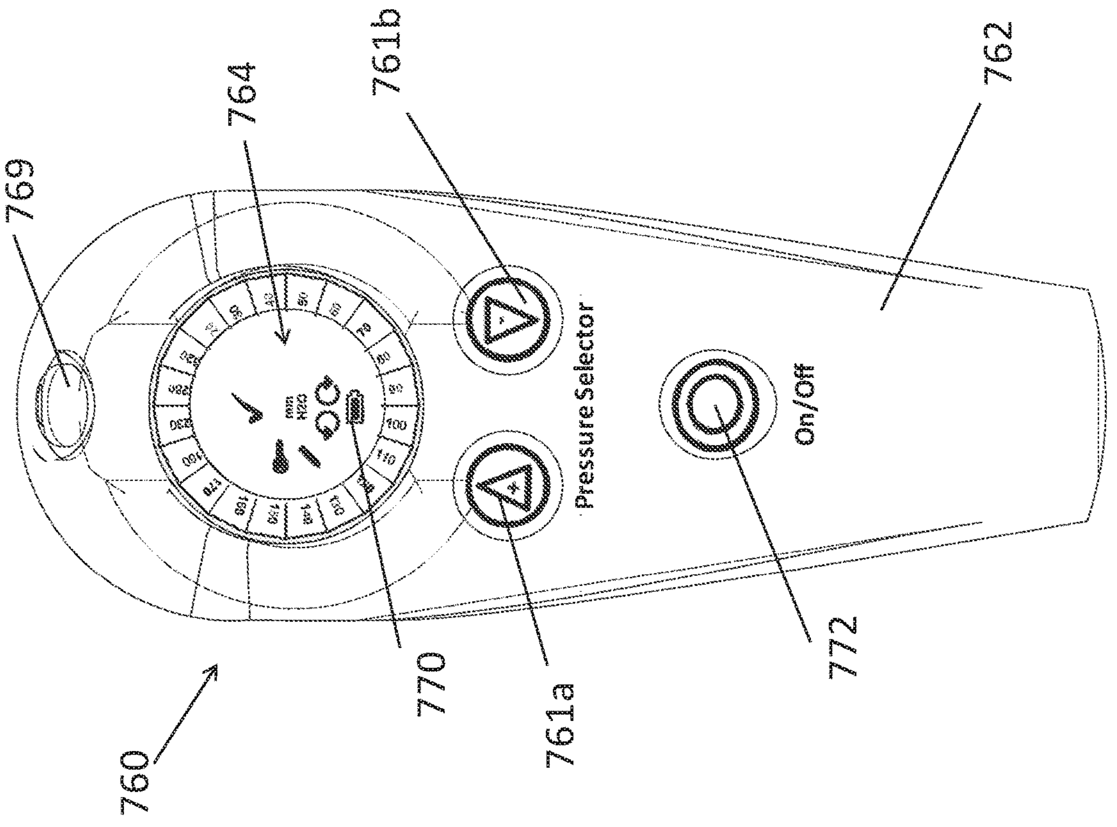
FIG. 23A is a diagram showing a top plan view of one example of a valve programmer according to aspects of the present invention.
Figure 23B:
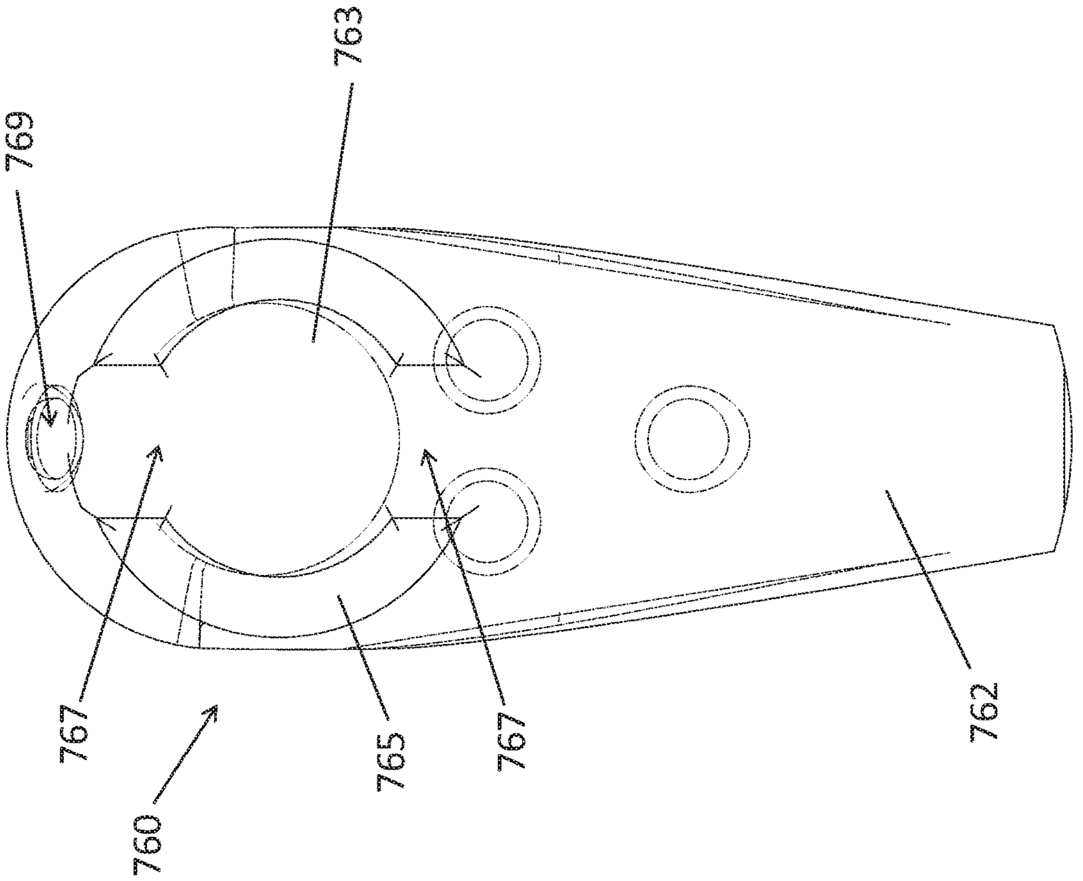
FIG. 23B is a diagram showing a bottom plan view of the valve programmer of FIG. 23A.
Figure 23C:
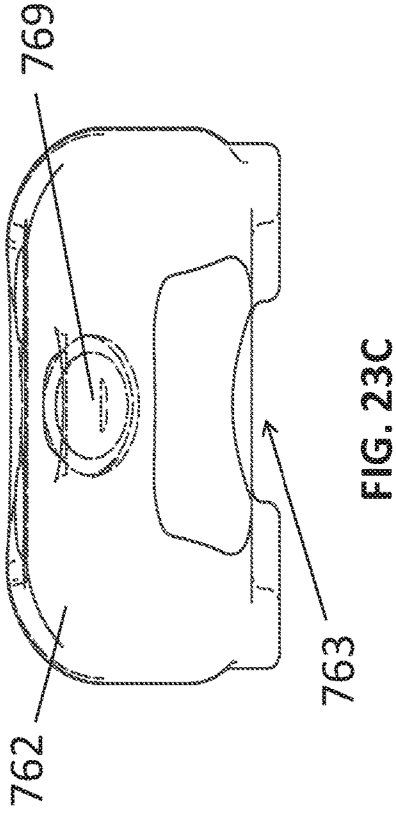
FIG. 23C is a diagram showing an end view of the valve programmer of FIGS. 23A-B.

FIG. 23A shows a top view of the valve programmer 760. FIG. 23B shows an underside view of the valve programmer 760. FIG. 23C shows an end view of the valve programmer 760, and FIG. 23D shows a perspective view of the valve programmer 760.

As discussed above, the valve programmer 760 can be battery operated. Accordingly, in some embodiments, the housing 762 can house one or more batteries, along with the magnet assembly 710 (not shown in FIGS. 23A-D). As discussed above, in some embodiments, the valve 200 includes a ten magnet stepper motor, and the magnet assembly 710 of the valve programmer 760 two oppositely magnetized magnets for rotating the stepper motor of the valve 200. The two oppositely magnetized magnets have opposite fields oriented downwardly within the valve programmer 760. In some embodiments, the programmer magnets have a surface field strength of 6000 gauss.

Figure 23D:
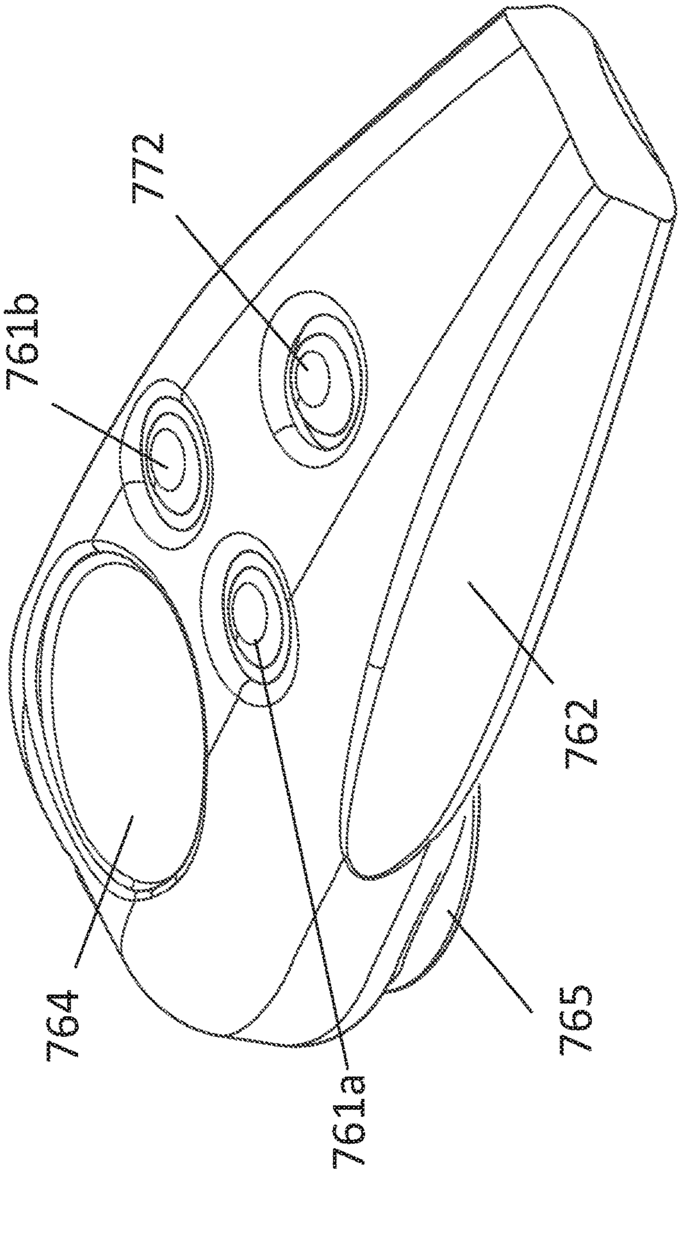
FIG. 23D is a diagram showing a perspective view of the valve programmer of FIGS. 23A-C.

As shown in FIGS. 23A and 23D, the valve programmer 760 may include a user interface 764 that shows information such as the pressure setting, the battery status 770, and optionally other information. For example, the center of the user interface 764 screen may show the pressure that was selected (in a digital read-out). The border of the screen may include an indication of what an X-ray would show, or the position of the valve rotor that may be indicated by a pressure reader, as discussed further below.

The valve programmer 760 includes an interface mechanism to allow a user to select the pressure setpoint of the valve programmer 760, and thereby to set the pressure of the valve 200. In some embodiments, as shown in FIG. 23A, the valve programmer 760 includes a first button 761*a* to increase the pressure setpoint and a second button 761*b* to decrease the pressure setpoint. Alternatively, the valve programmer 760 may include a wheel (such as the wheel shown in the embodiment of FIG. 23E) that is rotatable in a first direction to increase the pressure setpoint, and rotatable in a second direction to decrease the pressure setpoint. In some embodiments, the valve programmer 760 can include the first button 761*a*, the second button 761*b*, and the wheel. In some embodiments, the valve programmer 760 can set the valve 200 to one of 20 pressure settings, as discussed above. In some embodiments, the highest pressure setting does not completely close the valve 200. This can be useful for testing whether the patient still needs the valve 200 without completely closing the valve 200 and thereby avoiding potential injury to the patient.

The valve programmer 760 may further include a programming button 769 that when pressed causes the valve programmer 760 to actuate the magnet assembly 710 to program the valve 200. In some examples the programming button 769 can be located on the front edge of the housing 762, as shown in FIG. 23A.

The valve programmer 760 may also include an on/off button 772, as shown in FIGS. 23A and 23C.

Referring to FIGS. 23B and 23C, the housing 762 of the valve programmer 760 can be shaped to facilitate correctly orienting the valve programmer 760 over an implanted valve 200 to program the pressure setting of the valve 200. In certain examples, the housing 762 includes a molded cavity 763 defined by sidewalls 765 on the bottom of the valve programmer 760. The cavity 763 is shaped and sized to correspond at least approximately to the shape and size of the implanted valve 200. The cavity 763 includes a pair of channels 767 defined in the sidewalls 765. As discussed above, the inlet port of the programmable valve 200 can be connected to an inflow catheter, and the outlet port of the programmable valve 200 can be connected to a drainage catheter. The channels 767 can be sized and arranged such that, when the valve programmer 760 is placed over the implanted valve 200 on the patient's head, the channels 767 align with the inflow catheter and the drainage catheter, thereby assisting to correctly align the valve programmer 760 with the implanted valve 200.

After the user sets the desired pressure setpoint on the programmer 760, the user places the programmer 760 on top of the valve 200. Next, the user presses the programming button 769 on the front edge of the programmer 760 to start the programming.

Figure 23E:
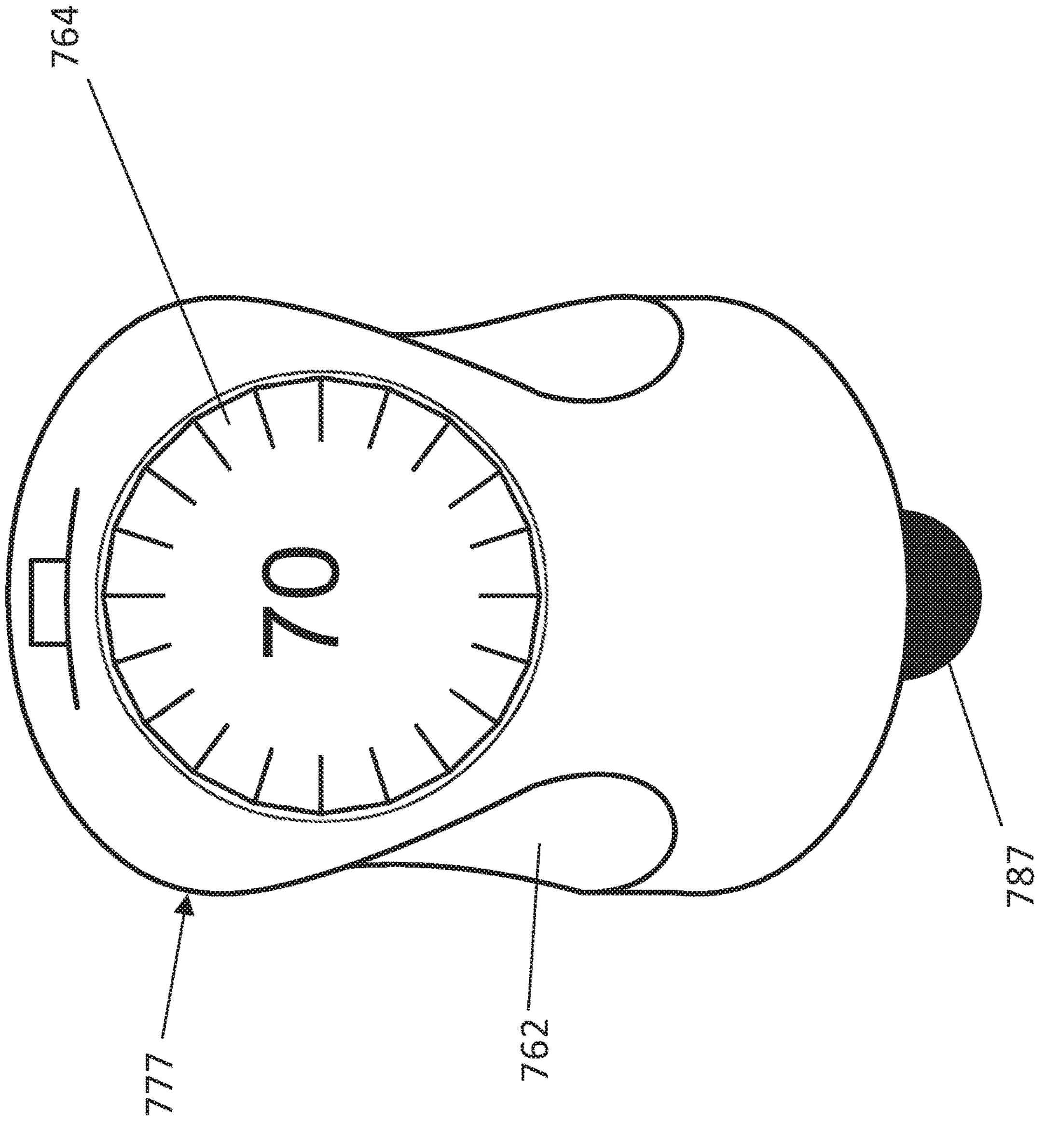
FIG. 23E is a diagram showing a top plan view of another example of a valve programmer according to aspects of the present invention.

FIG. 23E shows a top view of a valve programmer 777. The valve programmer 777 has a housing 762 that can be held in a user's hand. The valve programmer 777 includes a user interface 764 that shows information such as the pressure setting, the battery status 770, and optionally other information. The valve programmer 777 includes a wheel 787 that is rotatable in a first direction to increase the pressure setpoint, and rotatable in a second direction to decrease the pressure setpoint. In FIG. 23E, the wheel partially extends horizontally beyond a side of the housing 762 so that it can be rotated by a user's finger.

Figure 24:
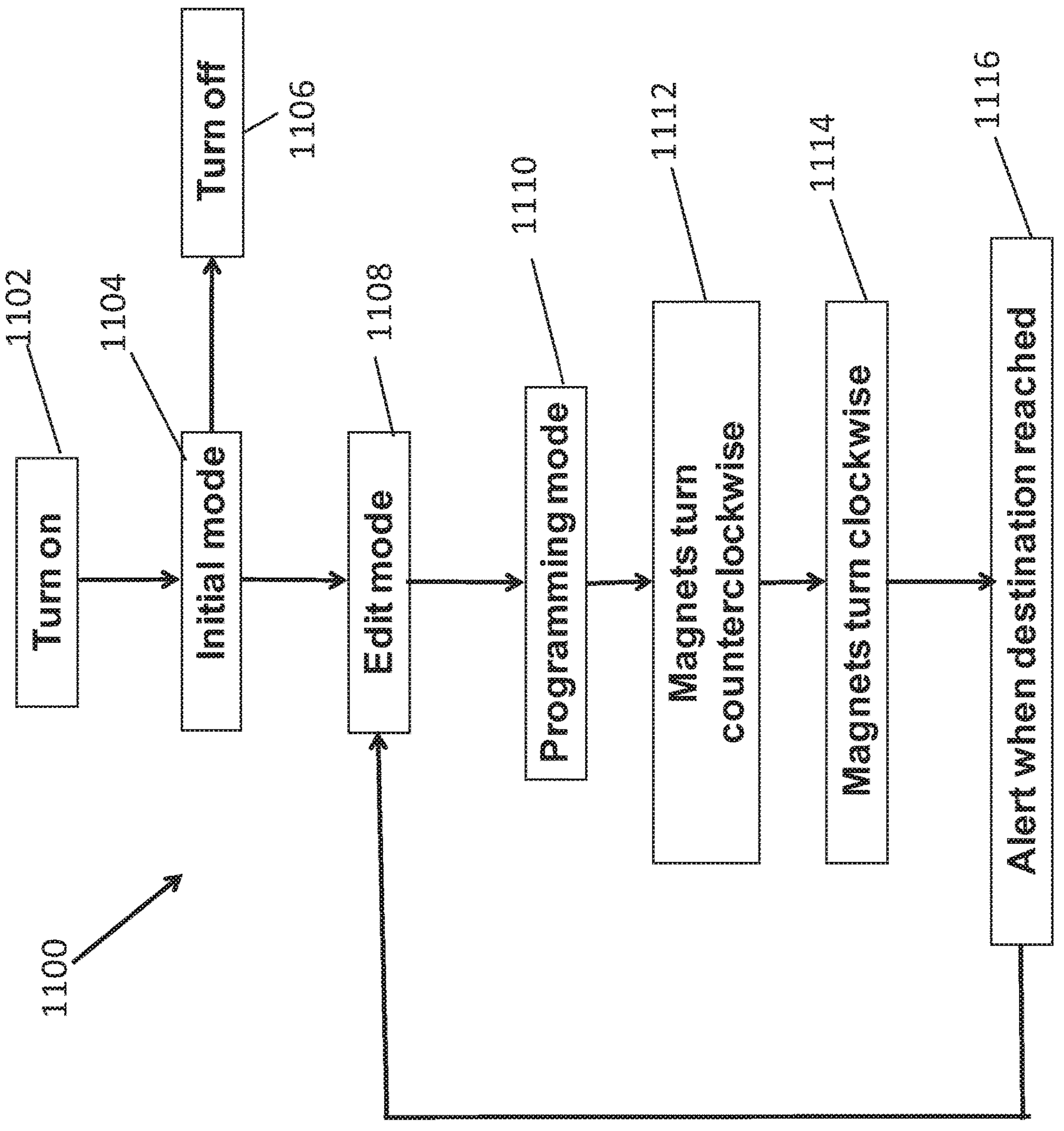
FIG. 24 is a flow diagram for one example of a method of operating the valve programmer of FIGS. 23A-D to program the pressure setting of an implantable valve according to aspects of the present invention.

FIG. 24 is a flow diagram illustrating an example of a method 1100 of operating a valve programmer 700, such as the valve programmer 760 of FIGS. 23A-D or the valve programmer 777 of FIG. 23E. In step 1102, the user turns on the valve programmer 760 by pressing the on/off button 772 on the programmer. In some embodiments, the valve programmer 760 turns on when the user presses and holds the on/off button 772 for two seconds. After being turned on, the valve programmer 760 proceeds to the initial mode at step 1104. In the initial mode, the valve programmer 760 performs a self-test in which the motor turns counterclockwise and counts the steps for one turn, and compares the number of steps to the number of steps that should be needed for one turn. In some embodiments, the motor self-test is always active when the motor is turning. In some embodiments, the valve programmer display (user interface screen) 764 shows all icons for three seconds in step 1104. If the charge on the valve programmer battery is too low, the valve programmer 760 proceeds to step 1106, in which a battery status indicator 770 or indicator flashes on the user interface screen 764 and the valve programmer 760 turns off. In some examples, if the battery charge of the valve programmer 760 is low, the battery status indicator 770 flashes slowly on the programmer display 764, and if the battery charge is extremely low, the battery status indicator 770 flashes quickly on the programmer display 764.

If the battery charge is sufficient, the valve programmer 760 proceeds to step 1108, which is edit mode. The battery status may be displayed on the user interface screen 764, as discussed above. In the edit mode of step 1108, an icon showing that the edit mode is enabled appears on the programmer display 764. In the edit mode, a user can press the increase button 761*a* or the decrease button 761*b* to increase or decrease the valve programmer's pressure setpoint for the implanted valve 200. In other examples in which the valve programmer 760 includes a wheel 787 for pressure setpoint adjustment rather than the buttons 761*a*, 761*b*, the user can rotate the wheel in step 1108 to select a desired pressure setting.

Once the pressure setpoint has been selected, the valve programmer 760 is ready to be used to program an implanted valve 200. Accordingly, the user can place the valve programmer 760 on a patient's head over the implanted valve 200, using the shape of the housing 762 to correctly align the valve programmer 760 with the implanted valve 200, as discussed above. To begin programming the valve 200, the user presses the programming button 769 on the valve programmer 760, and the programming mode at step 1110 is entered. In the programming mode, the programmer display 764 may show the selected pressure setpoint value along with a lock symbol, as shown in FIG. 23A, for example.

In one example, to ensure an accurate pressure setting of the valve 200, the valve programmer 700 can be configured to first actuate rotation of the magnet guide 714 in one direction (e.g., counter-clockwise) to set the valve 200 to its fully closed position, and then begin a sequence of rotations in the opposite direction (e.g., clockwise) to set the valve 200 to the selected pressure setting entered by the user. Accordingly, in certain embodiments after predetermined time period, for example, one second, the valve programmer 760 proceeds to step 1112, in which the programmer magnets turn counterclockwise to initialize the valve 200. For example, the programmer magnets of a permanent magnet assembly 710*a*, 710*b* can first be rotated counterclockwise for approximately six turns so that the cam of the programmable valve 200 is at its lowest position. After the initial position is reached, the valve programmer 760 proceeds to step 1114, in which the programmer magnets start to turn clockwise. While the programmer magnets are turning the valve programmer 760 displays the current and final positions for the valve 200. When the final position of the programmer magnets is reached, the valve programmer 760 proceeds to step 1116, in which an alert, such as an audible alert, indicates that the selected pressure setpoint has been reached. After a predetermined time period, for example, three seconds, the valve programmer 760 returns to the edit mode of step 1108. At this stage, a user can turn the valve programmer 760 off by pressing an on/off button 772. In some embodiments, after a certain time period, e.g., 60 seconds, of no user interaction with the valve programmer 760, the valve programmer 760 turns off automatically.

Figure 25A:
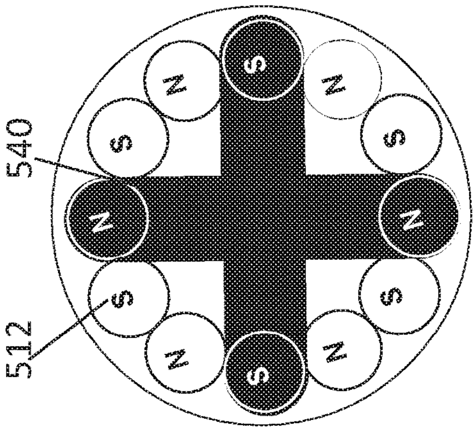
FIGS. 25A-C are diagrams showing examples of different configurations of stators in combination with a twelve-magnet rotor, according to aspects of the invention.
Figure 25B:
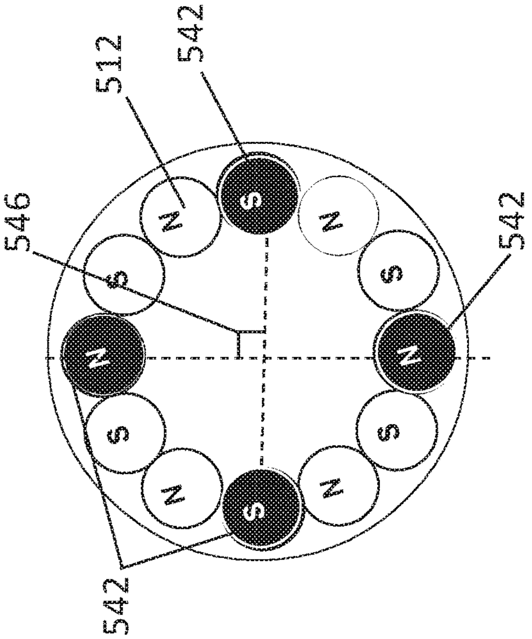
Figure 25C:
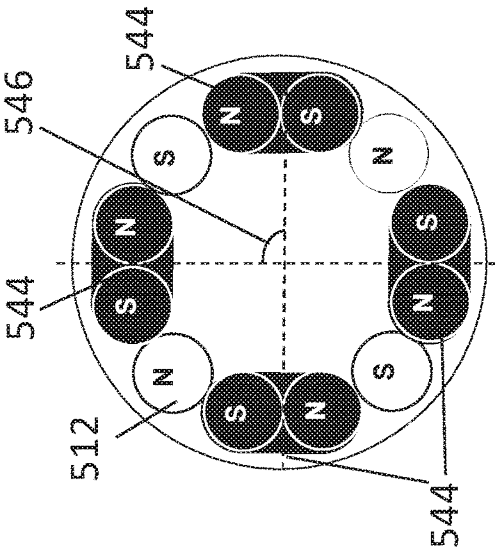

Returning to FIGS. 14, 16A-H, 18A-H, 21A-E, and 22, in the above-discussed examples, the stator 528 has an X shape, as shown in FIG. 14, for example, and is a "solid" or unitary structure. The shape of the stator 528 may vary between a + shape, with a 90° angle between the stator arms to a very narrow X shape, for example. In addition, according to certain embodiments, the stator 528 can be implemented using a plurality of discrete stator elements, rather than a single solid or unitary structure. FIGS. 25A-C illustrate three schematic examples of stators with different shapes, in combination with a twelve-magnet rotor. FIG. 25A shows an example of a +-shaped unitary stator 540. FIG. 25B shows an example of a stator including four stator elements 542 placed beneath the rotor magnet elements 512 at positions roughly corresponding to the tips of the four stator arms in the example shown in FIG. 25A. In the example illustrated in FIG. 25B, the four stator elements 542 are configured as four circular dots; however, the stator elements may have any of variety of other shapes. For example, FIG. 25C illustrates another example of the stator including four stator elements 544 configured as "double circular dots" or extended ovals. In other examples, the stator elements 542 or 544 may be squares or rectangles, or have other geometric or non-geometric shapes.

Figure 26A:
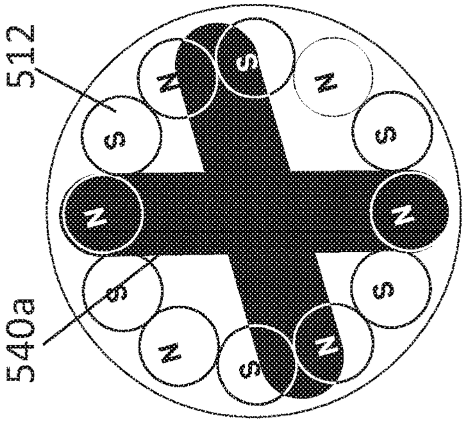
FIGS. 26A-C are diagrams showing further examples of stators in combination with a twelve-magnet rotor, according to aspects of the invention.
Figure 26B:
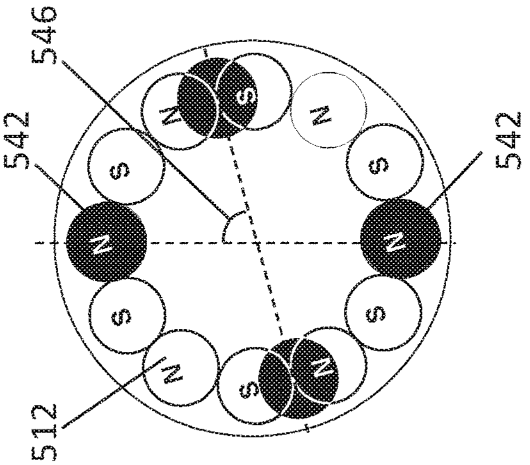
Figure 26C:
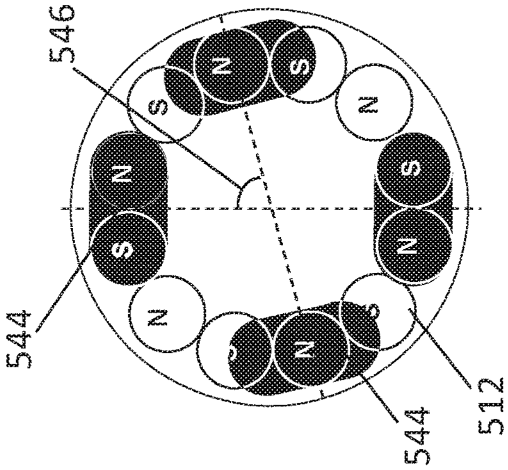

In each of the examples shown in FIGS. 25A-C, the angle 546 between the stator "arms" is approximately 90°; however, as discussed above, the angle 546 may vary. As will be appreciated by those skilled in the art, given the benefit of this disclosure, the angle 546 may have any value between 90° and a non-zero smallest value (an angular value of zero or very close to zero results in a two-arm stator, instead of a four-arm stator, which would change the operation of the magnetic motor) that may be dependent on the size of the stator 528 and the configuration of the rotor 510, for example. FIGS. 26A-C illustrate further examples of stators in which the angle 546 is approximately 75°. In particular, FIG. 26A shows an example of an X-shaped unitary stator 540*a* in which the angle between the closer two stator arms is 75° and therefore the complimentary angle between the further apart stator arms is 105°. FIGS. 26B and 26C show examples stators including four discrete stator elements 542 and 544, respectively, in which the angle 546 is 75°. In certain examples, the value of the angle 546 may be selected based at least in part on achieving resistance to external non-programming magnetic fields (e.g., from an MRI or other magnetic field generator not associated with the valve programmer) and desired movement of the rotor 510 (e.g., specific incremental movements of the rotor that correspond to particular incremental pressure settings of the valve). In certain examples, it may be desirable to configure the stator 528 such that the motor has a relatively high cogging torque. Cogging torque corresponds to the force required to keep the rotor 510 in a particular position. A high cogging torque may increase the motor's resistance or immunity to external non-programming magnetic fields, and can also prevent the rotor 510 from being moved by the counterforce of the spring 400.

The use of discrete stator elements 542 or 544, rather than a solid stator, reduces the amount of magnetic material as compared to the examples of the stator 540, 540*a* as exemplified in FIGS. 25A and 26A. The magnetization of the stator elements 542 or 544 from an external magnetic field acts to rotate the rotor 510 in a similar manner as described above with reference to FIGS. 16A-H, 18A-H, 21A-E, and 22. The rotation of the rotor 510 may be accomplished with either external electro-magnets, such as discussed above and shown in FIG. 13, for example, or with external permanent magnets, such as discussed above and shown in FIGS. 20A and 20B, for example. In certain examples, the stator elements 542 may each be slightly larger (e.g., larger diameter if circular) than the rotor magnet elements 512. For example, if the rotor magnet elements 512 have a diameter of 1.3 mm, the circular stator elements 542 shown in FIG. 25B or 26B may have a diameter of 1.4 mm.

As discussed above, according to certain embodiments the programmable valve 200 can include a magnetic indicator mechanism by which to allow a doctor, for example, to determine a pressure setting of the valve 200 using an external magnetic sensor, such as a Hall sensor for example, without requiring X-rays or other imaging techniques. In particular, in certain examples the magnetic motor can include one or more reference or indicator magnets that indicate a position of the rotor 510. As discussed above, the rotor position is directly correlated to the pressure setting of the programmable valve 200. Accordingly, in some examples the external valve programmer 700 can include a magnetic sensor configured to read or detect the pressure setting of the implanted valve 200 based on the indicator magnet(s). In other examples, a separate pressure reader can be provided, as discussed further below.

Figure 27:
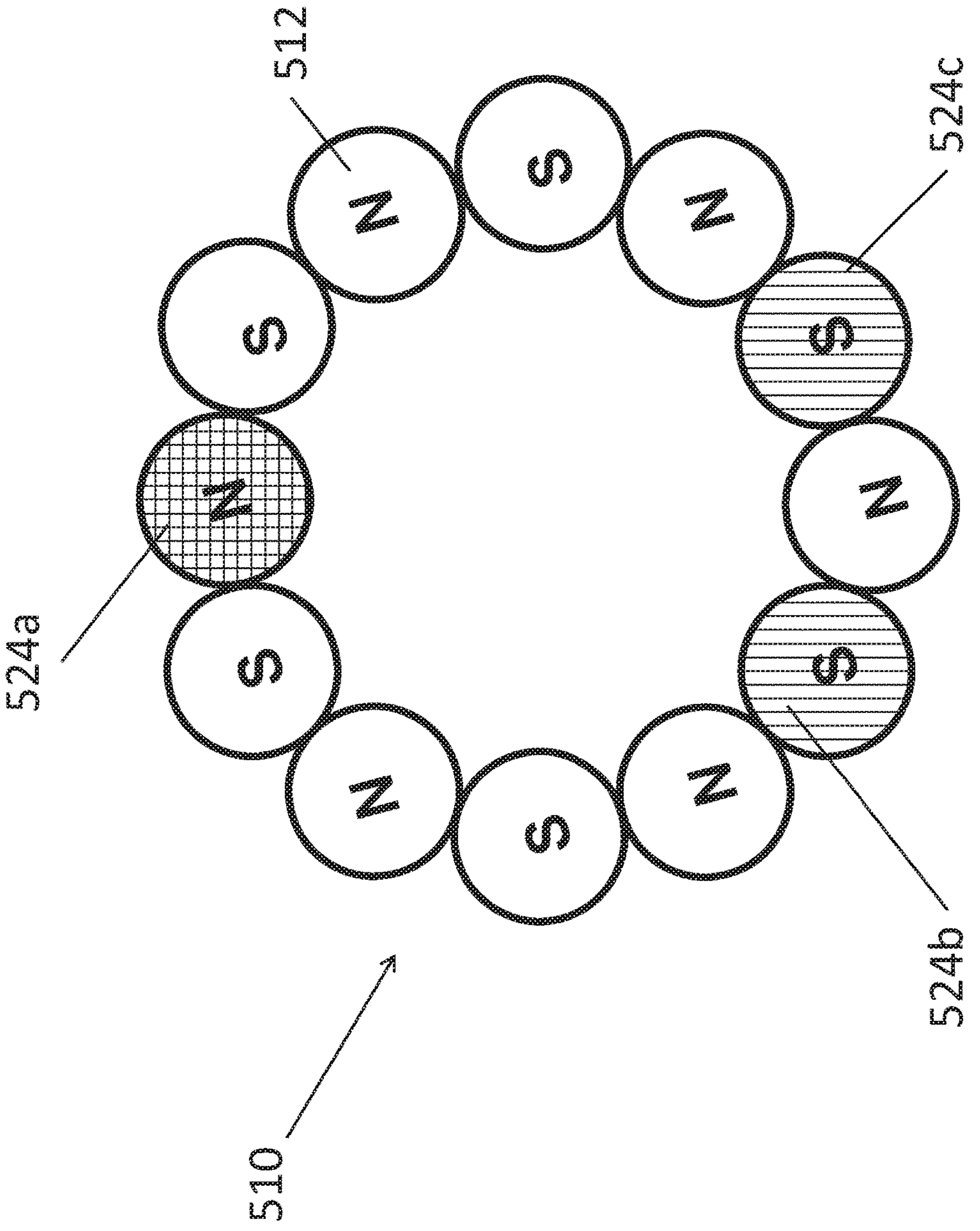
FIG. 27 is a diagram of one example of a rotor including reference magnet elements according to aspects of the invention.

According to certain embodiments, the indicator mechanism can be incorporated into the rotor 510. For example, as discussed above, the rotor 510 can include reference or positioning magnet elements 524 positioned on top of certain ones of the rotor magnet elements 512, as illustrated in FIGS. 4A, 5, 6A, and 14. FIG. 27 illustrates a schematic example of the rotor 510 including three reference magnet elements 524*a*, 524*b*, and 524*c* positioned above certain ones of the rotor magnet elements 512. In the illustrated example, reference magnet element 524*a* has north magnetic polarity, and reference magnet elements 524*b* and 524*c* are positioned approximately radially across from reference magnet element 524*a* (on either side of the rotor magnet element 512 that is directly radially opposite the reference magnet element 524*a*) and both have south magnetic polarity. As discussed above, the rotor magnet elements 512 are arranged with alternating magnetic polarity and such that each two rotor magnet elements 512 that are directly radially opposite one another have the same magnetic polarity. Accordingly, in order to provide a reference magnet that has both a north pole and a south pole and that spans the rotor 510, an arrangement of three reference magnet elements 524 such as that shown in FIG. 27 can be used. As discussed above, in other embodiments, the rotor 510 may include a number of rotor magnet elements 512 other than twelve. For example, the rotor 510 may include ten magnet elements. In such an example, only two reference magnet elements 524 may be used because the opposing rotor magnet elements in a ten-magnet rotor have opposite polarities, unlike the twelve-magnet rotor. In another example in which the rotor 510 includes ten magnet elements, four reference magnets (two opposingly-arranged pairs) can be used. Thus, as will be appreciated by those skilled in the art, given the benefit of this disclosure, various numbers and arrangements of reference magnet elements 524 can be used, at least partially based on the configuration of the rotor 510. Additionally, in certain embodiments, rather than including separate reference magnet elements 524, the rotor magnet elements 512 corresponding to the desired positions of the reference magnet elements can simply be made "taller" than the other rotor magnet elements, and thereby act as both rotor magnet elements that effect rotation of the rotor 510 and position-indicating magnets.

Figure 28A:
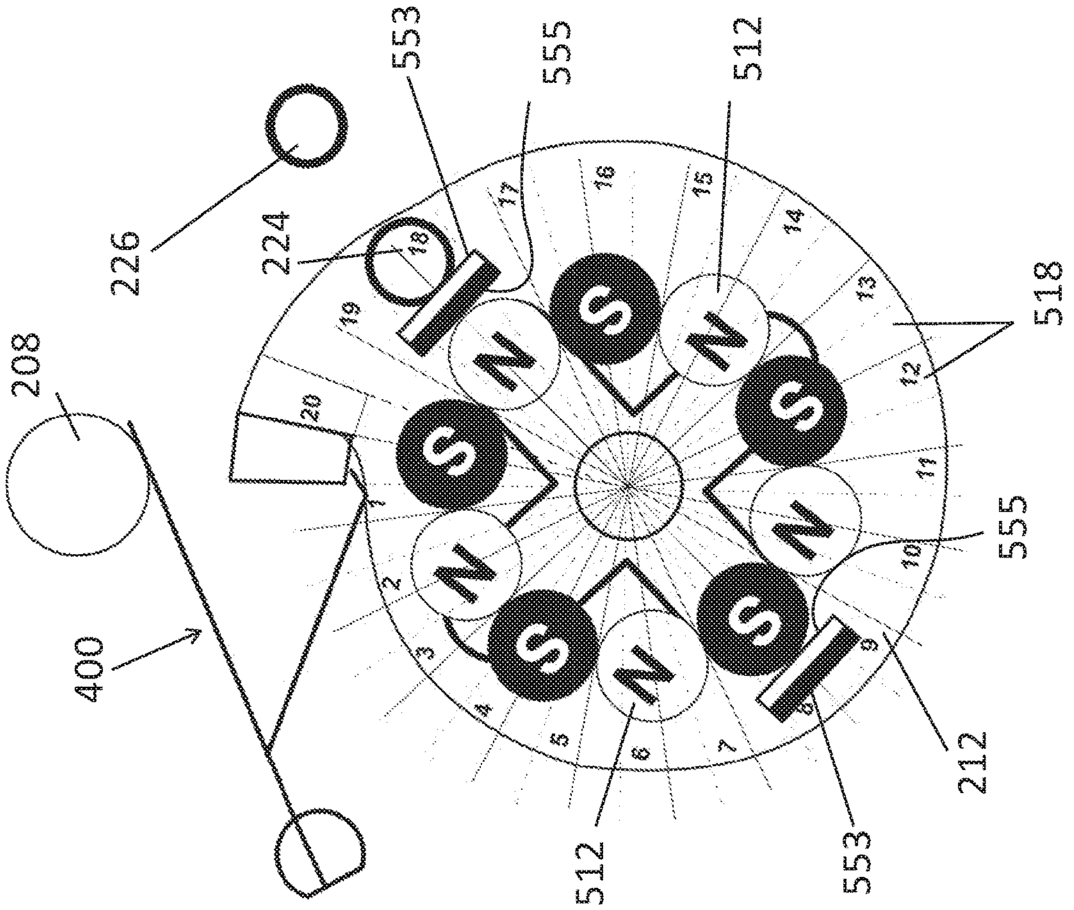
FIGS. 28A-C are diagrams showing further examples of a motor assembly including reference magnet elements according to aspects of the present invention.
Figure 28B:
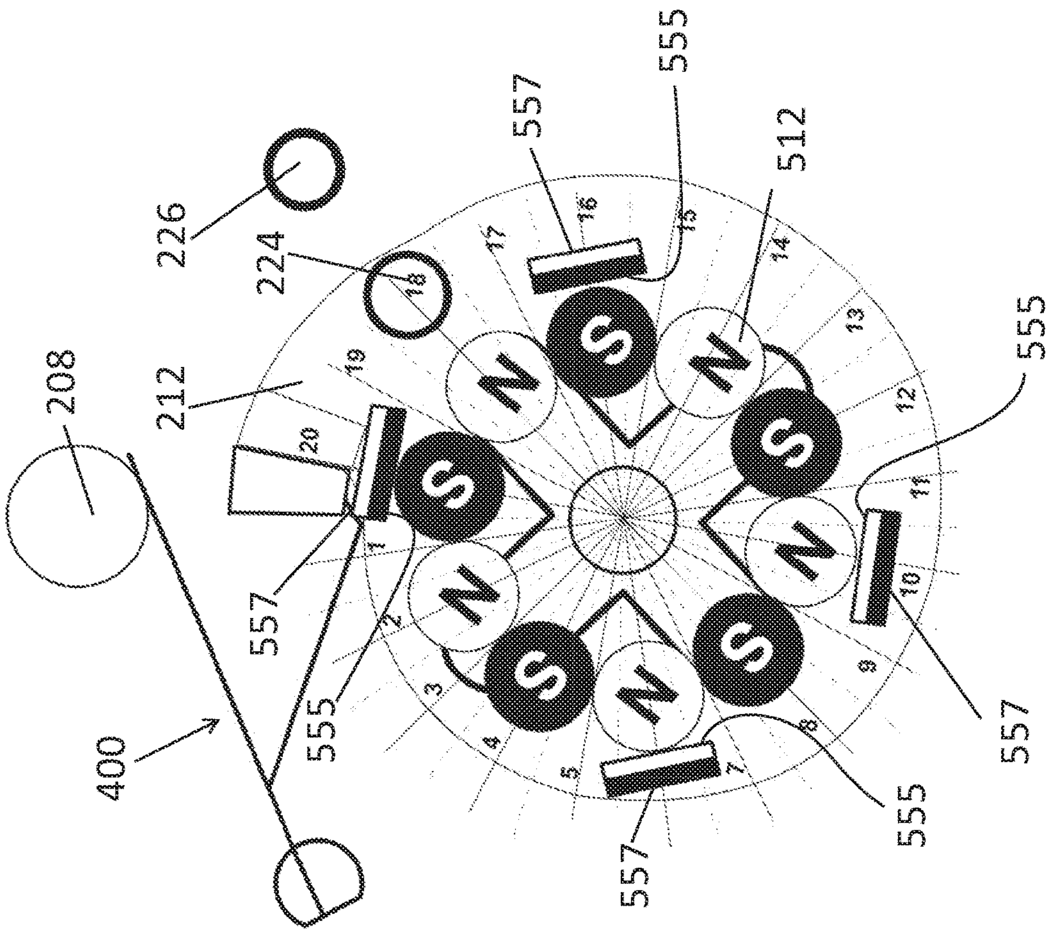
Figure 28C:
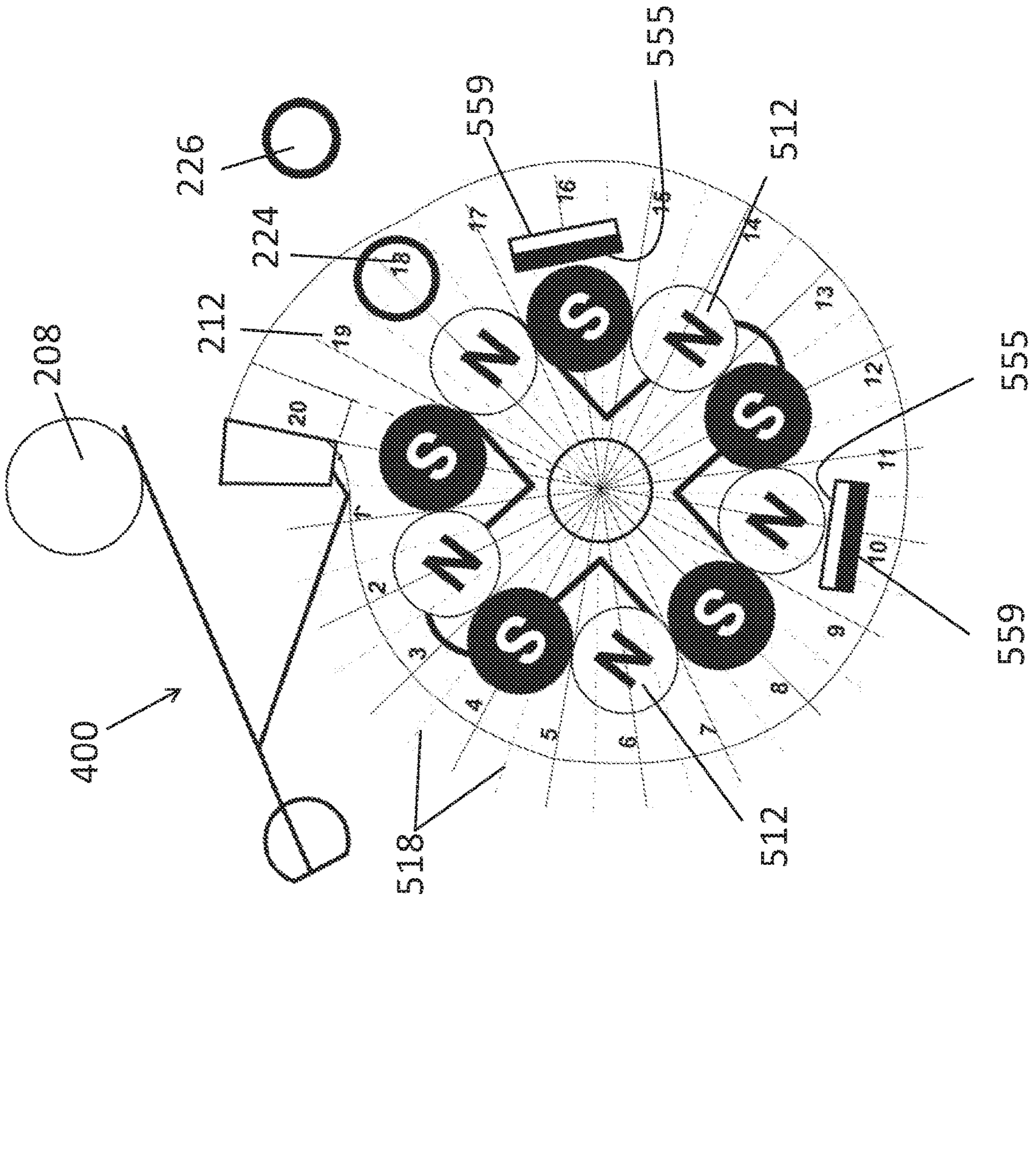

In other examples, instead of positioning the reference magnet elements 524 above the rotor magnet elements 512, as shown in FIGS. 4A, 5, 6A, 14, and 27, the reference or positioning magnet elements can be positioned to the side(s) of the rotor 510. FIGS. 28A-28C show examples of motor configurations in which vertically oriented (relative to the horizontally oriented rotor magnet elements 512) side positioning magnet elements 553 are positioned radially outward of the rotor magnet elements 512. As discussed further below with reference to FIG. 32, the positioning magnets orient an indicator magnet (not shown in FIGS. 28A-C) that can be read by the pressure reader 660, for example, to indicate a position of the rotor 510 and therefore the pressure setting of the valve 200. Referring to FIG. 28A, in there is illustrated an example in which two side positioning magnet elements 553 are provided. In this example, the polarity of the respective inner face 555 (i.e., face closer to the rotor magnet elements) of each side positioning magnet element 553 is opposite to the polarity of the top face of the adjacent rotor magnet element 512. In some embodiments, each side positioning magnet 553 has, for example, a 1.0 millimeter diameter and a height of 0.3 millimeters. FIG. 28B shows another example in which four side positioning magnet elements 557 are provided. In this example, the polarity of the respective inner face 555 of each side positioning magnet element 557 is the same as the polarity of the top face of the adjacent rotor magnet element 512. In some embodiments, each side positioning magnet 557 has, for example, a diameter of 0.85 millimeters and a height of 0.25 millimeters. FIG. 28C shows another example in which two side positioning magnet elements 559 are provided. In contrast to the example shown in FIG. 28A, in which the two side positioning magnet elements 553 are placed diametrically opposite one another across the rotor 510, in the example shown in FIG. 28C the two side positioning magnet elements are positioned in a same hemisphere of the rotor 510. The polarity of the respective inner side 555 of each side positioning magnet 559 is the same as the polarity of the top face of the adjacent rotor magnet. In some embodiments, each side positioning magnet 559 has, for example, a diameter of 1.0 millimeter and a height of 0.3 millimeters.

Figure 29:
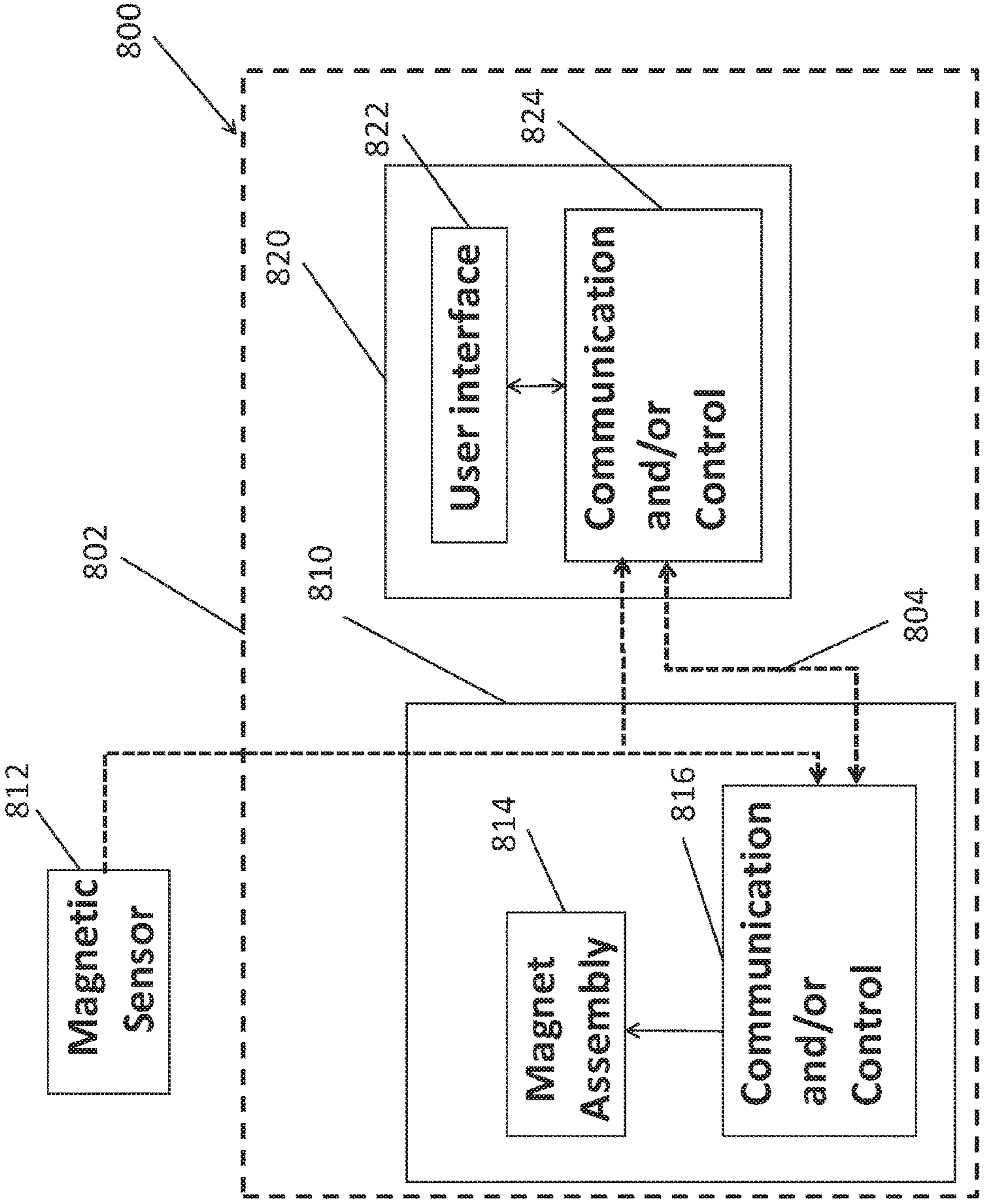
FIG. 29 is a block diagram of one example of an external valve programmer including a magnet sensor to detect the reference magnet elements, according to aspects of the invention.

Referring to FIG. 29 there is illustrated a block diagram of an example of an external valve programming assembly 800 that incorporates a magnetic sensor 812 configured to detect a magnetic signal from the reference magnet elements 524 or indicator magnet (positioned by the positioning magnet elements 553, 557, or 559, for example) and derive therefrom a position of the rotor 510 and corresponding pressure setting of the valve 200. As shown in FIG. 29, the valve programming assembly 800 can include a transmitter head 810 including a magnet assembly 814 (such as either the permanent magnet assembly 710 or a collection of electromagnets such as described above with reference to transmitter head 610) for adjusting the pressure setting of the valve 200 and communications/control circuitry 816 (such as an electronic communications port, motor, actuator, drive circuitry, and the like) as may be needed to control and operate the magnet assembly 814. The valve programming assembly 800 further includes a control device 820 that includes a user interface 822 to allow the user to view information, such as the current pressure setting of the valve 200, for example, and provide control commands, such as a desired pressure setting of the valve 200, for example, along with communications/control circuitry 824 as may be needed to operate the control device 820 or communicate with the transmitter head 810. In certain examples, the transmitter head 810 and control device 820 are separate and communicate via a wired or wireless communication link 804. In other examples, the transmitter head 810 and control device 820 can be packaged together, as indicated by dashed line 802, such as in the valve programmer 760. The magnetic sensor 812 can be in communication with either the communications/control circuitry 816 in the transmitter head 810 or the control device 820. In certain examples in which the magnet assembly 814 includes electromagnets that can be turned off, the magnetic sensor 812 may be packaged in the transmitter head 810. In other examples, it can be a packaged as a separate unit.

In one embodiment including the magnetic sensor 812 in the transmitter head 810 allows the pressure setting of the implanted valve 200 to be detected and communicated to the control device 820. In one example, the magnetic sensor 812 detects the position of the rotor 510 inside the valve 200 and translates the detected position into a pressure setting reading. Such correlations between rotational position and pressure settings can be determined for each valve according to a calibration process. The correlation can provide a look-up capability in which a rotational position can be translated into the pressure setting, and vice versa. A resolution of such pressure adjustment can be accomplished according to the techniques employed herein (e.g., based on a known size of the rotor magnet elements 512). Alternatively, or in addition, a selection of the spring type and/or spring constant in combination with a shape of the cam can be used to control pressure variations per rotational step. The magnetic sensor 812 can be a Hall sensor or compass, for example.

According to certain embodiments, a valve programming assembly, such as the valve programming assembly 800, can include a valve programmer, such as the valve programmer 760 discussed above, and a separate pressure reader. The pressure reader can be used to read the pressure setting of an implanted programmable valve 200, and the valve programmer 760 can be used to program the pressure setting of the implanted valve 200, as discussed above. The pressure reader can be a compass that includes a magnet configured to provide a pressure reading based on an orientation of the magnet. The compass can be a mechanical compass or an electronic compass.

In some embodiments, the pressure reader can be handheld. In some embodiments, the pressure reader is electronic. In certain examples the pressure reader can have a physical appearance that is very similar to that of the valve programmer 760, for example.

Figure 30A:
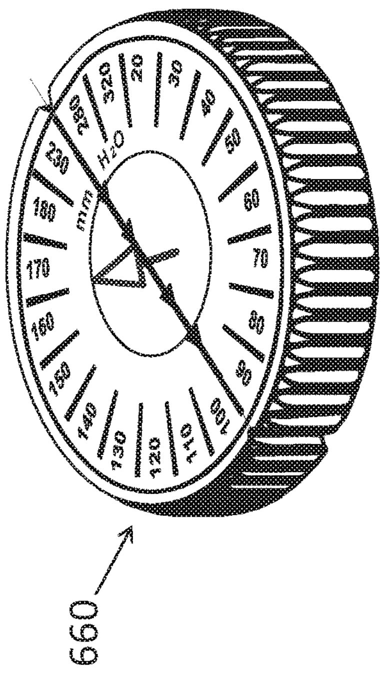
FIG. 30A is a perspective view of one example of a pressure reader according to aspects of the present invention.
Figure 30B:
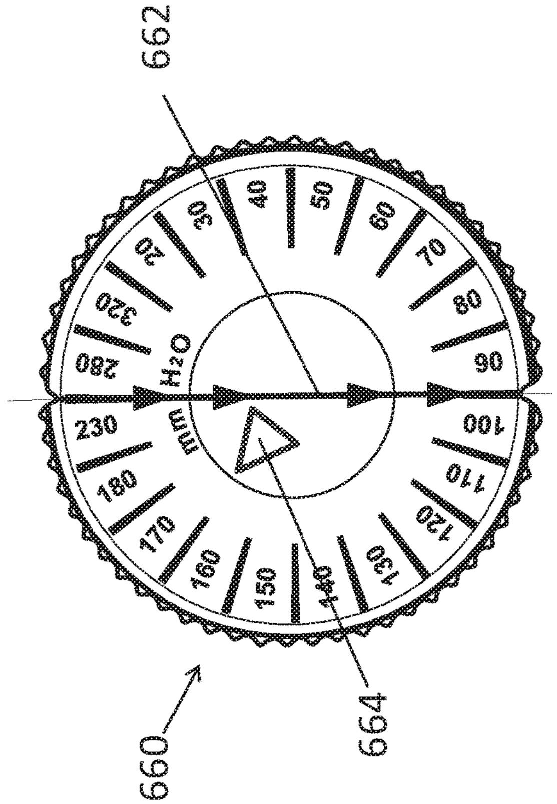
FIG. 30B is a top plan view of the pressure reader of FIG. 30A.

FIGS. 30A and 30B illustrate an example of a pressure reader 660 according to certain embodiments. FIG. 30A is a perspective view of the pressure reader 660 and FIG. 30B is a top view. A magnet of the pressure reader 660 is oriented with respect to the valve 200 by placing the pressure reader 660 over an implanted valve 200 such that the arrow 662 on the upper surface of the pressure reader 660 is aligned with the direction of the flow of fluid through the valve 200. The pressure reader 660 can be shaped and sized to facilitate its alignment with an implanted valve 200. For example, the pressure reader 660 can include a recess or cavity on its lower surface that corresponds to the size and shape of the implanted valve 200, similar to as discussed above with respect to the valve programmer 760. As shown in FIGS. 30A and 30B, the pressure reader 660 can have a circular shape, and may include a display having a range of pressure settings arranged around its circumference. The display can be mechanical or electronic. When the pressure reader 660 is placed over and aligned with the implanted valve 200, a pressure indicator 664 points to a pressure setting on the pressure reader 660 (as shown in FIG. 30B) that corresponds to a pressure setting of the valve 200, based on the reference magnet elements as discussed above.

Figure 31:
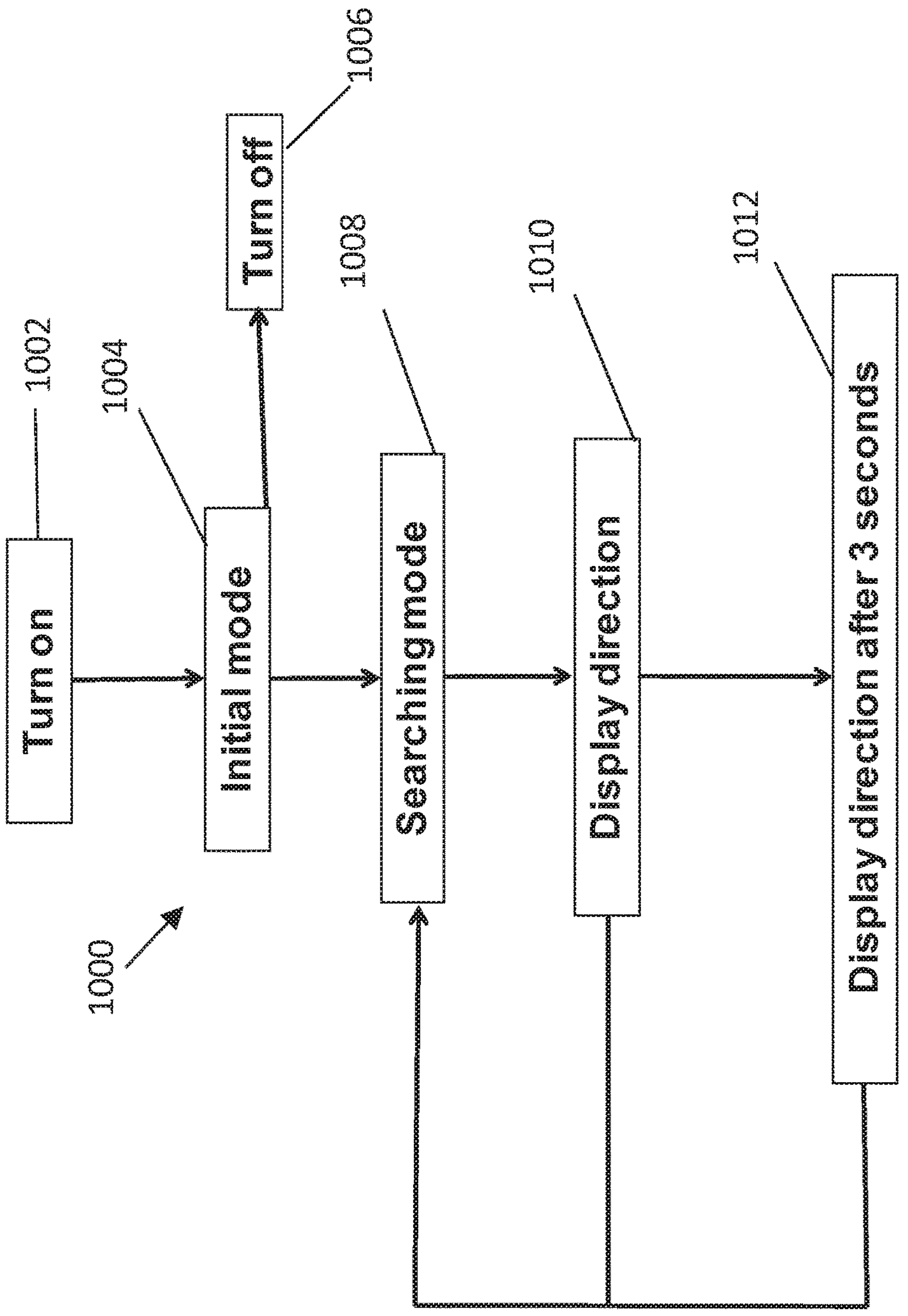
FIG. 31 is a flow diagram of one example of a method of operating a pressure reader to read the pressure setting of an implanted valve according to aspects of the present invention.

FIG. 31 shows an example of a method 1000 of operating a pressure reader such as the pressure reader 660 of FIGS. 30A-B. In step 1002, a user turns on the pressure reader 660. In some embodiments, the pressure reader 660 turns on when the user holds down an on/off button on the pressure reader for a predetermined time period, such as two seconds, for example. After being turned on, the pressure reader 660 proceeds to its initial operation mode in step 1004. In the initial mode of step 1004, the pressure reader sensor is calibrated to remove or compensate for the effects of the earth's magnetic field, for example. During the calibration, devices that may generate magnetic fields, such as the valve programmer 760, should be kept away from the pressure reader 660. In certain embodiments in which the pressure reader 660 includes an electronic display, the display can include a battery status indicator, similar to as described above with reference to the valve programmer 760. According to certain embodiments, if the battery charge of the pressure reader 660 is too low, the battery status indicator may flash, and then the pressure reader proceeds to step 1006, in which the pressure reader turns itself off. During operation of the pressure reader 660, if the battery charge becomes too low, the battery status indicator may flash to indicate to the user that the batteries of the pressure reader need to be replaced. If the battery charge becomes extremely low, the battery status indicator may begin to flash more quickly, and eventually the pressure reader 660 may turn itself off.

If the battery charge of the pressure reader 660 is sufficient, the pressure reader 660 performs the magnetic sensor calibration in step 1004, and then the pressure reader 660 proceeds to step 1008; searching mode. During the searching mode, the user may position the pressure reader 660 on a patient's head over an implanted valve 200. In the searching mode of step 1008, a search icon, such as a magnifying glass icon, may appear on an electronic display of the pressure reader 660 to show the user that the strength of the detected magnetic field is too low. This prompts the user to reposition the pressure reader 660 so that the detected magnetic field is stronger. If the detected magnetic field strength cannot be improved, this may indicate to the user that the pressure reader 660 magnetic field indication is not reliable.

When the pressure reader 660 detects a magnetic field with sufficient strength, the display of the pressure reader 660 shows the direction of the magnetic field of the valve at step 1010, which corresponds to the pressure setting of the valve. For example, as shown in FIG. 30A, the pressure indicator 664 can indicate the pressure setting of the valve 200. In examples in which the pressure reader 660 includes an electronic display, at step 1012, the pressure setting of the valve can be displayed and updated at periodic intervals, e.g., every two seconds. At either of step 1010 and step 1012, if the strength of the magnetic field is too low, the pressure reader 660 returns to step 1008, where the display can indicate that the pressure reader is searching for a sufficiently strong magnetic field.

A user can turn the pressure reader 660 on and off by pressing the on/off button on the pressure reader 660. In certain examples, after a predetermined time period, e.g., 360 seconds, the pressure reader 660 automatically turns off.

According to certain aspects, a kit for setting a pressure in a surgically-implantable shunt valve 200 can include the pressure reader 660 and the valve programmer 760. In other examples, a valve assembly 100 can include an integrated valve programmer 760 and pressure reader 660. In certain examples the pressure reader 660 and the valve programmer 760 can be provided to a user together as part of a kit, or they can be provided separately from each other. In some examples, the kit can further includes a surgically-implantable programmable shunt valve or valve assembly, such as a surgically-implantable shunt valve 200 or valve assembly 100, or another surgically-implantable programmable shunt valve or valve assembly.

In certain circumstances where the indicator mechanism rotates with the rotor 510 (e.g., where the indicator mechanism includes reference magnet elements 524 or certain ones of the rotor magnet elements, as discussed above), external, non-programming magnetic fields, such as the field from an MRI, for example, can act upon the indicator/reference magnets and undesirably induce a torque on the rotor 510. Accordingly, referring to FIG. 32 there is illustrated an example of the programmable valve showing an alternate example of an indicator mechanism that can avoid this occurrence. In the illustrated example, the indicator mechanism includes a positioning magnet 550 that is attached to the rotor 510, very close to the center of the rotor. The positioning magnet 550 can be used to orient an indicator magnet 552. Thus, the indicator mechanism further includes the indicator magnet 552 that is not attached to the rotor 510 and pivots freely on its own ruby bearing. In this example, both the positioning magnet 550 and the indicator magnet 552 have the shape of a ring and are diametrically magnetized. When the rotor 510 moves, the positioning magnet 550 rotates with the rotor 510 and magnetically attracts the indicator magnet 552 to make it rotate in the same amount. In one embodiment, the positioning magnet 550 has a very small magnetic force, and therefore the influence of an MRI or other non-programming magnetic field on the positioning magnet 550 will be insufficient to overcome the cogging torque of the motor and cause the rotor 510 to rotate. The magnetic force of the positioning magnet 550 is enough to attract the indicator magnet 552 to make it rotate in the same amount, as discussed above. The side positioning magnets 553, 557, and 559 discussed above may operate in a similar manner. In certain examples the indicator magnet 552 has a strong magnetic field, which can be read by a compass, Hall Sensor, or other magnet sensor 812 located outside of the patient's body (e.g., at a distance of 10 mm or more from the second indicator magnet). For example, the indicator magnet can be a single diametrically magnetized (i.e., having one north pole and one opposing south pole) magnet. The indicator magnet 552 may be influenced by a non-programming magnetic field, such as the field from an MRI; however, because the indicator magnet 552 can rotate freely on its own bearing, its movement does not cause the rotor 510 to rotate. When the non-programming magnetic field is removed (e.g., after the MRI scan is finished), the positioning magnet 550 will automatically re-orient the indicator magnet 552. By splitting the magnetic indicator mechanism into two separate magnets 550, 552, the valve 200 can have a magnet strong enough to be read from the outside and at the same time, a strong non-programming magnetic field, such as the one produced by an MRI, will not change the pressure setting of the valve 200 because the strong indicator magnet (552) is decoupled from the rotor 510.

In another embodiment, the positioning magnet 550 may be configured as two small disk magnets with the north and south polarities axially magnetized, rather than as a diametrically magnetized single ring magnet. In this case, for one of the two small disk magnets, the north is facing up towards the indicator magnet 552 and south is pointing away from the indicator magnet 552. For the other of the two small disk magnets, south is facing up towards the indicator magnet 552 and north faces away from the indicator magnet 552. The principle of operation of such a configuration is the same as discussed above with respect to creating a local magnetic field for identifying the position of the indicator magnet 552. The use of two very small disk magnets to implement the positioning magnet 550 may be preferred over a ring magnet in certain applications because this configuration may produce fewer artifacts in an image of the patient's body (as may be taken using an MRI or CT scan, for example).

The positioning magnet 550 can have a variety of other configurations as well. For example, as discussed above with reference to FIGS. 28A-C, in other embodiments the positioning magnet 550 can be replaced with any of the arrangements of positioning magnets 553, 557, or 559, or similar arrangements.

Figure 32:
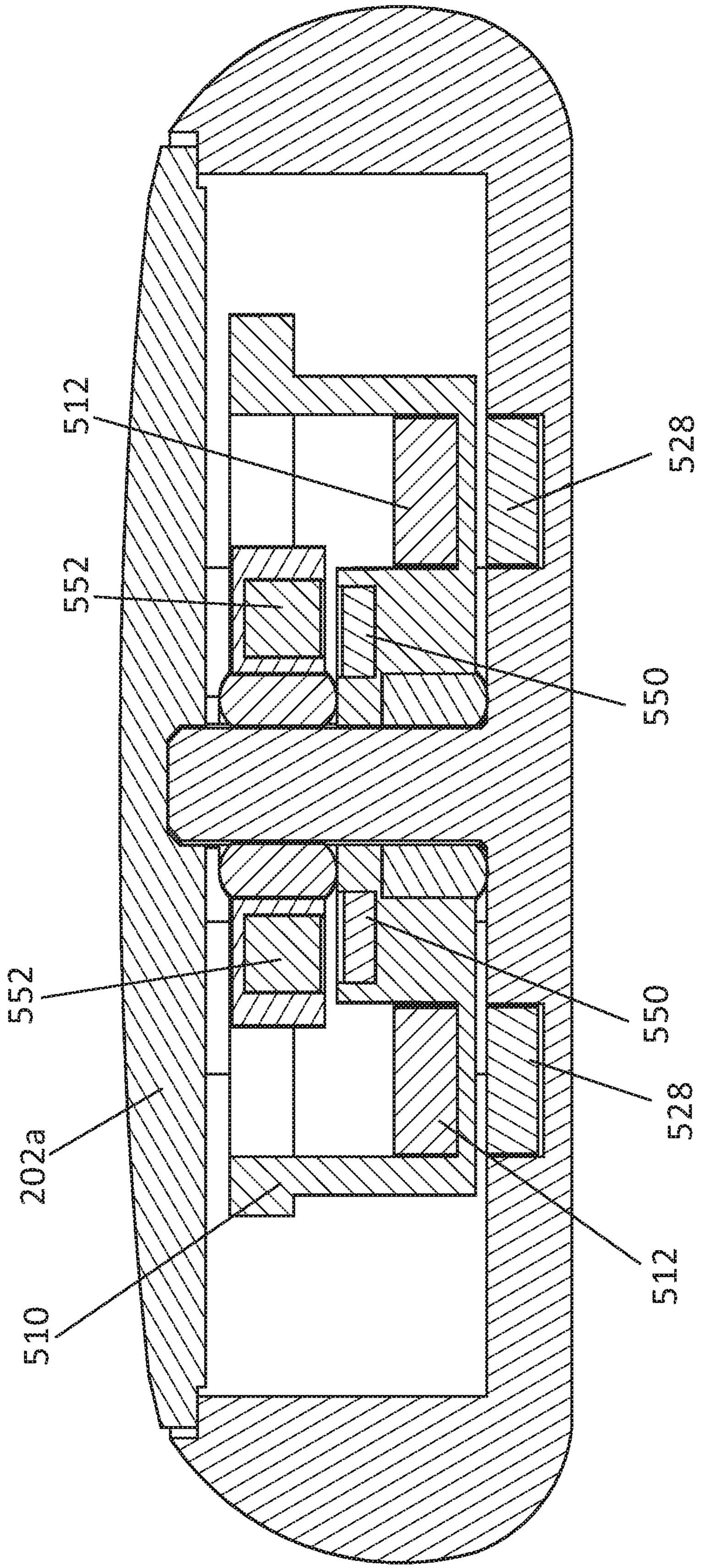
FIG. 32 is a diagram showing a cross-sectional view of another example of a motor including reference or position-indicating magnet elements according to aspects of the invention.

As discussed above, one limitation of conventional magnetically adjustable valves is that verifying a pressure setting can entail the use of an X-ray to detect a radiopaque marker on the implanted device. According to certain embodiments, an initial orientation of the rotor 510 can be determined with respect to a reference, such as the housing and/or casing, using an indication mechanism as discussed above. The pressure setting of the implanted valve 200 may be verified by placing a compass over the patient's head in the vicinity of the implanted valve 200. The needle of the compass will align itself with the direction of the indicator magnet 552, as illustrated in FIG. 32, or the reference magnet elements 524*a*-*c*, as illustrated in FIG. 27, thus indicating the position of the rotor 510. The physician is then able to determine the pressure setting of the valve 200 by considering the position of the rotor 510 relative to the housing 202.

Accordingly, the position of the rotor 510 may be precisely determined, and thereby a precise setting of the valve's threshold opening pressure may also be determined. In at least some embodiments, the rotor 510 is free to rotate in at least one direction, beyond one full revolution, with the pressure settings repeating for each revolution. In this manner, a position of the rotor 510 can uniquely identify a popping pressure.

As discussed above, in certain embodiments the magnetic motor is intrinsically immune or highly resistant to external non-programming magnetic fields, including even strong magnetic fields associated with an MRI. However, in certain instances, further immunity (for example, very high or complete assurance that no movement of the rotor 510 will occur) to very strong magnetic fields, such as those associated with an MRI, may be desired. Accordingly, in certain embodiments the programmable valve 200 may include a mechanical brake that prevents movement of the rotor 510 when the brake is applied.

Figure 33:
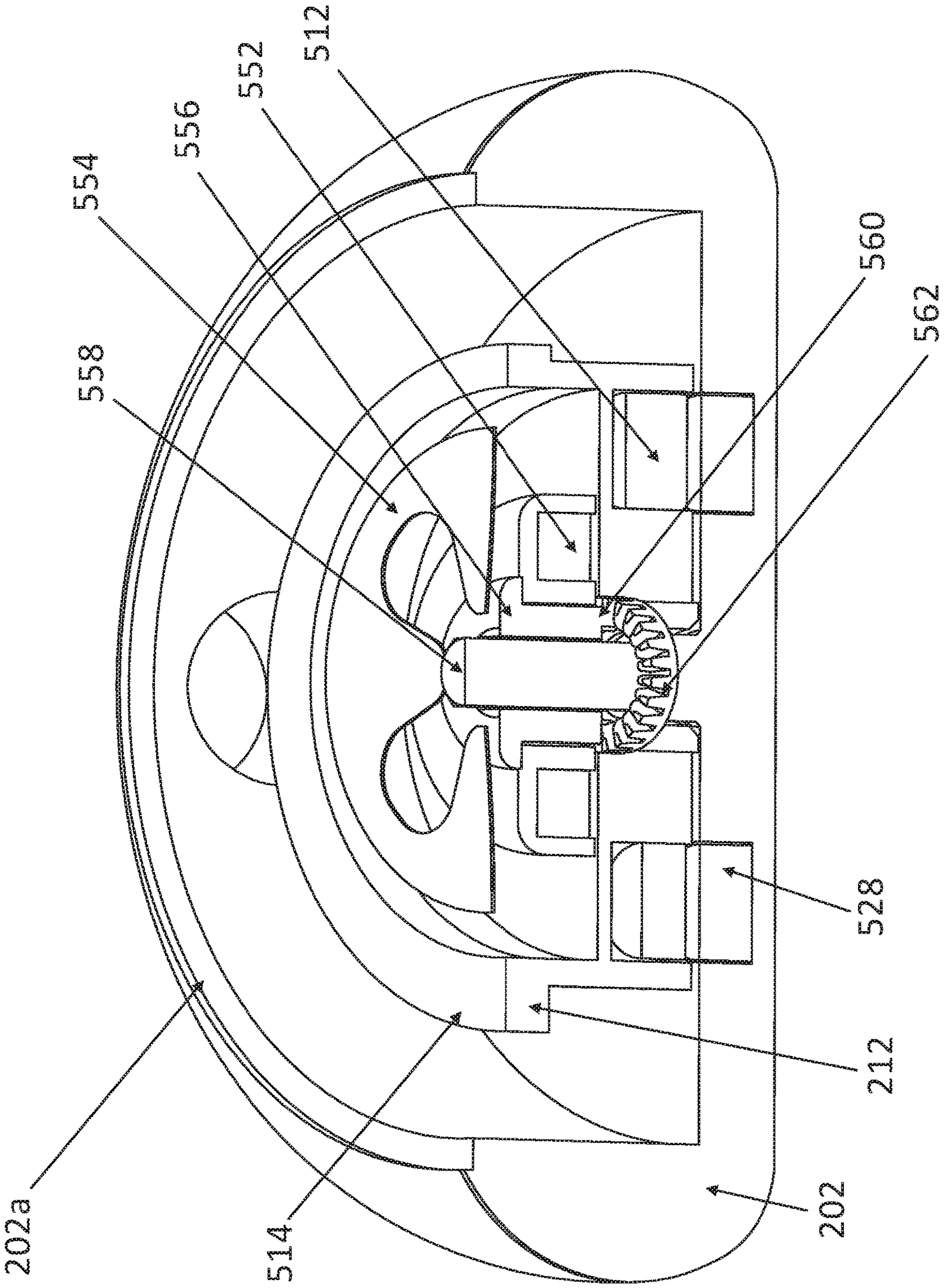
FIG. 33 is a partial cross-sectional three-dimensional view of one example of a programmable valve including a brake mechanism according to aspects of the invention.

Referring to FIG. 33, there is illustrated a partial cross-sectional view of one example of a magnetic motor including an example of a mechanical brake according to one embodiment. In this example the mechanical brake includes a brake spring 554 and a brake cylinder 556 that can rotate about a central pivot 558. In one example the brake cylinder is made of a thermoplastic, such as Polyoxymethylene, for example. The brake spring 554 may be made of metal, for example, stainless steel. In the example illustrated in FIG. 33, the brake spring 544 is a disc with a shaped cut-out; however, the brake spring can have a variety of different shapes, some examples of which are discussed further below. The brake cylinder 556 includes a plurality of brake cylinder teeth 560 that are configured to engage with a corresponding plurality of motor teeth 562. When the brake is in the locked position, the brake cylinder teeth 560 engage with the motor teeth 562 to prevent rotation of the rotor. When the brake is unlocked, the brake cylinder teeth 560 disengage with the motor teeth 562, allowing the rotor to rotate freely responsive to the applied programming magnetic field, as discussed above.

Figure 34:
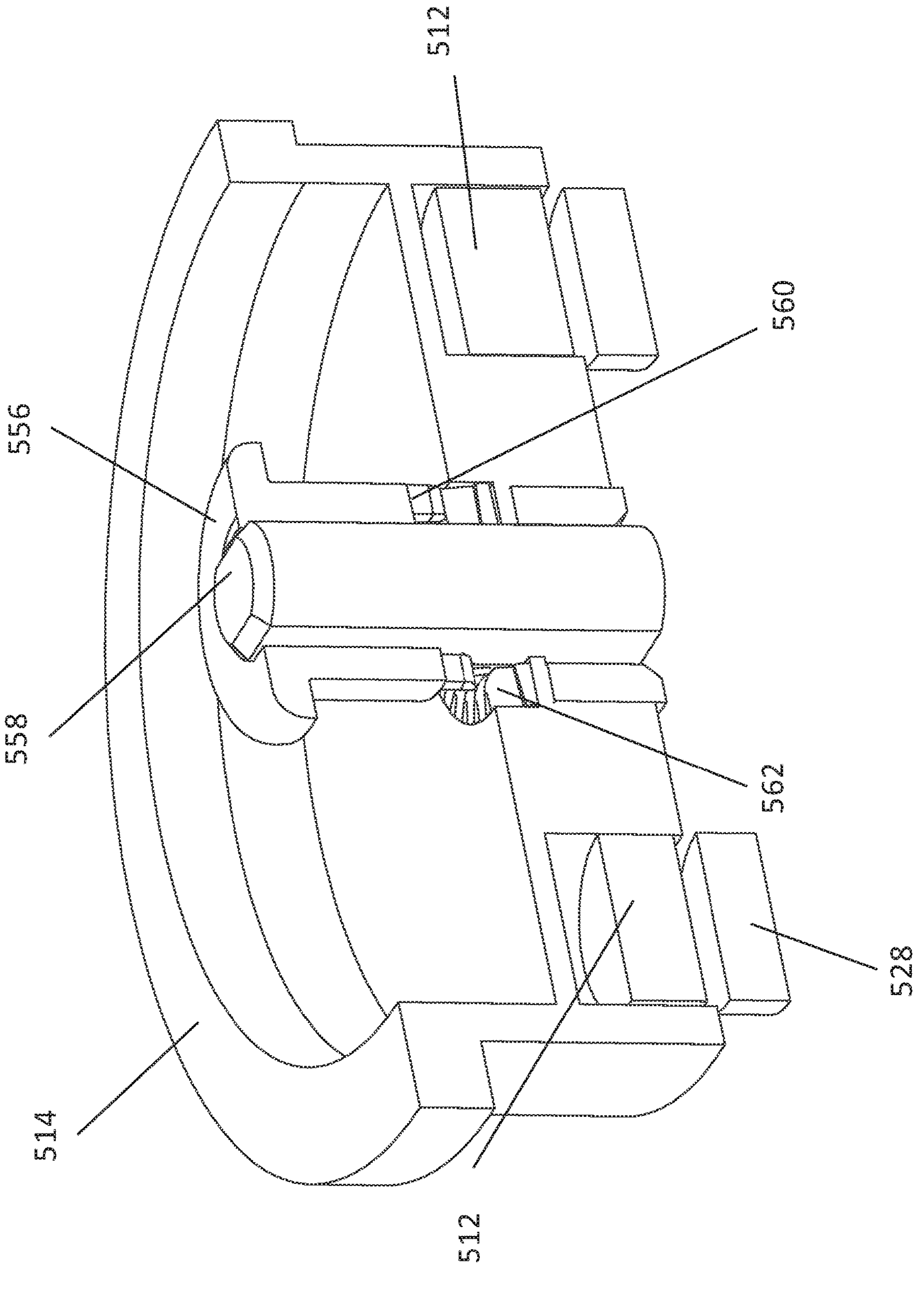
FIG. 34 is a schematic diagram showing certain aspects of an example of the brake mechanism according to aspects of the invention.

According to certain embodiments, locking and unlocking of the brake is achieved using the second indicator magnet 552. As discussed above, in certain examples the indicator magnet 552 is a single magnet that is diametrically magnetized. Accordingly, although small, the second indicator magnet can have a relatively strong magnetic field that can be used to release the brake. As discussed above, the second indicator magnet 552 is a freely rotating magnet, not tied to rotation of the rotor 510. If an external magnet is placed close to the second indicator magnet 552, the second indicator magnet will rotate to position itself according to the magnetic field of the external magnet. In examples in which the second indicator magnet 552 is a diametrically magnetized magnet, if the external magnet is axially magnetized, it will not pull the second indicator magnet towards itself, because one pole of the second indicator magnet will be attracted to the external magnet, while the other is repelled, and the two opposing forces balance one another. In contrast, if the external magnet is also diametrically magnetized, when it is placed close to the valve, the second indicator magnet 552 will rotate to position itself according to the magnetic field of the external magnet, and then will be attracted to the external magnet. Thus, the second indicator magnet 552 will be pulled upwards towards the external magnet. This upward movement can be used to disengage the brake, allowing rotation of the rotor 510 to program a pressure setting of the valve 200. When the external magnetic field is not applied, the brake spring 554 presses the brake cylinder down, keeping the brake cylinder teeth 560 engaged with the motor teeth 562. Referring to FIG. 34, in one example in which the central pivot 558 is circular, the brake cylinder 556 includes one or flat sections 563 on its interior wall surrounding the central pivot such that the brake cylinder can only move up and down and will not rotate. In other examples, other features or shapes can be employed to prevent rotation of the brake cylinder 556. FIG. 34 shows a schematic example of the motor 510 with the brake released.

Figure 35:
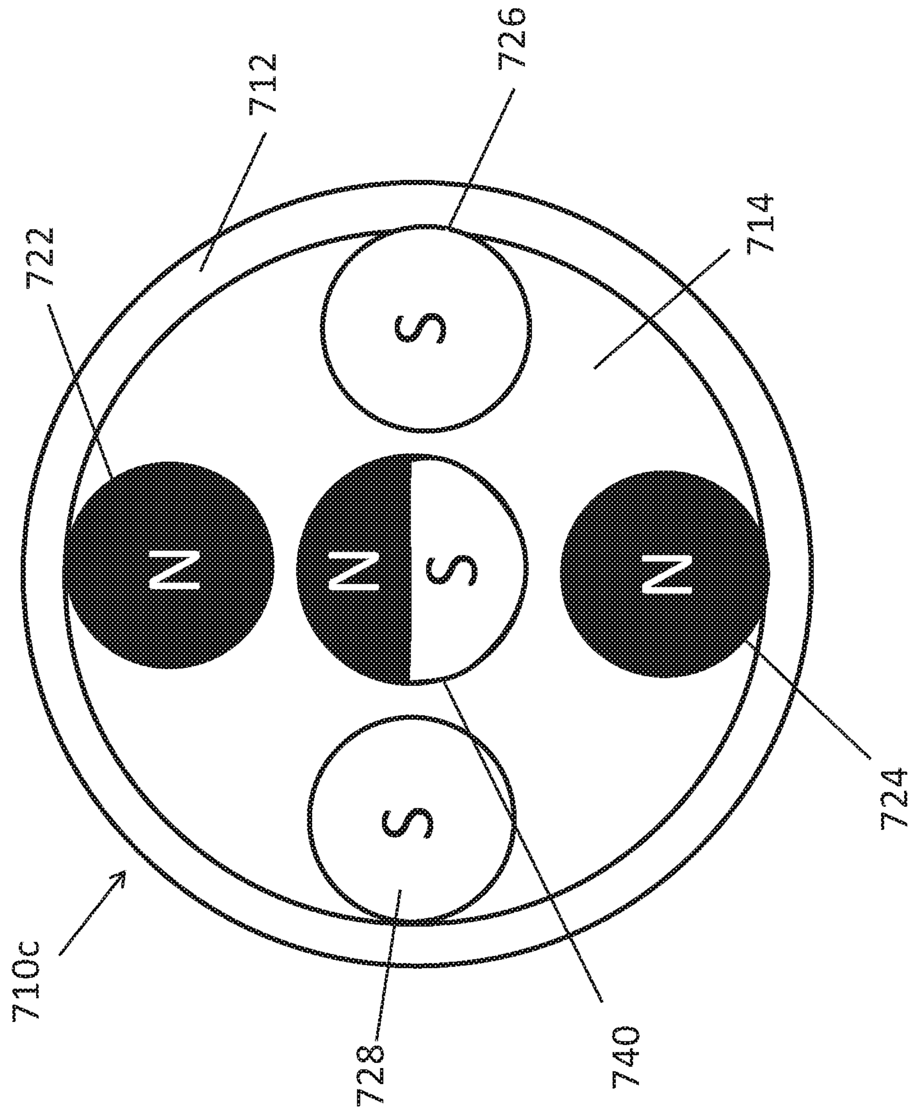
FIG. 35 is a diagram illustrating another example of a permanent magnet assembly for the external valve programmer of FIG. 19 incorporating a magnetic brake controller mechanism, according to aspects of the invention.

Accordingly, in certain embodiments, the permanent magnet assembly 710 of the valve programmer 700 includes a diametrically magnetized brake controller magnet that is used to disengage the brake when the valve programmer is placed in proximity to the valve 200 to program the pressure setting of the valve. FIG. 35 illustrates an example of a permanent magnet assembly 710*c* of the valve programmer 700 including a brake controller magnet 740. The example shown in FIG. 35 is similar to the permanent magnet assembly shown in FIG. 20A, and can be used to program a valve including a twelve-magnet rotor 510, as discussed above.

Figure 36:
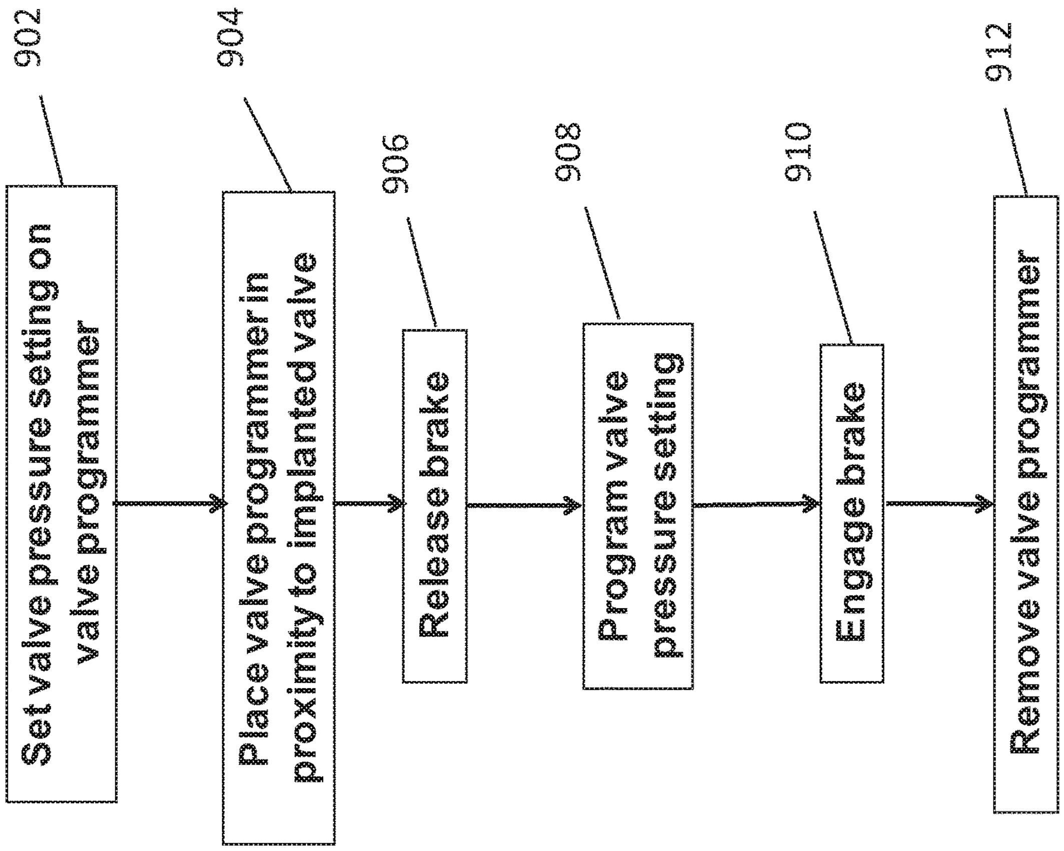
FIG. 36 is a flow diagram of one example of a method of programming an implanted programmable valve according to aspects of the invention.
Figure 37A:
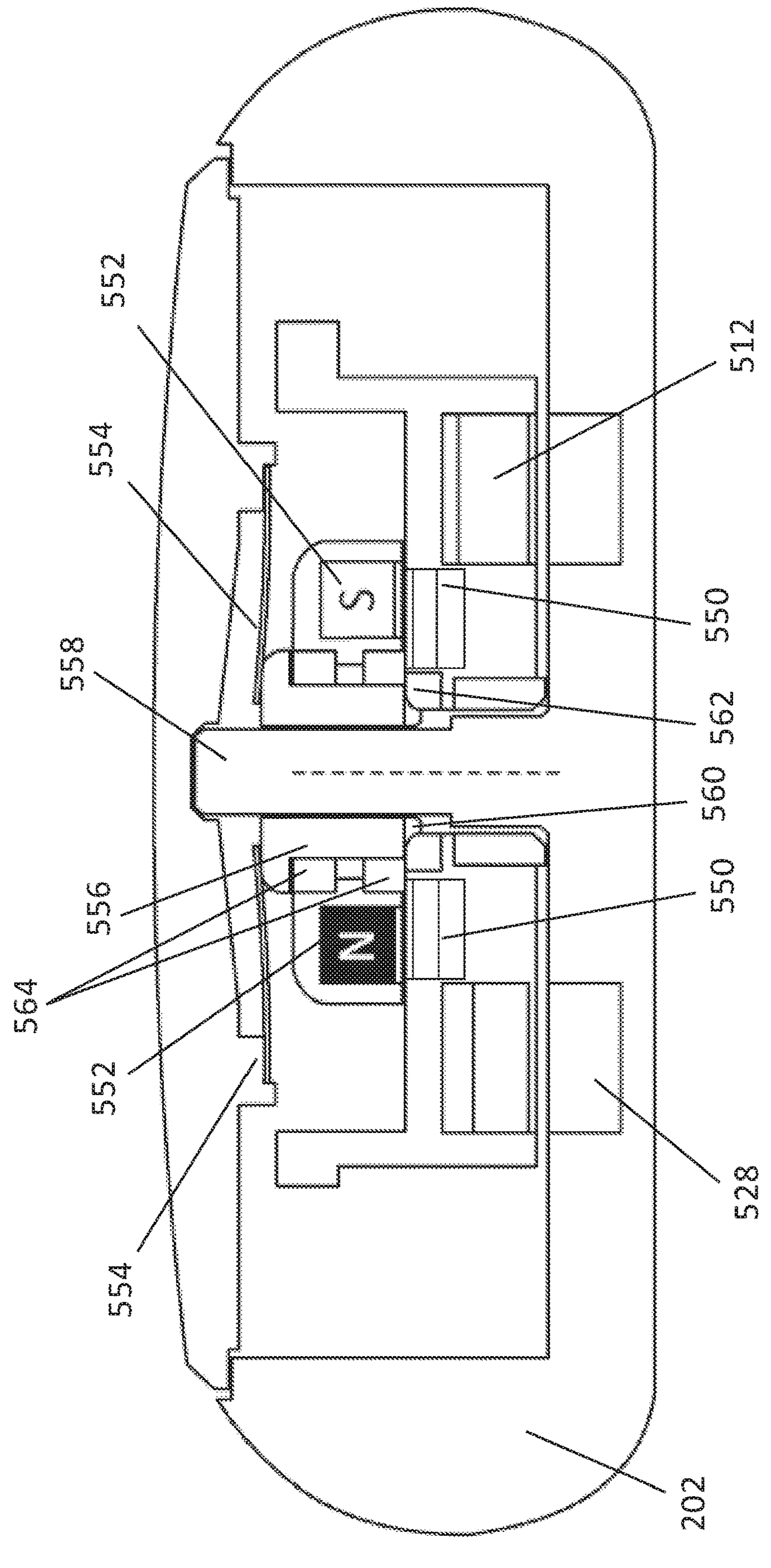
FIG. 37A is a cross-sectional view of one example of the programmable valve of FIG. 33 according to aspects of the invention showing the brake in the locked position.
Figure 37B:
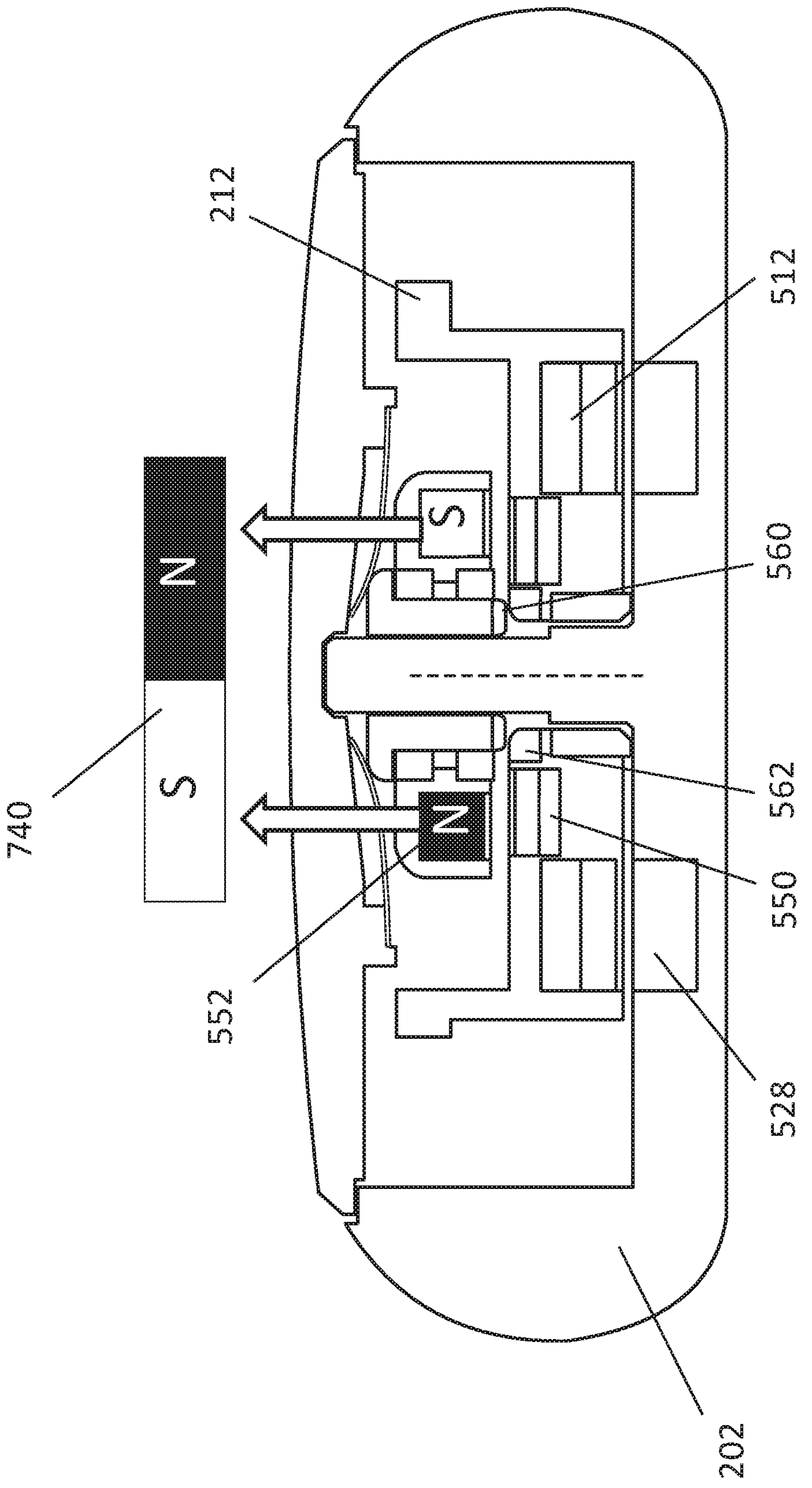
FIG. 37B is a corresponding cross-sectional view showing the brake in the unlocked position.

An example of operation of the motor and mechanical brake using an example of the valve programmer 700 including the magnet assembly 710*c* shown in FIG. 35 is discussed below with reference to FIGS. 36, 37A, and 37B. FIG. 36 is a flow diagram of one example of a method of programming the valve 200. FIG. 37A illustrates a cross-sectional view of one example of the valve 200 showing aspects of the magnetic motor and mechanical brake with the brake in the locked position, and FIG. 37B is a corresponding view showing the brake in the unlocked position.

Referring to FIG. 36, in a first step 902 of programming a pressure setting of the valve 200, a physician or other user selects the new pressure setting for the valve 200 directly on the valve programmer 700. In one example this can be achieved using a round display, such as illustrated in FIG. 11B, for example using a capacitive touch. In step 904, the physician/user places the valve programmer 700 one or near the patient's head in proximity to the implanted valve. As the start of the process, the brake is in the locked position, as shown for example in FIG. 37A. In some instances, it may be easier or more convenient for the physician/user to first select the desired pressure setting of the valve (step 902) and the place the valve programmer 700 in proximity to the patient's head (step 904); however, those skilled in the art will appreciate that steps 902 and 904 may be performed in the reverse order. In step 906 the brake in the valve 200 is released so that the valve programmer 700 can act on the magnetic motor to program the selected pressure setting. In one embodiment of the valve programmer 700 including the permanent magnet assembly 710*c*, the central diametrically magnetized brake controller magnet 740 is in a higher position than the other four magnets 722, 724, 726 and 728. For example, the brake controller magnet 740 can be held in this position by a spring pushing up. The physician/user can press down on the brake controller magnet 740 until it touches the skin on top of the implanted valve 200, for example. When the brake controller magnet 740 is touching the skin, it unlocks the brake by attracting the second indicator magnet 552, as discussed above and as shown in FIG. 37B, for example. In step 908 the valve programmer 700 is used to program the selected pressure setting of the valve 200 by magnetizing the stator 528 to cause rotation of the rotor 510 to the position corresponding to the selected pressure setting, as discussed above. In one example the valve programmer 700 can include a programming "on" switch that can be activated after the brake is released to allow programming to begin. The "on" switch can be built into permanent magnet assembly 710, and in particular, into the brake release mechanism. For example, the physician/user can push down slightly harder on the brake controller magnet 740 to trigger the switch to start the programming. In one example the switch must remain pressed while the programming is taking place. After the programming has been completed, an indication of completion can be provided to the physician/use, for example, an acoustic feedback can be heard. At this indication, the brake controller magnet 740 is released by the physician/user, and pushed back up into its inactive position by the spring. Upon removal of the magnetic field from the brake controller magnet 740, and the second indicator magnet 552 is no longer attracted upwards, and returns to its neutral position, and as a result, the brake cylinder 556 moves downward (pressed down by the brake spring 554), causing the brake cylinder teeth 560 to re-engage with the motor teeth 562 and lock the rotor 510 in the programmed position (step 910). The valve programmer 700 can then be removed from the patient's head (step 912).

Figure 38:
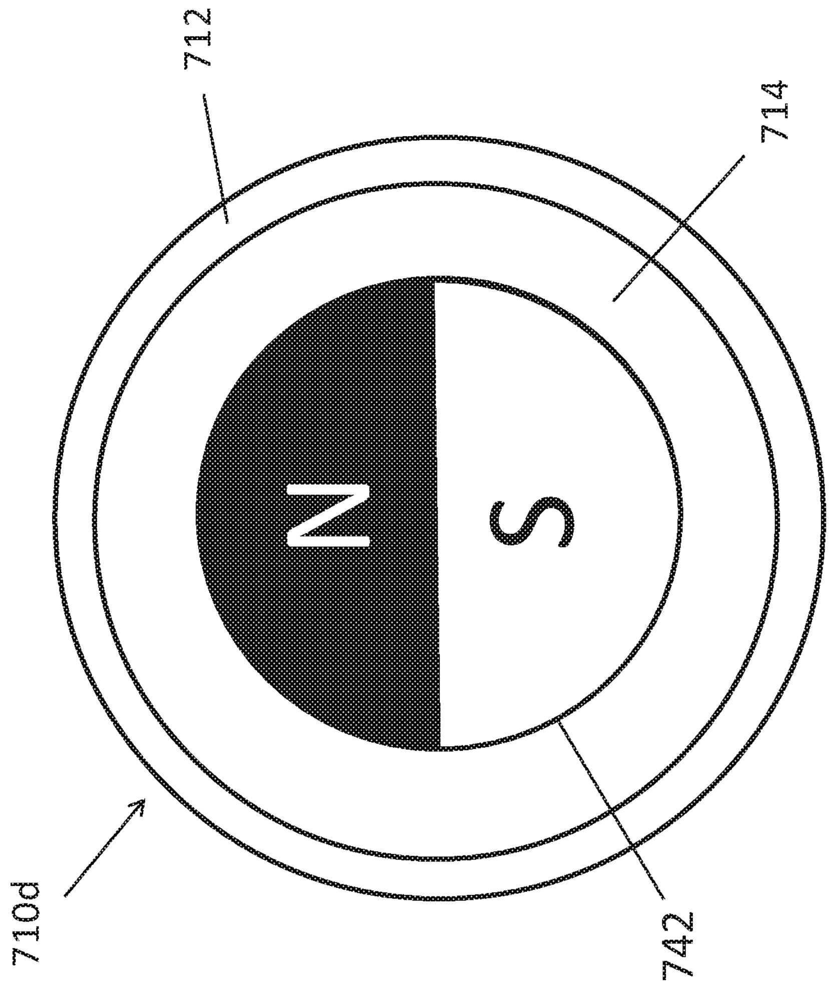
FIG. 38 is a diagram illustrating another example of a permanent magnet assembly for the external valve programmer of FIG. 19, according to aspects of the invention.

FIG. 38 illustrates another example of a magnet assembly 710*d* that can be used in the valve programmer 700 to program a valve including a ten-magnet rotor 510, for example. In this example, the two permanent magnets 732, 734 of the example permanent magnet assembly 710*b* shown in FIG. 20B have been replaced with a single diametrically magnetized controller magnet 742 which is used to both release the brake and program the pressure setting of the valve 200 as discussed above.

Figure 39:
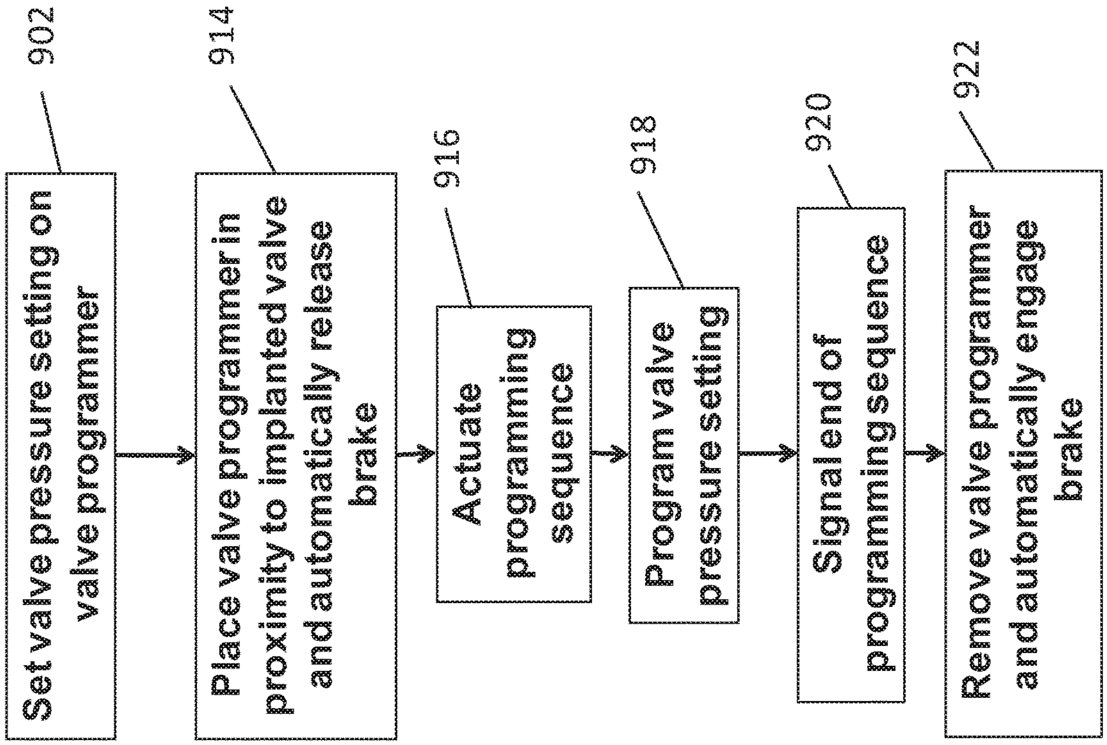
FIG. 39 is a flow diagram of another example of a method of programming an implanted programmable valve according to aspects of the invention.

FIG. 39 is a flow diagram of one example of a method of programming the valve 200 having a ten-magnet rotor 510 and using a valve programmer 200 that includes an example of the magnet assembly 710*d* shown in FIG. 38. As in the example discussed above, in a first step 902 of the programming sequence, the physician/user selects the new pressure setting for the valve 200 directly on the valve programmer 700. The physician/user can then place the valve programmer 700 in proximity to the implanted valve (step 914), which automatically releases the brake due to the presence of the diametrically magnetized controller magnet 742. In step 916 the physician/user actuates the programming sequence. This can be achieved by pressing a "start" button on the valve programmer 200, for example. In step 918 the valve programmer 700 is used to program the selected pressure setting of the valve 200 by magnetizing the stator 528 to cause rotation of the rotor 510 to the position corresponding to the selected pressure setting, as discussed above. When the programming sequence is complete, and the selected pressure setting has been reached, the programmer may signal completion of the programming sequence (step 920) using, for example, an acoustic or visual indicator (e.g., a beep, displaying a light or flashing light of a particular color, etc.). After the programming has been completed and the signal is heard/seen, the physician/user can remove the valve programmer from proximity to the patient's head, thereby automatically engaging the brake (step 922).

As shown in FIGS. 37A and 37B, in one embodiment the motor includes a pair of ruby bearings 564 that allow the second indicator magnet 552 to rotate with respect to the brake cylinder 556 for the purpose of indicating the position of the rotor 510 and the corresponding pressure setting of the valve 200, as discussed above. In one example the second indicator magnet 552 is contained in a casing that rotates on the ruby bearings 564.

Figure 40:
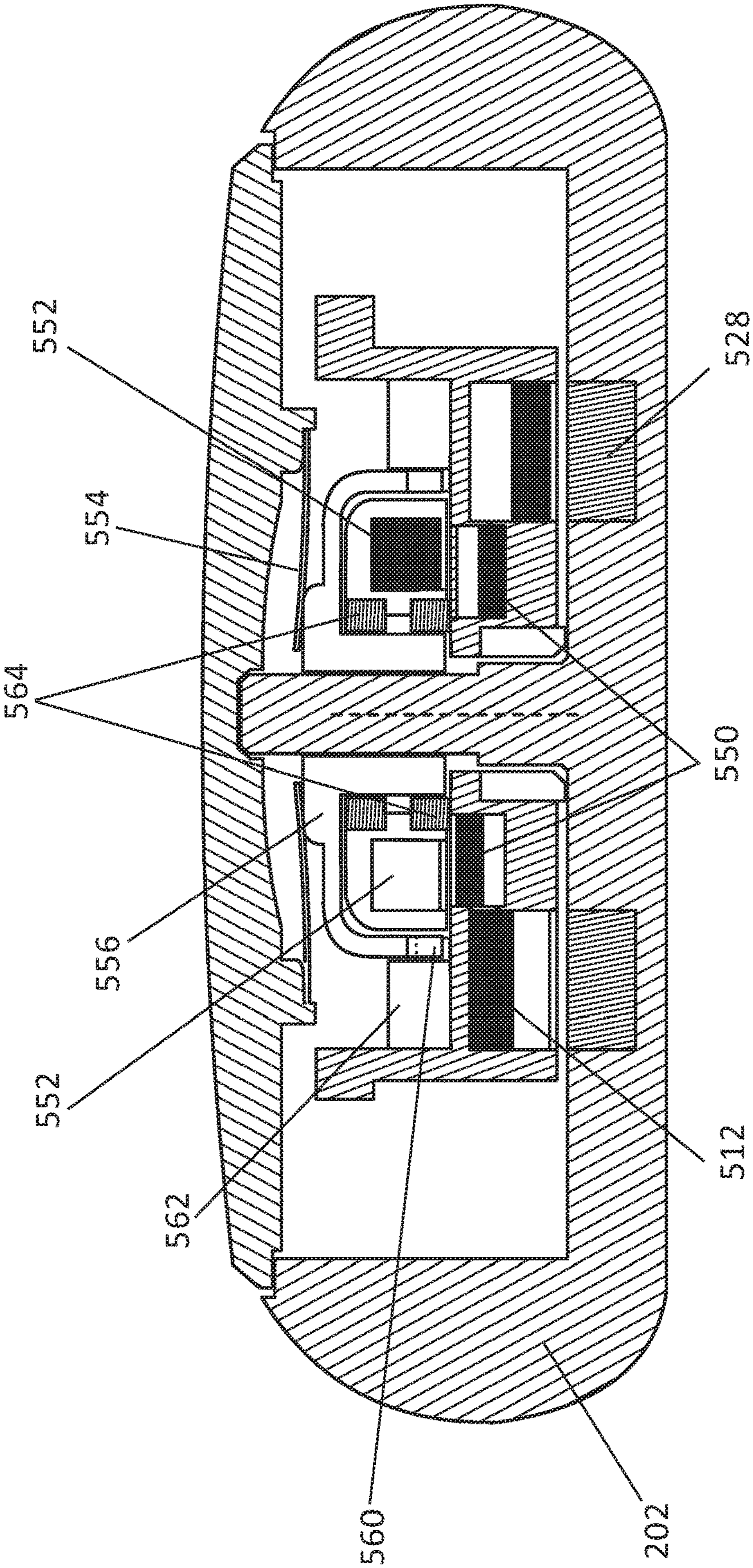
FIG. 40 is diagram showing another example of the programmable valve including a brake mechanism according to aspects of the invention.

As will be appreciated by those skilled in the art, given the benefit of this disclosure, the brake mechanism and its components can have a variety of different structural forms and be implemented in combination with any of various embodiments of the magnetic motor and its components. In the example shown in FIGS. 37A and 37B, the magnetic indicator mechanism includes the first indicator magnet(s) 550 that cooperate with the second indicator magnet 552. However, the brake mechanism can also be implemented with valve configurations in which one or more slightly "taller" rotor magnet elements 512, as discussed above, are used in combination with the second indicator magnet 552 for position sensing instead of the first indicator magnet(s) 550. In the example shown in FIG. 33, the brake cylinder teeth 560 and the motor teeth 562 are shown close to the central pivot 558, to the "inside" of and "below" the second indicator magnet 552. However, a wide variety of the other configurations can be implemented. For example, referring to FIG. 40 there is illustrated another embodiment in which the brake cylinder 556 spans the second indicator magnet 552 and the brake cylinder teeth 560 and corresponding motor teeth 562 are positioned to the "outside" of the second indicator magnet 552.

Figure 43:
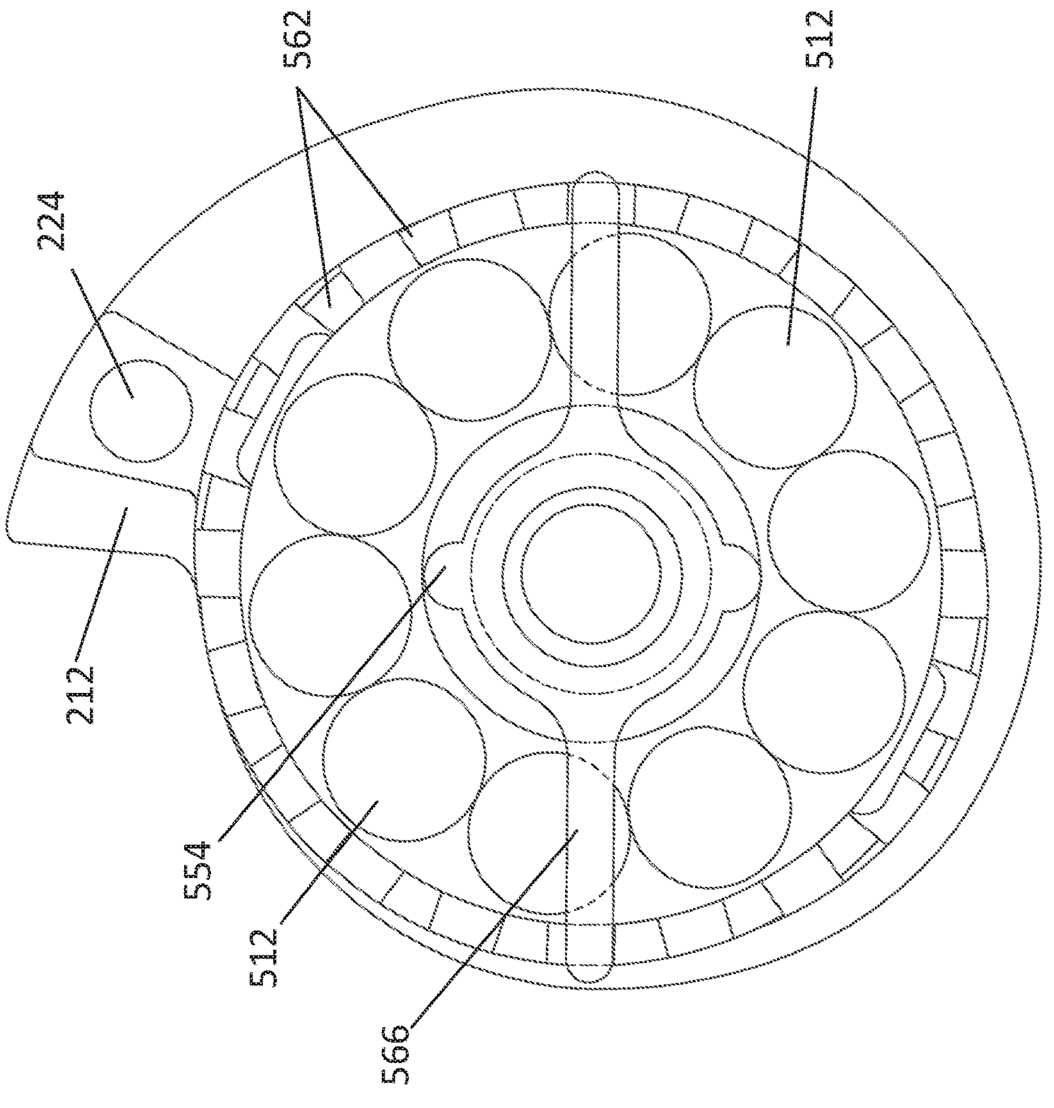
FIG. 43 is a plan view of another example of a motor assembly of a valve similar to that shown in FIG. 41, according to aspects of the invention.
Figure 44A:
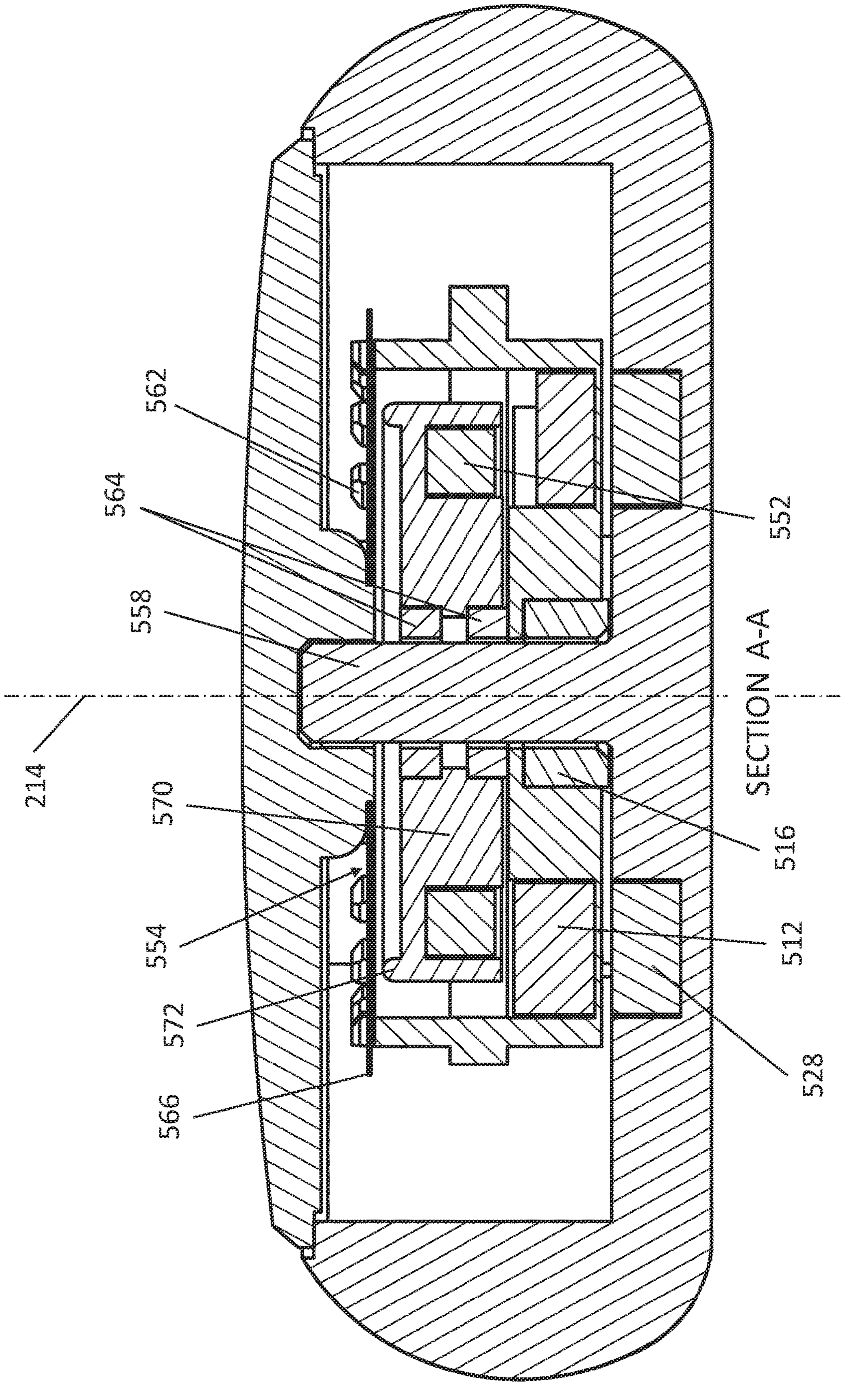
FIG. 44A is a cross-sectional view of the example of the valve shown in FIG. 42 taken along line A-A in FIG. 42.
Figure 44B:
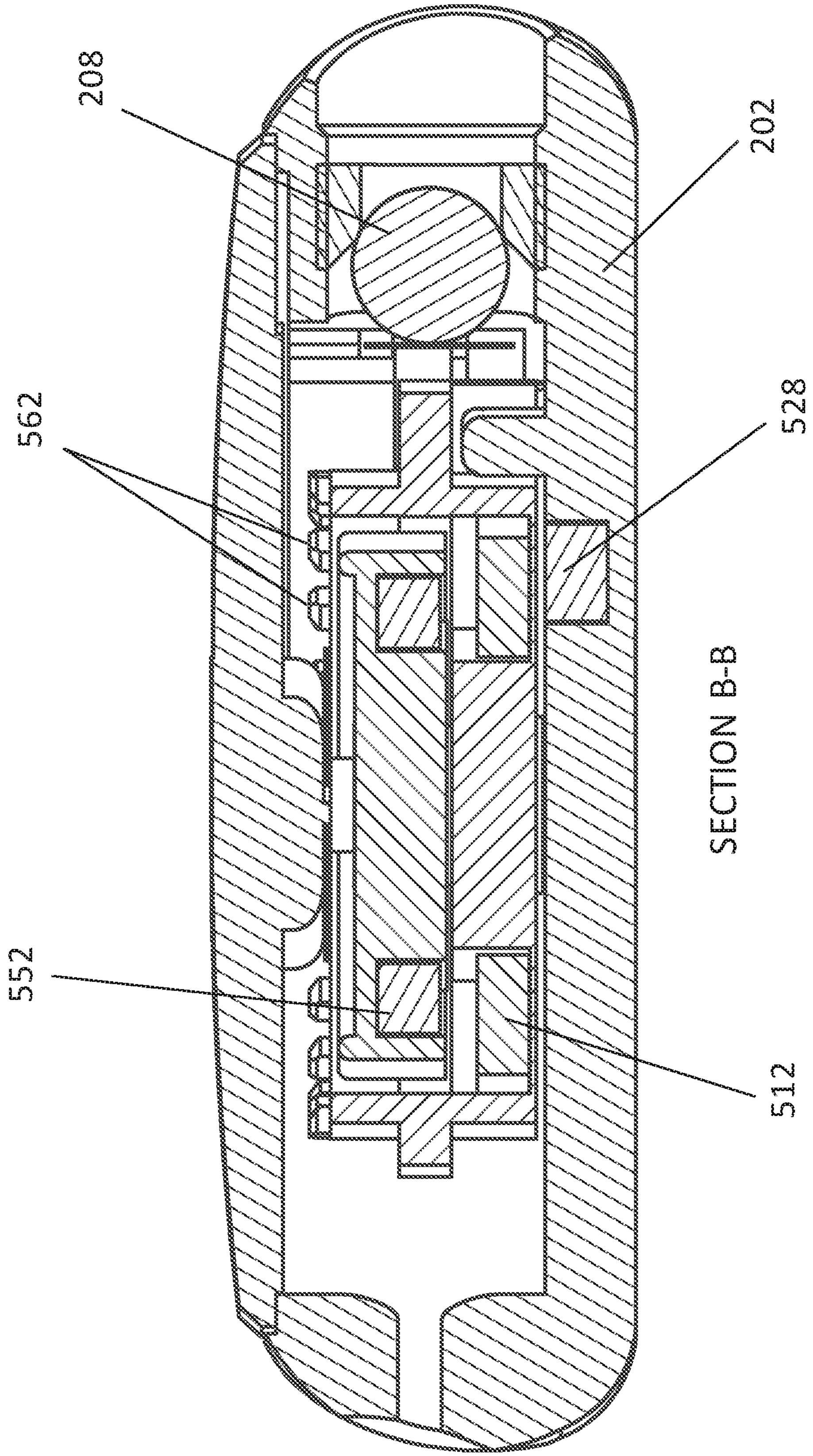
FIG. 44B is a cross-sectional view of the example of the valve shown in FIG. 42 taken along line B-B in FIG. 42.

In the examples shown in FIGS. 33, 34, 37A-B, and 40, the brake cylinder 556 includes brake cylinder teeth 560 that engage the motor teeth 562 to lock the rotor 510 in position, as discussed above. According to another embodiment, the brake spring 554 can include features that engage with the motor teeth 562, thereby removing the need for the brake cylinder teeth 560. For example, referring to FIG. 41 there is illustrated a partial cross-sectional perspective view of another embodiment of the programmable valve 200 in which the brake spring 554 includes a pair of arms 566 each having a projection 566*a* configured to engage with the motor teeth 562 to lock the rotor 510. In this example the motor teeth 562 are positioned around a circumference of the rotor casing 514. FIG. 42 is a plan view of one example of the embodiment shown in FIG. 41 in which the rotor 510 includes twelve rotor magnet elements 512. FIG. 43 is a plan view of another example of a similar embodiment to that shown in FIG. 41 in which the rotor 510 includes ten rotor magnet elements. FIG. 44A is a cross-sectional view taken along line A-A in FIG. 42, and FIG. 44B is another cross-sectional view taken along line B-B in FIG. 42. In one example, in which the rotor includes twelve rotor magnet elements 512, the plurality of motor teeth 562 includes 24 motor teeth, such that the rotor can be locked into each position corresponding to rotation step of one half-width of a rotor magnet element. However, different configurations can include different numbers of motor teeth 562.

Figure 41:
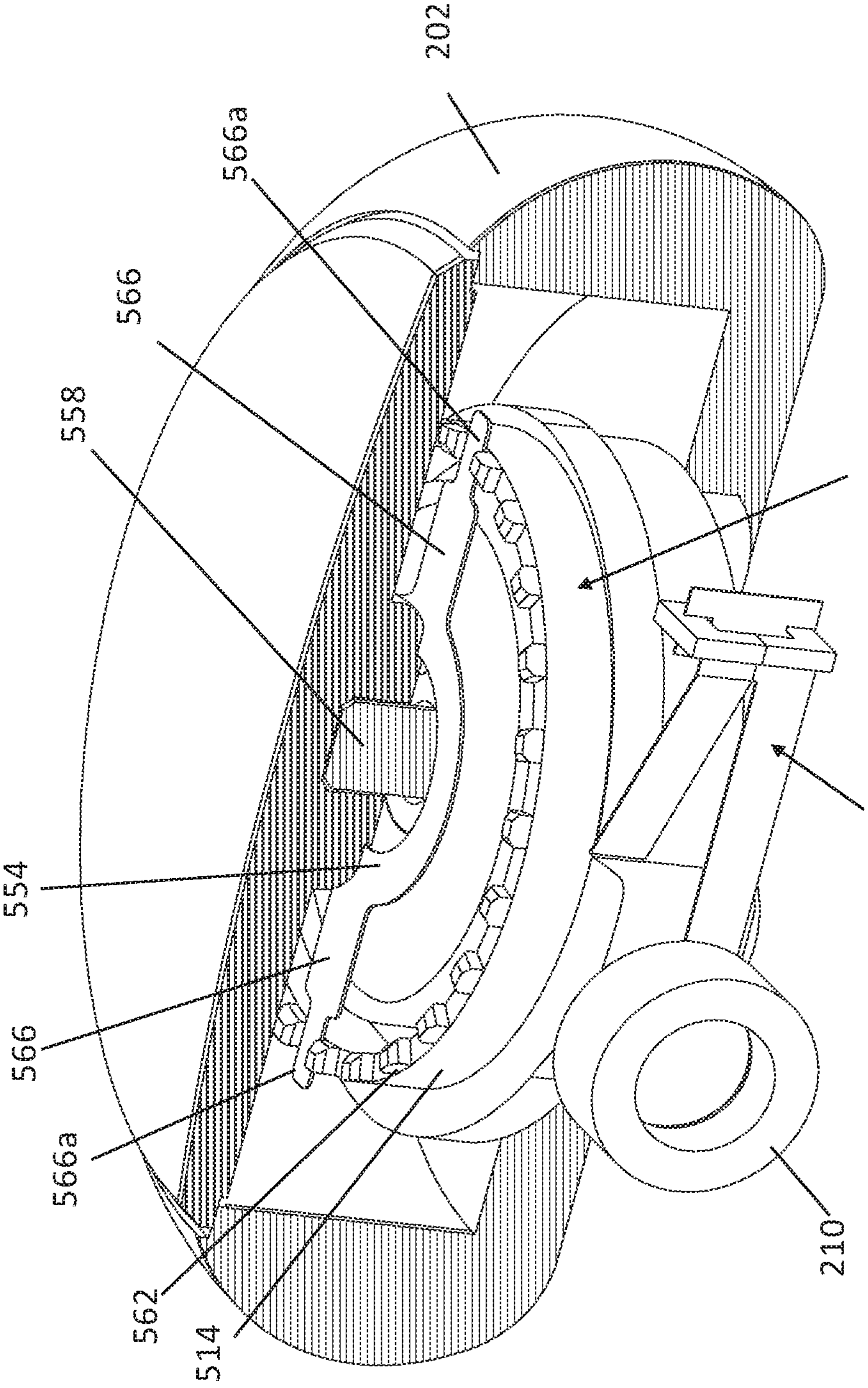
FIG. 41 is a partial cross-sectional perspective view of another example of programmable valve including a magnetic motor incorporating a brake mechanism according to aspects of the invention.
Figure 42:
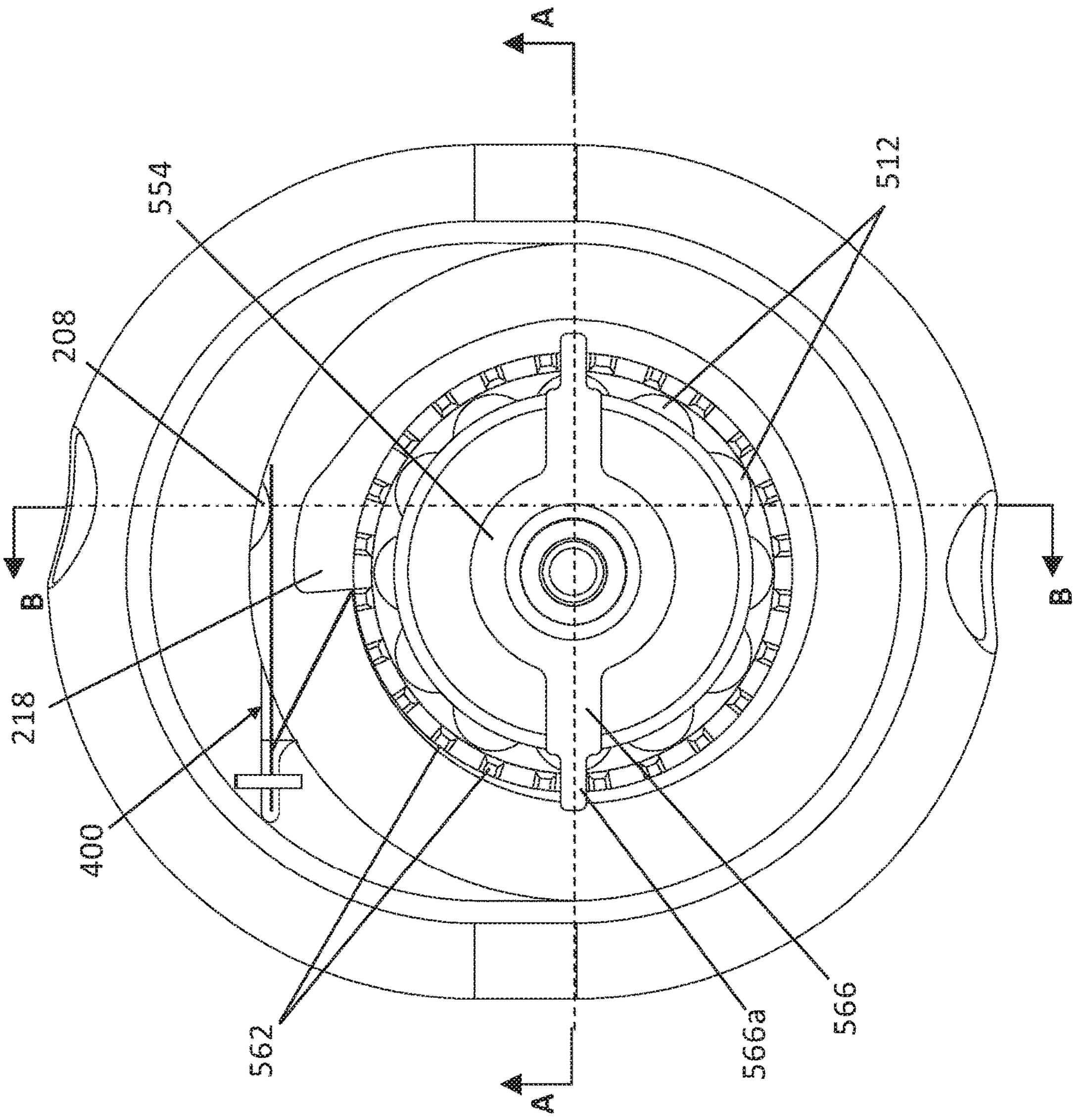
FIG. 42 is a plan view of the example of the valve shown in FIG. 41.
Figure 45:
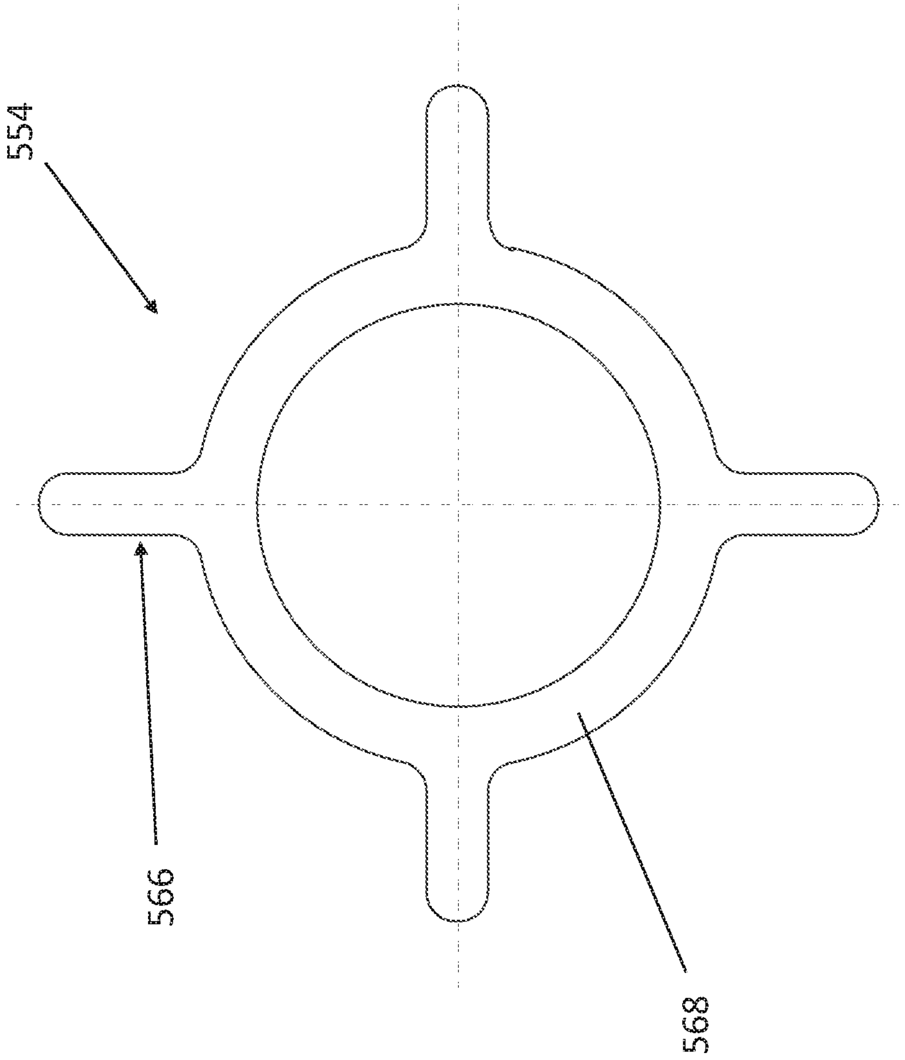
FIG. 45 is a diagram showing another example of a brake spring according to aspects of the invention.

In the examples shown in FIGS. 41 and 42, the brake spring 554 includes two arms 566, and each arm includes a projection 566*a* at its tip, the projection being thinner/narrower than the body of the arm 566 and configured to fit between a pair of adjacent motor teeth 562 when the brake is in the locked position. However, as will be appreciated by those skilled in the art, given the benefit of this disclosure, a variety of different configurations can be implemented, provided only that the brake spring 554 includes one or more features that are configured to engage with the motor teeth 562 to prevent rotation of the rotor 510. For example, the brake spring 554 shown in FIG. 43 includes arms 566 that are more uniform in width, lacking the defined projection 566*a*. Referring to FIG. 45, in another embodiment the brake spring 554 includes four arms 566, rather than two, positioned around a central ring portion 568, and the arms are more uniform in width, similar to the example shown in FIG. 43, rather than having the narrower end projections 566*a* illustrated in FIG. 40. In the examples shown in FIGS. 43 and 45, the width of the arms 566 and spacing between adjacent motor teeth 562 can be selected such that the arms can fit between adjacent motor teeth to lock to rotor 510 in position and prevent its rotation.

Figure 46A:
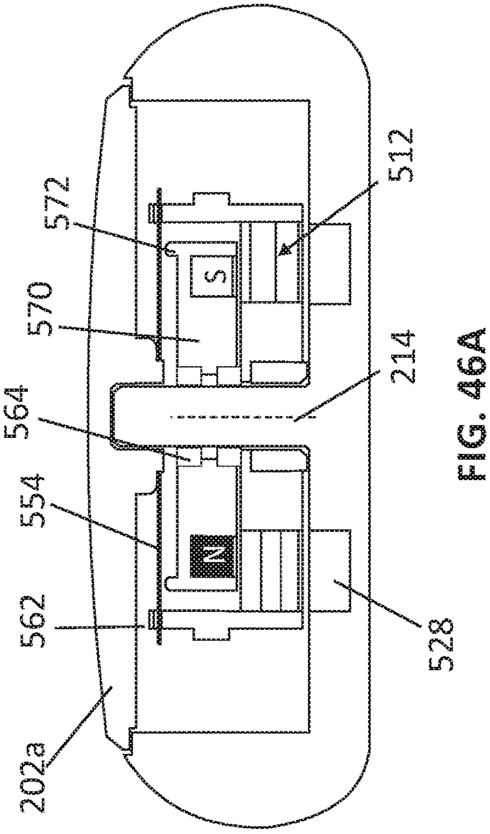
FIG. 46A is a schematic cross-sectional view of the example of the valve shown in FIG. 42, showing the brake in the locked position.
Figure 46B:
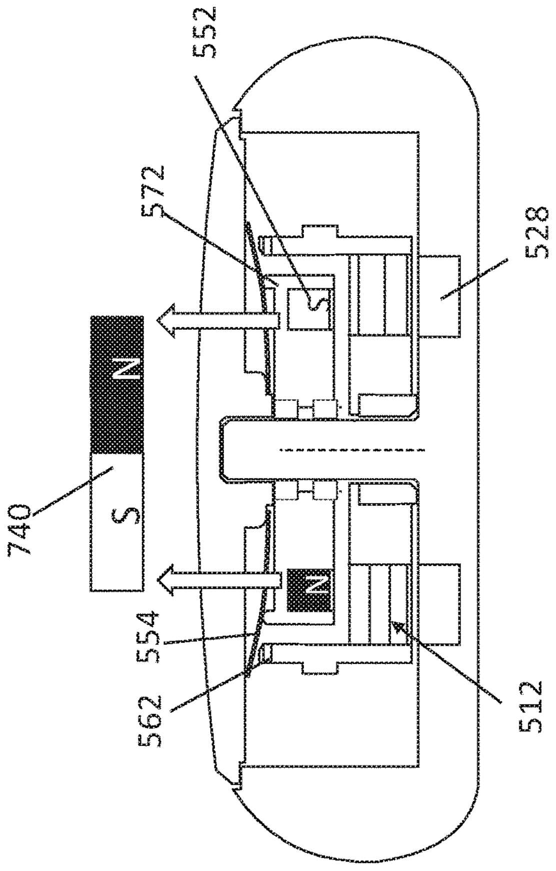
FIG. 46B is a corresponding schematic cross-sectional view of the example of the valve shown in FIG. 42, showing the brake in the unlocked position.

Referring to FIGS. 46A and 46B, embodiments of the magnetic motor that incorporate a brake mechanism using the brake spring 554 to engage the motor teeth 562 can be operated in the same manner as discussed above using a brake controller magnet 740 or 742 to unlock or release the brake. In one example, the motor teeth 562 are positioned on the top circumference of the rotor casing 514, as shown in FIG. 46A, and in the locked position, the spring 554 rests such that the arms 566 are located between adjacent motor teeth such that rotation of the rotor 510 is thereby prevented. The brake spring 554 can be supported by the top cover 202*a* of the valve. As discussed above, and as shown in FIG. 46B, when the diametrically magnetized brake controller magnet 740 or 742 is placed above the valve 200, it will attract the second indicator magnet 552 and push up the brake spring 554, thereby unlocking the rotor 510 so that it is free to rotate. As shown in FIGS. 46A and 46B, in one example the second indicator magnet 552 is located in a casing 570 that includes a casing projection 572. When the second indicator magnet 552 is pulled upwards by the brake controller magnet 740 or 742, the casing projection 572 presses against the spring arms 566, lifting the arms above the motor teeth 562 so that the rotor 510 can rotate. When the brake controller magnet 740 or 742 is removed, the brake spring 554 drops back down such that the arms 566 again rest between adjacent motor teeth 562, as shown in FIG. 46A.

Figure 47A:
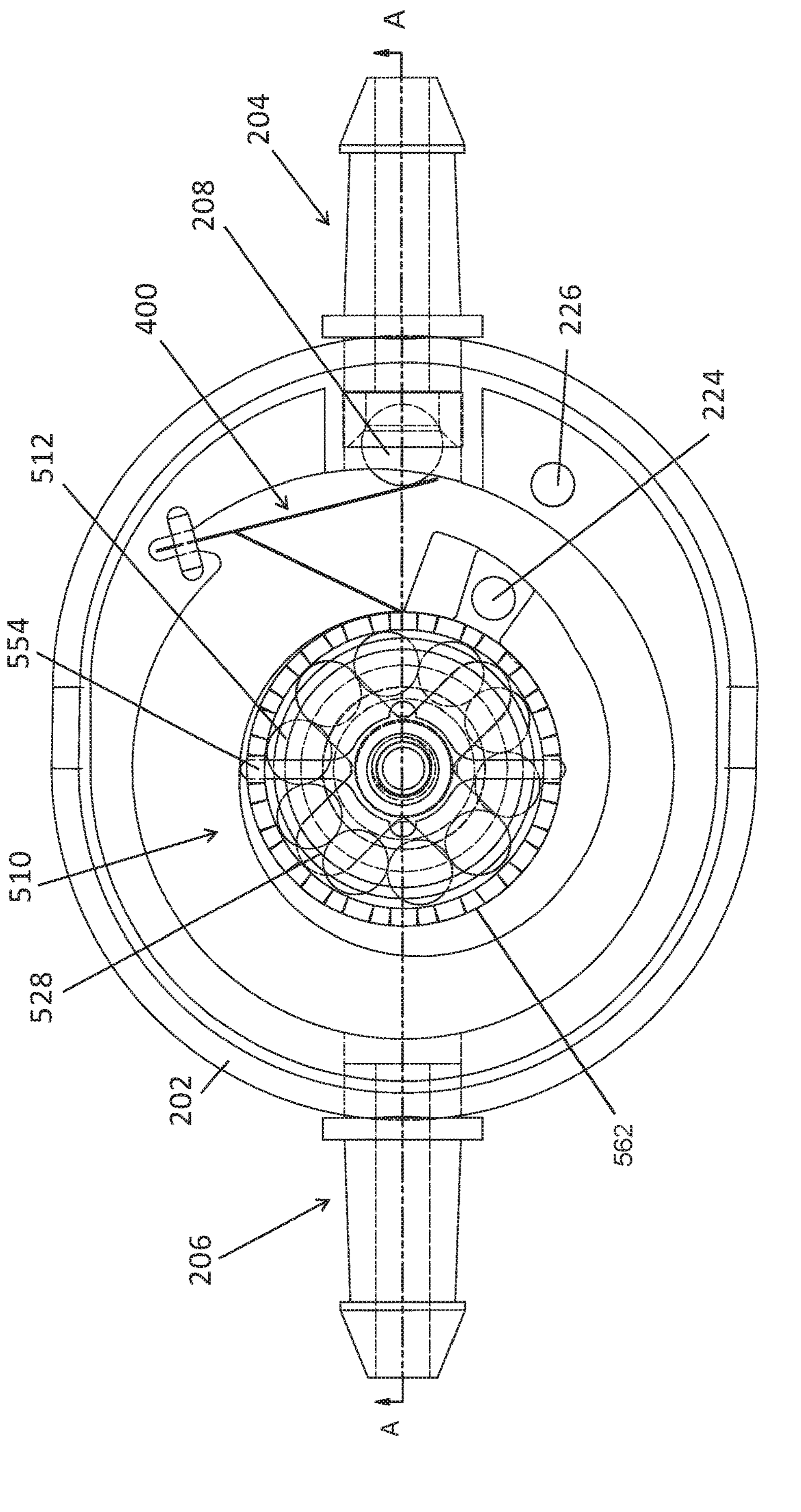
FIG. 47A is a plan view of another example of a programmable valve according to aspects of the invention.
Figure 47B:
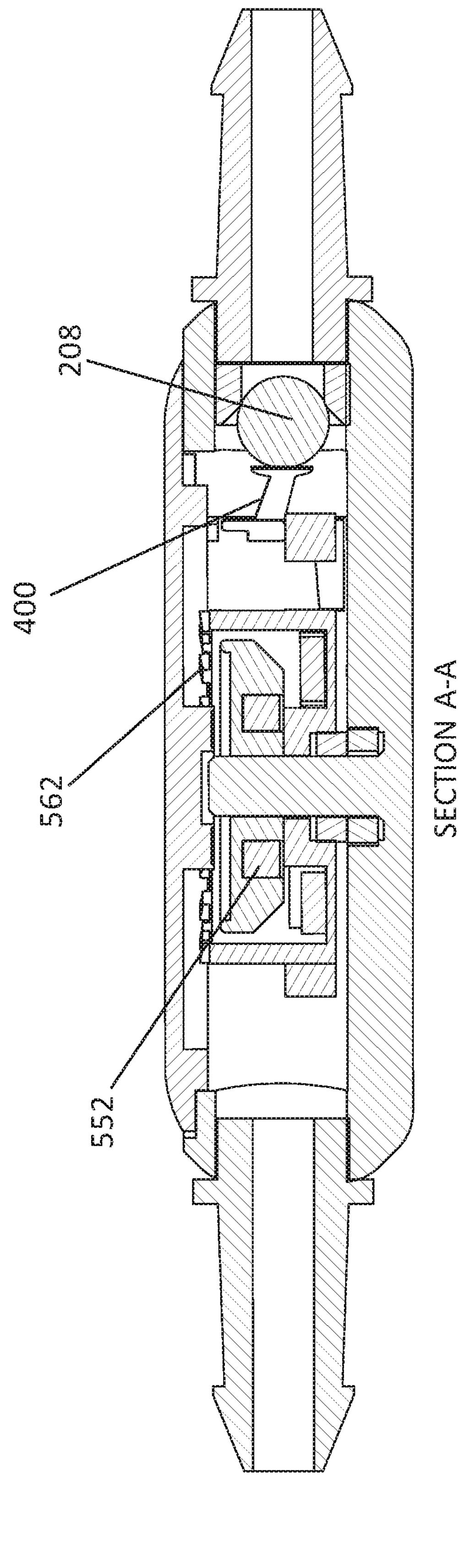
FIG. 47B is a cross-sectional view of the programmable valve shown in FIG. 47A taken along line A-A in FIG. 47A.

FIGS. 47A and 47B show another example of a programmable valve 200 including a ten-magnet rotor 510, also showing an example of the brake mechanism. FIG. 47A is a plan view of the programmable valve 200, and FIG. 47B is a cross-sectional view taken along line A-A in FIG. 47A.

Figure 48:
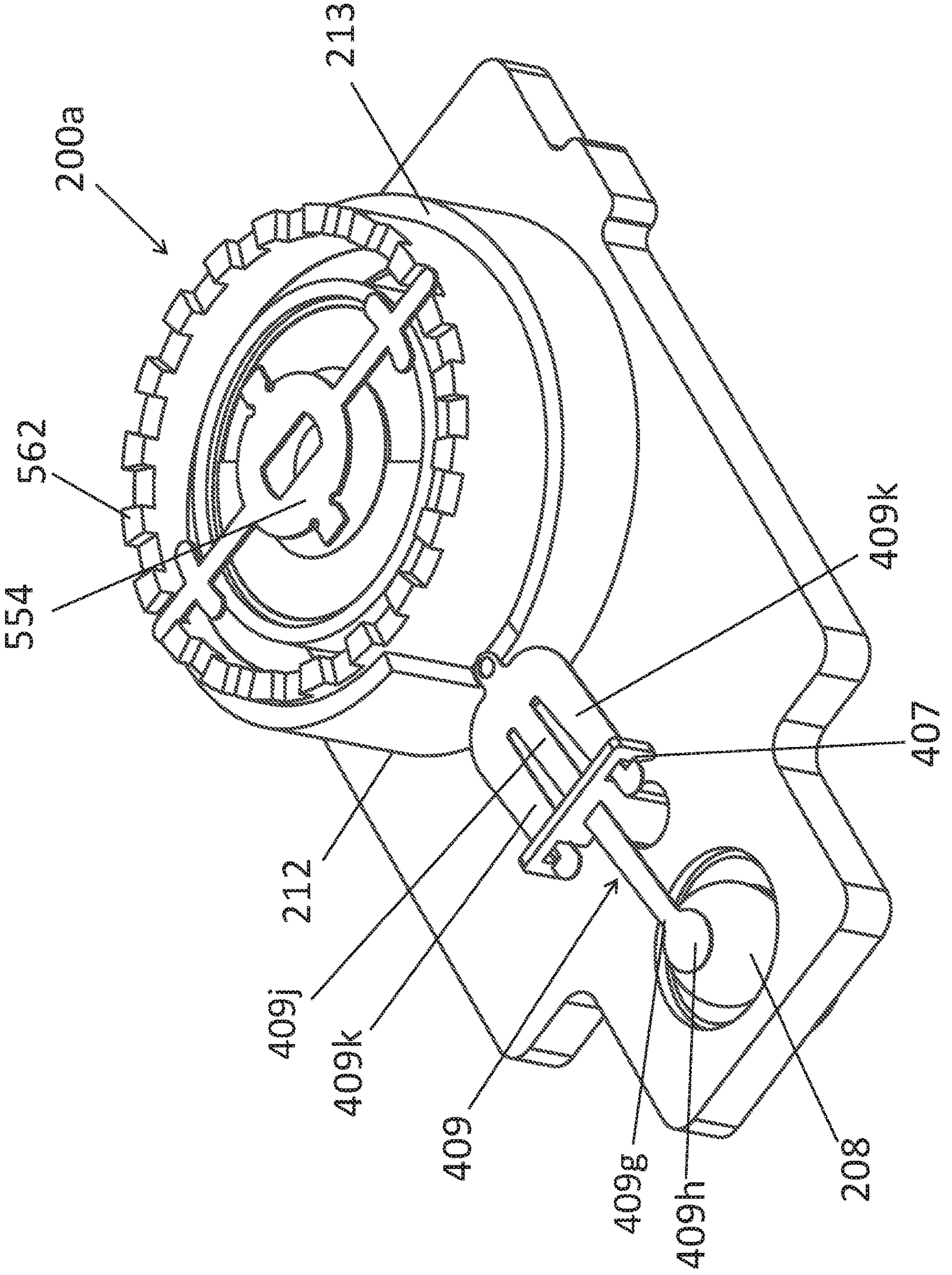
FIG. 48 shows another example of a programmable valve incorporating a brake mechanism according to aspects of the present invention.

FIG. 48 shows another example of a programmable valve 200*a* including a stepper motor, a brake mechanism, and an indicator magnet assembly according to certain embodiments. In this example the cam 212 has an inclined surface 213 and the spring 409 includes a central arm 409*j* flanked by two parallel arms 409*k*. The central arm 409*j* is a cantilevered arm with a free end 409*h* resting against the valve element 208, and the two parallel arms 409*k* are fixed to the underside of a pivot point 407. The relationship between the position of the cam 212 and the tension of the spring 409 is dependent on the location of the pivot point 407, the point of the contact between the spring 409 and the cam 212, and the point of contact between the cantilevered arm 409*g* and the valve element 208. Depending on these relationships, when the cam 212 is at its highest position, the cantilevered arm 409*g* can be pushed toward the valve element 208, or alternatively, the cantilevered arm 409*g* can be pushed away from the valve element 208. In the configuration depicted in FIG. 48, when the cam 212 is at its highest position (or its highest level of incline) against the spring 409, the tension of the spring 409 is the greatest and tends to push the cantilevered arm 409*g* in the direction toward the valve element 208. The valve 200*a* of FIG. 48 incorporates brake teeth 562 that engage a brake spring 554, as discussed above, to prevent unwanted changes to the pressure setting of the valve 200*a* when exposed to a magnetic field (other than a programming field).

Embodiments of the valve assembly 100 may be implanted in a patient using well-described surgical procedures. The pressure setting of the valve 200 can be adjusted to a desired pressure setting prior to surgical implantation. In one aspect, the working pressure can be set to be approximately equal to the patient's ventricular CSF pressure such that no pressure change occurs after the surgery. After the patient recovers from surgery, the pressure setting can be adjusted as desired. For example, in a patient suffering from NPH, the pressure setting can be decreased in order to initiate a reduction in the size of the ventricles. Additional adjustments in the pressure setting can additionally be made. For example, once the size of the ventricles had been reduced sufficiently, the pressure setting of the valve can be increased. As will be appreciated, use of the implanted valve 200 permits the pressure setting of the valve 200 to be externally adjusted as needed over the course of treating the patient.

In certain embodiments, a method of treating hydrocephalus includes implanting an embodiment of the valve assembly 100 having a ventricular catheter 120 within a ventricular cavity of the patient's brain and distal catheter connected to the connector 140 installed at a remote location in the patient's body where the fluid is to drain. Remote locations of the body where CSF drains include, for example, the right atrium of the heart and the peritoneum.

In addition to hydrocephalus, there are several other conditions associated with the accumulation of excess fluid and that can be treated by draining the fluid using a suitably-designed inflow catheter into another part of the body. Such conditions include, for example, chronic pericardial effusions, chronic pulmonary effusion, pulmonary edema, ascites, and glaucoma in the eye. It is contemplated that embodiments of the programmable valve 200 may be used in the treatment of these conditions.

The pressure settings of the valves described herein can be adjusted in many discrete steps or increments, or continuously over a predetermined range, as discussed above. Embodiments of the valves described herein may vary in pressure from a low pressure, for example, 10 mm $H_2O$, to a high pressure, for example 400 mm $H_2O$. Most conventional valves only have pressures as high as 200 mm $H_2O$ and can only be adjusted in relatively high increments between each pressure setting.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A surgically-implantable shunt valve assembly comprising:
- a housing, an exterior of the housing being formed of a physiologically-compatible material;
- a magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, rotation of the rotor relative to the stator producing a selected pressure setting of the shunt valve assembly;
- an inlet port positioned between the rotor casing and an exterior of the housing, the inlet port terminating at its rotor casing end in a valve seat;
- a spring;
- a valve element biased against the valve seat by the spring, the valve element and the valve seat together forming an aperture;
- an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port;
- at least one first reference magnet disposed proximate to the center of the rotor, the rotor and the at least one first reference magnet configured to rotate about a common axis of rotation; and
- a second reference magnet configured to rotate with the at least one first reference magnet about the common axis of rotation,
- wherein the second reference magnet produces a second magnetic field that is stronger than a first magnetic field produced by the at least one first reference magnet.

2. The surgically-implantable shunt valve assembly of claim 1 wherein the rotor casing includes a cam that engages the spring such that rotation of the rotor changes a biasing tension of the spring against the cam thereby adjusting a tension of the spring against the valve element to produce the selected pressure setting of the shunt valve assembly.

3. The surgically-implantable shunt valve assembly of claim 2, wherein the spring is a cantilever spring.

4. The surgically-implantable shunt valve assembly of claim 3, wherein the cantilever spring includes a cantilevered arm that rests against the valve element and a second arm that rests against the cam.

5. The surgically-implantable shunt valve assembly of claim 2 wherein the rotor casing further includes a cam stop that prevents 360 degree rotation of the rotation of the rotor.

6. The surgically-implantable shunt valve assembly of claim 1 wherein the stator is X-shaped.

7. The surgically-implantable shunt valve assembly of claim 6 wherein the X shape of the stator has an orientation of 90 degrees between each stator arm.

8. The surgically-implantable shunt valve assembly of claim 6 wherein the X shape of the stator has an orientation of alternating 75 degrees and 105 degrees between stator arms.

9. The surgically-implantable shunt valve assembly of claim 1, further comprising a cam which engages the spring and is integrated with the rotor casing, such that the rotation of the rotor causes rotation of the cam and adjusts a tension of the spring against the valve element, and wherein the spring is a cantilever spring including:
- a fulcrum;
- a first arm attached to the fulcrum and configured to engage the cam; and
- a cantilevered arm extending from the fulcrum and having a free end configured to rest against the valve element;
- wherein the fulcrum, the first arm, and the cantilevered arm are configured to provide a lever effect such that a first pressure applied by the cam to the first arm is translated by the cantilever spring into a second pressure applied against the valve element, the second pressure being less than the first pressure.

10. The surgically-implantable shunt valve assembly of claim 1 wherein the at least one first reference magnet is positioned over a corresponding at least one of the rotor permanent magnet elements.

11. The surgically-implantable shunt valve assembly of claim 1 wherein the magnetically operable motor further includes first and second position indicator magnets that allow an external sensor to magnetically determine a position of the rotor.

12. The surgically-implantable shunt valve assembly of claim 11 wherein the first position indicator magnet is coupled to the rotor and rotates with the rotor, and wherein the second position indicator magnet rotates about the central axis of rotation on a bearing independent of rotation of the rotor.

13. The surgically-implantable shunt valve assembly of claim 12 wherein the second indicator magnet is a diametrically magnetized ring-shaped magnet.

14. The surgically-implantable shunt valve assembly of claim 1 further comprising a cam that engages the spring and is coupled to the rotor, such that the rotation of the rotor causes rotation of the cam and adjusts a tension of the spring against the valve element.

15. The surgically-implantable shunt valve assembly of claim 14 wherein the cam is a disc cam.

16. The surgically-implantable shunt valve assembly of claim 1 wherein the spring is a cantilever spring that includes a cantilevered arm and a second arm extending substantially parallel to one another from a fixed point of attachment of the spring, the cantilevered arm having a free end that rests against the valve element.

17. The surgically-implantable shunt valve assembly of claim 16 wherein the cantilever spring includes a cantilevered arm that rests against the valve element and a second arm that rests against the cam.

18. The surgically-implantable shunt valve assembly of claim 17 wherein the cantilevered arm and the second arm extend in a same direction from a fixed point of attachment of the spring, the second arm including a point of inflection from which the second arm angles away from the cantilevered arm.

19. The surgically-implantable shunt valve assembly of claim 1 wherein the valve element is a spherical valve element.

20. The surgically-implantable shunt valve assembly of claim 1 wherein a number of the rotor permanent magnet elements is such that radially opposing ones of the plurality of rotor permanent magnet elements have the same magnetic polarity.

21. The surgically-implantable shunt valve assembly of claim 20 wherein the number of the rotor permanent magnet elements is twelve.

22. The surgically-implantable shunt valve assembly of claim 20 wherein a number of the rotor permanent magnet elements is ten.

23. The surgically-implantable shunt valve assembly of claim 1 wherein a number of the rotor permanent magnet elements is such that radially opposing ones of the plurality of rotor permanent magnet elements have opposite magnetic polarity.

24. The surgically-implantable shunt valve assembly of claim 1 wherein the stator includes a plurality of discrete stator elements.

25. The surgically-implantable shunt valve assembly of claim 1 wherein the second magnetic field has sufficient strength to be detected by a compass or a Hall sensor placed in proximity to the shunt valve assembly.

26. The surgically-implantable shunt valve assembly of claim 1 wherein the second reference magnet is in the shape of a ring, configured to rotate with the at least one first reference magnet about the common axis of rotation.

27. The surgically-implantable shunt valve assembly of claim 1 wherein the fluid is cerebrospinal fluid.

28. A surgically-implantable shunt valve assembly comprising:

a housing, an exterior of the housing being formed of a physiologically-compatible material;

a magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, rotation of the rotor relative to the stator producing a selected pressure setting of the shunt valve assembly;

an inlet port positioned between the rotor casing and an exterior of the housing, the inlet port terminating at its rotor casing end in a valve seat;

a spring;

a valve element biased against the valve seat by the spring, the valve element and the valve seat together forming an aperture;

an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port;

at least one first reference magnet disposed proximate to the center of the rotor, the rotor and the at least one first reference magnet being configured to rotate about a common axis of rotation;

a second reference magnet element configured to rotate with the at least one first reference magnet about the common axis of rotation; and a magnetically operated mechanical brake having a locked position and an unlocked position, and wherein the motor includes a plurality of motor teeth, the magnetically operated mechanical brake being configured, in the locked position, to engage with the plurality of motor teeth to prevent rotation of the rotor.

29. The surgically-implantable shunt valve assembly of claim 28 wherein the magnetically operated mechanical brake includes a brake cylinder disposed about the common axis of rotation, and a brake spring attached to the brake cylinder, the brake cylinder being coupled to the second reference magnet and configured to move vertically responsive to an external magnetic field applied to the second reference magnet to transition the mechanical brake from the locked position into the unlocked position.

30. The surgically-implantable shunt valve assembly of claim 29 wherein the brake cylinder includes a plurality of brake cylinder teeth configured to engage with the plurality of motor teeth when the mechanical brake is in the locked position.

31. The surgically-implantable shunt valve assembly of claim 29 wherein the plurality of motor teeth are disposed on an upper circumferential surface of the rotor casing, and wherein the brake spring includes at least one arm configured to rest between adjacent ones of the plurality of motor teeth when the mechanical brake is in the locked position.

32. A surgically-implantable shunt valve assembly comprising:

a housing, an exterior of the housing being formed of a physiologically-compatible material;

a magnetically operable motor disposed within the housing, the magnetically operable motor including a stator and a rotor configured to rotate relative to the stator responsive to a changing magnetic polarity of the stator induced by an external magnetic field, the rotor including a rotor casing and a plurality of rotor permanent magnet elements disposed in a ring within the rotor casing and arranged with alternating magnetic polarities, rotation of the rotor relative to the stator producing a selected pressure setting of the shunt valve assembly;

an inlet port positioned between the rotor casing and an exterior of the housing, the inlet port terminating at its rotor casing end in a valve seat;

a spring;

a valve element biased against the valve seat by the spring, the valve element and the valve seat together forming an aperture;

an outlet port positioned between the rotor casing and the exterior of the housing, the shunt valve assembly configured such that the aperture opens when a pressure of the fluid in the inlet port exceeds the selected pressure setting of the shunt valve assembly so as to vent fluid through the aperture into the outlet port;

at least one reference magnet disposed proximate to the center of the rotor and configured to rotate about a common axis of rotation; and a magnetically operated mechanical brake having a locked position and an unlocked position, and wherein the motor includes a plurality of motor teeth, the magnetically operated mechanical brake being configured, in the locked position, to engage with the plurality of motor teeth to prevent rotation of the rotor.

33. The surgically-implantable shunt valve assembly of claim 32 wherein the magnetically operated mechanical brake includes a brake cylinder disposed about the common axis of rotation, and a brake spring attached to the brake cylinder, the brake cylinder being coupled to the at least one reference magnet and configured to move vertically responsive to an external magnetic field applied to the at least one reference magnet to transition the mechanical brake from the locked position into the unlocked position.

34. The surgically-implantable shunt valve assembly of claim 33 wherein the brake cylinder includes a plurality of brake cylinder teeth configured to engage with the plurality of motor teeth when the mechanical brake is in the locked position.

35. The surgically-implantable shunt valve assembly of claim 33 wherein the plurality of motor teeth are disposed on an upper circumferential surface of the rotor casing, and wherein the brake spring includes at least one arm configured to rest between adjacent ones of the plurality of motor teeth when the mechanical brake is in the locked position.

36. The surgically-implantable shunt valve assembly of claim 32 wherein the plurality of motor teeth are disposed on an upper circumferential surface of the rotor casing, and wherein the brake spring includes at least one arm configured to rest between adjacent ones of the plurality of motor teeth when the mechanical brake is in the locked position, the at least one reference magnet being configured to move vertically responsive to an external magnetic field applied to the at least one reference magnet to transition the mechanical brake from the locked position into the unlocked position by vertically displacing the at least one arm of the brake spring.

* * * * *